United States Patent
Weeks et al.

(10) Patent No.: US 11,707,182 B2
(45) Date of Patent: Jul. 25, 2023

(54) ENDOSCOPE AND ENDOSCOPE SHEATH WITH DIAGNOSTIC AND THERAPEUTIC INTERFACES

(71) Applicant: PacificMD Biotech, LLC, Henderson, NV (US)

(72) Inventors: Brian Hunter Weeks, San Diego, CA (US); Ashley Sikand, Las Vegas, NV (US); Jetmir Palushi, Irvine, CA (US)

(73) Assignee: PACIFICMD BIOTECH, LLC, Henderson, NV (US)

( * ) Notice: Subject to any disclaimer, the term of this patent is extended or adjusted under 35 U.S.C. 154(b) by 0 days.

(21) Appl. No.: 17/702,628

(22) Filed: Mar. 23, 2022

(65) Prior Publication Data

US 2022/0304559 A1  Sep. 29, 2022

Related U.S. Application Data

(60) Provisional application No. 63/280,397, filed on Nov. 17, 2021, provisional application No. 63/237,618, (Continued)

(51) Int. Cl.
*A61B 1/00* (2006.01)
*A61B 1/05* (2006.01)
(Continued)

(52) U.S. Cl.
CPC ...... *A61B 1/00135* (2013.01); *A61B 1/00009* (2013.01); *A61B 1/015* (2013.01);
(Continued)

(58) Field of Classification Search
None
See application file for complete search history.

(56) References Cited

U.S. PATENT DOCUMENTS 4,699,125 A * 10/1987 Komatsu ............ H04N 5/23267
600/921
5,007,407 A *  4/1991 Kikuchi ................ A61B 1/042
600/117

(Continued)

FOREIGN PATENT DOCUMENTS

CN         209172249       *   7/2019    ............... A61B 1/00

OTHER PUBLICATIONS

International Search Report and Written Opinion of the International Searching Authority for International Patent App. No. PCT/US2022/16141 dated Apr. 25, 2022 (11 pages).

*Primary Examiner* — Timothy J Neal
(74) *Attorney, Agent, or Firm* — Ulmer & Berne LLP

(57) ABSTRACT

A removable and replaceable sheath may be coupled to a medical instrument used during a procedure, and may enable one or more functional features of the medical instrument while maintaining a sterile barrier between the instrument itself and the treatment site. The sheath may be replaced prior to a subsequent use, and sterilization of the medical instrument is not required due to the sterile barrier. Sheaths may include an embedded memory that stores procedure configurations and procedure results, longitudinal channels for delivering power or irrigation, optical elements for providing procedure specific endoscopic views, and other features. One sheath may be fitted to an endoscope for imaging and tissue ablation. Another sheath includes a balloon usable during sinuplasty procedures. Yet another sheath may be fitted to a sonic ablation instrument to provide improved transmission of sonic power to tissue.

17 Claims, 33 Drawing Sheets

Related U.S. Application Data filed on Aug. 27, 2021, provisional application No. 63/165,554, filed on Mar. 24, 2021.

(51) Int. Cl.

| | | |
|---|---|---|
| *A61B 1/018* | (2006.01) | |
| *A61B 1/06* | (2006.01) | |
| *A61B 1/015* | (2006.01) | |
| *A61B 1/045* | (2006.01) | |

(52) U.S. Cl.
CPC .............. *A61B 1/018* (2013.01); *A61B 1/045* (2013.01); *A61B 1/05* (2013.01); *A61B 1/0676* (2013.01); *A61B 1/0684* (2013.01)

(56) References Cited

U.S. PATENT DOCUMENTS

| | | | | |
|---|---|---|---|---|
| 5,873,816 | A * | 2/1999 | Kagawa | A61B 1/00114 600/110 |
| 6,537,207 | B1 * | 3/2003 | Rice | A61B 1/00142 600/103 |
| 6,712,758 | B1 * | 3/2004 | Campbell | G02B 23/2476 385/117 |
| 6,734,894 | B1 * | 5/2004 | Higuchi | H04N 7/183 348/69 |
| 6,847,490 | B1 * | 1/2005 | Nordstrom | A61B 1/00142 600/407 |
| 2004/0186382 | A1 * | 9/2004 | Modell | A61B 1/00059 600/476 |
| 2004/0231772 | A1 * | 11/2004 | Leonard | A61B 1/00142 150/161 |
| 2007/0085686 | A1 * | 4/2007 | Oz | A61B 1/00016 235/492 |
| 2008/0051634 | A1 * | 2/2008 | Yamashita | A61B 1/00071 600/153 |
| 2009/0256934 | A1 * | 10/2009 | Usami | G02B 23/2484 348/241 |
| 2010/0286475 | A1 * | 11/2010 | Robertson | A61B 1/00188 600/109 |
| 2013/0158349 | A1 * | 6/2013 | Ashida | A61B 1/00128 600/114 |
| 2014/0276603 | A1 * | 9/2014 | Magee | A61B 90/90 604/95.01 |
| 2016/0133014 | A1 | 5/2016 | Staples et al. | |
| 2017/0127915 | A1 * | 5/2017 | Viebach | A61B 1/0057 |
| 2017/0136136 | A1 * | 5/2017 | Li | A61L 2/10 |
| 2017/0280988 | A1 * | 10/2017 | Barbato | A61B 1/317 |
| 2017/0367564 | A1 * | 12/2017 | Aruga | A61B 90/90 |
| 2018/0153383 | A1 | 6/2018 | Goshayesh et al. | |
| 2019/0231220 | A1 | 8/2019 | Refai et al. | |
| 2019/0297276 | A1 | 9/2019 | Sachdev et al. | |
| 2020/0297444 | A1 | 9/2020 | Camarillo et al. | |
| 2020/0305699 | A1 * | 10/2020 | Herriges | A61B 1/00087 |
| 2021/0015554 | A1 | 1/2021 | Chow et al. | |
| 2021/0037173 | A1 | 2/2021 | Uemori et al. | |
| 2021/0161555 | A1 * | 6/2021 | Winegar | A61B 1/05 |

\* cited by examiner

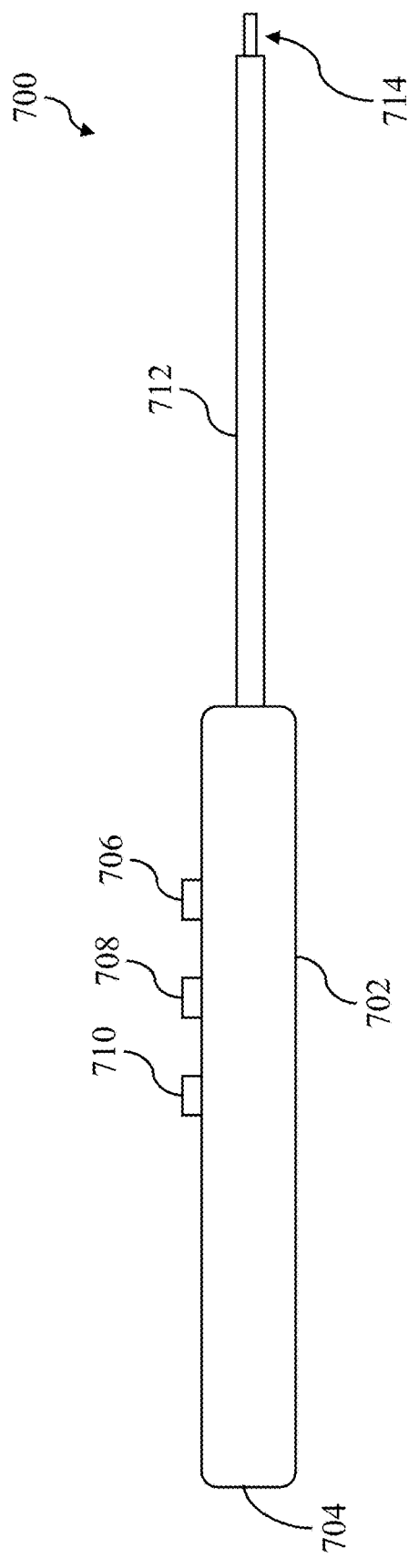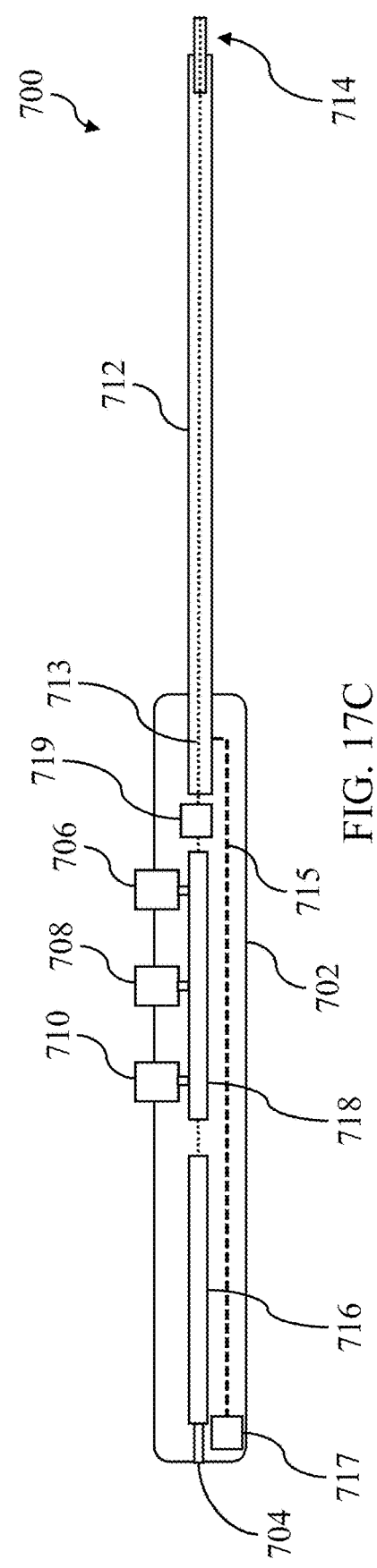
FIG. 17B
FIG. 17C

ENDOSCOPE AND ENDOSCOPE SHEATH WITH DIAGNOSTIC AND THERAPEUTIC INTERFACES

PRIORITY

This application claims priority to U.S. Provisional Patent 63/165,554, filed Mar. 24, 2021, U.S. Provisional Patent 63/237,618, filed Aug. 27, 2021, and U.S. Provisional Patent 63/280,397, filed Nov. 17, 2021, each of the preceding titled "Endoscope and Endoscope Sheath with Diagnostic and Therapeutic Interfaces," and each of which are hereby incorporated herein by reference in their entirety.

FIELD

The disclosed technology pertains to an endoscope sheath for use with an endoscope that provides therapeutic and diagnostic application while maintaining scope sterility throughout the procedure.

BACKGROUND

Maintaining sterility of medical instruments and tools is a top priority for any medical procedure that involves a risk of infection. Procedures relating to sterility introduce a significant cost in time and materials to many medical settings. Some medical instruments are produced in a sterile environment and provided in a sterile packaging by manufacturers. Some medical instruments must be sterilized after each procedure by use of capital equipment such as sterilization cabinets that provide pressurized flows of disinfectant, heat, or other treatments during lengthy sterilization procedures, and must be tracked and maintained through each stage of sterilization to provide auditable chain of custody logs. Other medical instruments cannot be effectively sterilized, and so must be treated and disposed as biohazardous waste.

While such procedures greatly increase the quality of care and patient outcomes, they also represent significant cost and waste. As one example, some estimates indicate that reprocessing an endoscope for subsequent use requires around 80 minutes of manual interaction, and nearly $300 in costs related to use of capital equipment and materials that are consumed during the process. Even with such reprocessing, the risk of cross contamination is reduced but not completely mitigated. Endoscopes, tissue ablation tools, sonic cutters, and other tools used in sinuplasty procedures and other procedures may cost thousands of dollars, and may be disposed of after use, or may undergo a limited number of reprocessing procedures (e.g., 5-10), at significant cost, before they must be disposed of.

What is needed, therefore, is an improved device and method for providing sterile procedures.

BRIEF DESCRIPTION OF THE DRAWINGS

The drawings and detailed description that follow are intended to be merely illustrative and are not intended to limit the scope of the invention as contemplated by the inventors.

FIG. 17B is a side elevation view of the endoscope of FIG. 17A.

FIG. 17C is a cross sectional side elevation view of the endoscope of FIG. 17A.

DETAILED DESCRIPTION

The inventors have conceived of novel technology that, for the purpose of illustration, is disclosed herein as applied in the context of an endoscope and functional endoscope sheath. While the disclosed applications of the inventors' technology satisfy a long-felt but unmet need in the art of endoscope sheaths, it should be understood that the inventors' technology is not limited to being implemented in the precise manners set forth herein, but could be implemented in other manners without undue experimentation by those of ordinary skill in the art in light of this disclosure. Accordingly, the examples set forth herein should be understood as being illustrative only, and should not be treated as limiting.

Implementations of the disclosed technology may include a disposable sheath that includes one or several functional characteristics, and an endoscope or other instrument to which the sheath may be coupled. During use, the sheath is the only part of the medical instrument that contacts the patient, and so the medical instrument can be ready for a subsequent use by removing and disposing of a used sheath, and then opening/unsealing and installing a new sterile sheath.

In addition to providing a low cost and easily replaceable sterile shield between patients and reusable medical instrument such as an endoscope or tissue ablation tool, implementations of the disclosed technology may include varying combinations of functional features that are enabled by a particular sheath and/or are encapsulated by the sheath to maintain their sterility, which may include optical components, use tracking and diagnostic features, procedure software auto-configuration, fluid and/or drug delivery, tissue ablation through electric or sonic power delivery, delivery of sinuplasty balloon or other medical device, structure, or material, and other features that will be described in more detail below.

Figure 1:
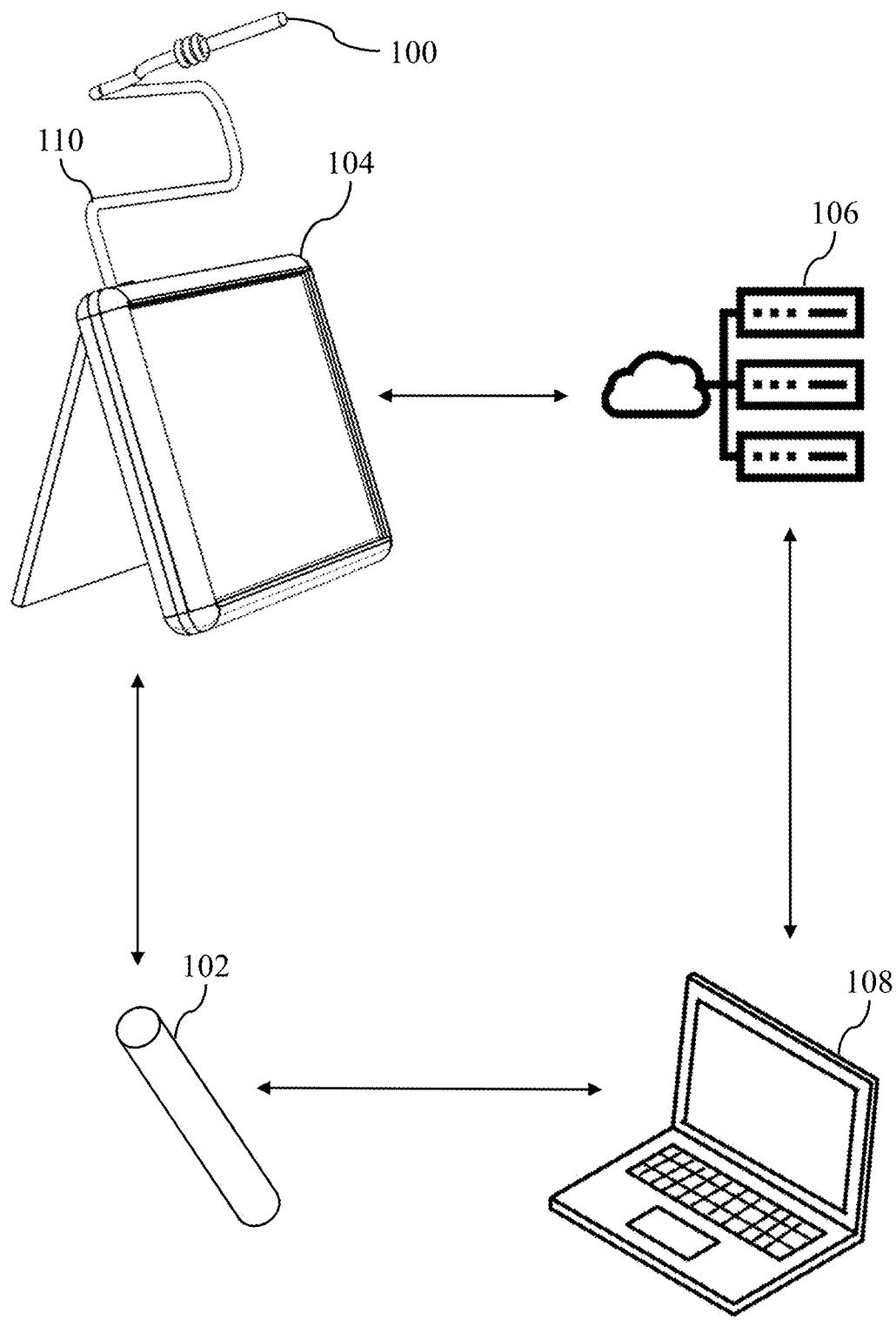
FIG. 1 is a schematic diagram of an exemplary system configured to provide medical imaging and/or treatment.

Turning now to the figures, FIG. 1 shows a schematic diagram of a system configured to provide medical imaging and/or treatment. The system includes a medical instrument in the form of an endoscope (100), which may be flexible, semi-flexible or rigid that is coupled to an image processor (104) by a cable (110), which may be a flexible or semi-flexible multi-channel cable that allows for the exchange of power and data between the image processor (104) and the endoscope (100). An endoscope sheath (102) is configured to couple with the endoscope (100) to provide a sterile barrier between the patient and endoscope (100). The endoscope sheath (102) may contain a memory device, microprocessor, and communication device (e.g., a wireless or wired data connection) allowing for the exchange of data between the endoscope sheath (102) and a coupled endoscope (100), and also allowing for communication between the endoscope sheath (102) and other devices such as a user device (108).

The image processor (104) and user device (108) may each be in communication with a remote server (106), and may exchange diagnostic information, troubleshooting information, software configurations, software applications, and other information. Functions performed by the remote server (106), image processor (104), and user device (108) may include some or all of those described in U.S. patent application Ser. No. 17/669,952, filed Feb. 11, 2022, and titled "Systems and Methods for Endoscopic Imaging and Analysis," the entire disclosure of which is hereby incorporated by reference herein. Diagnostic information, troubleshooting information, and other information also can be exchanged via the sheath memory, where this information is stored in the case of such an event occurring, and the sheath is sent back to the manufacturer where they can download this information for further analysis.

Information stored on a memory of the endoscope sheath (102) may include, for example, procedure configurations and other software configurations, serial numbers or other unique identifying data, information usable with the image processor (104) or remote server (106) to authenticate, validate, or otherwise provide access to or enable features of one or more of those devices. The endoscope sheath (102) may be preconfigured with a set of initial information, and may be configured to receive and store additional information during use with the endoscope (100), which may include diagnostic information from the endoscope (100) and/or image processor (104), error codes, performance characteristics, performance results, captured images, captured video sequences, results of image analysis, results of analysis for anatomical characteristics, and other information. The sheath memory also store data usable to update or further optimize the algorithm residing within the image processor (104) (e.g., updated software or image analysis datasets may be delivered to the image processor (104) via the sheath memory).

As one example, the image processor (104) and/or remote server (106) may be configured to provide automated image analysis of image data captured by the endoscope (100) to aid in identifying target tissues, anatomical structures, or medical concerns that may be apparent in captured image data. This image analysis feature may only be usable when an activation key or other data is received from the endoscope sheath (102) upon coupling with the endoscope (100), and then provided to the image processor (104) and/or remote server (106) where the activation key is validated or otherwise authenticated. After receiving a valid activation key from the endoscope (100), the system may provide automated image analysis or other features to that endoscope (100) for a period of time, or during a particular usage session. In some implementations, the activation key may be limited to a single use or a small number of uses, such that subsequent uses of the endoscope sheath (102) with the endoscope (100) may be denied use of the automated image analysis feature.

Such limitations may be enforced by data stored on the endoscope sheath (102), image processor (104), or remote server (106) indicating that the particular activation key has already been used or is otherwise expired or invalid, which data may be written to those devices after a prior use of the activation key. As another example, the activation key may be stored as a read-once portion of memory on a memory chip of the endoscope sheath (102), such that the data is no longer stored or available on the chip after the first time it is accessed. As another example, the activation key may be stored on a memory chip that is damaged or destroyed by the act of decoupling the endoscope sheath (102) from the endoscope (100), or locking the endoscope sheath (102) to the endoscope (100).

In some implementations, the endoscope sheath (102) may receive and store on a memory chip operational details from a procedure performed with the endoscope (100), which may include results of image analysis, error codes, images and video, and other information as has been described. Since the endoscope sheath (102) is removable and replaceable, it may be provided to a patient, medical practitioner, or technical support personnel after a procedure where such party desires access to information written to the memory chip as a result of the procedure. Such information may be accessed by coupling the endoscope sheath (102) to the user device (108) or another device and copying the desired information from the memory chip. Such coupling may be, for example, wireless (e.g., Bluetooth, NFC, RFID), or may be a direct coupling (e.g., USB, or other direct data connection such as a proprietary connection that couples to an adapter or dongle capable of USB connection).

In this manner, patients may retain images and/or analysis results from a procedure for their own use, practitioners may retain the same for further review, diagnosis, or treatment, and technical support personnel may access and review error codes or performance data usable to address errors and improve the system. Information stored on the endoscope sheath (102) may be encrypted and/or otherwise protected from casual access. In this manner, sensitive and proprietary information may be securely and readily exchanged by physical exchange of the endoscope sheath (102), which may alleviate concerns over cloud-based transmission and storage of the information, or the potential for loss of data when the procedure is performed in an "offline" setting where such information cannot be readily transmitted to the remote server (106) or another location.

Another example of information stored on one or more memory chips of the endoscope sheath (102) include specific procedural information, such that a particular sheath may be configured to be used for a particular procedure. As an example, one endoscope sheath (102) may be configured for analysis of a nasal obstructive airflow, and when coupled to the endoscope (102) and in communication with the image processor (104), the stored information may be used to automatically initiate the software of the image processor (104) for this particular disease (e.g., the graphical user interface, device settings, software settings, and automated image analysis type may be determined and loaded automatically based on the received information once the endoscope sheath (102) is attached).

The image processor (104) may be, for example, a computer, tablet device, or other computing device having capabilities such as a display, touch sensitive surface, buttons, processor, memory, communication devices (e.g., Wi-Fi, Bluetooth, USB, Ethernet, or other wireless or wired data interface), and other features. The image processor (104) may be configured with software allowing for offline image capture and image analysis, or may be configured to access such software at the remote server (106) or another location when connected to the internet via a cellular network or other channel. The image processor (104) may also be configured with software for managing the performance of the endoscope (100), and may adjust and control image resolution, framerate, and other characteristics of image capture, as well as the output and characteristics of light provided by LEDs, laser light emitters, or other devices of the endoscope (100), as will be described in more detail below. As an example, the image processor (104) may automatically adjust the output of one or more LED lights at a distal tip of the endoscope (100) based upon captured images, in order to automatically adjust the level of light in real-time during imaging.

The user device (108) may be, for example, a computer, tablet device, smartphone, or other computing device capable of exchanging, manipulating, and storing data, and including a processor, memory, storage device, communication device, and other components. The remote server (106) may include one or more physical servers, virtual servers, cloud servers, remote servers, or other computing environments, with each server having processors, memory devices, communication devices, and other components as may be required to exchange, manipulate, and store data.

While the system of FIG. 1 shows the endoscope sheath (102), endoscope (100), and image processor (104), it should be understood that other medical instruments and related devices may be used in varying implementations. As an example, a sheath configured for use with a balloon dilation driver may have some or all of the features described in the context of FIG. 1, but may be coupled to an inflation (e.g., fluid or gas) source or other device instead of the imaging processor (104). As another example, a sheath configured for use with a sonic ablation device may be coupled to a power source or sonic pulse generator instead of the imaging processor (104). As further example, each of the above examples may also include an endoscopic tip usable in conjunction with the balloon dilation feature or tissue ablation feature, and so may include the image processor (104) in addition to sources for inflation, sonic pulse generation, irrigation, vacuum, or other features, as will be described in more detail below.

Figure 2:
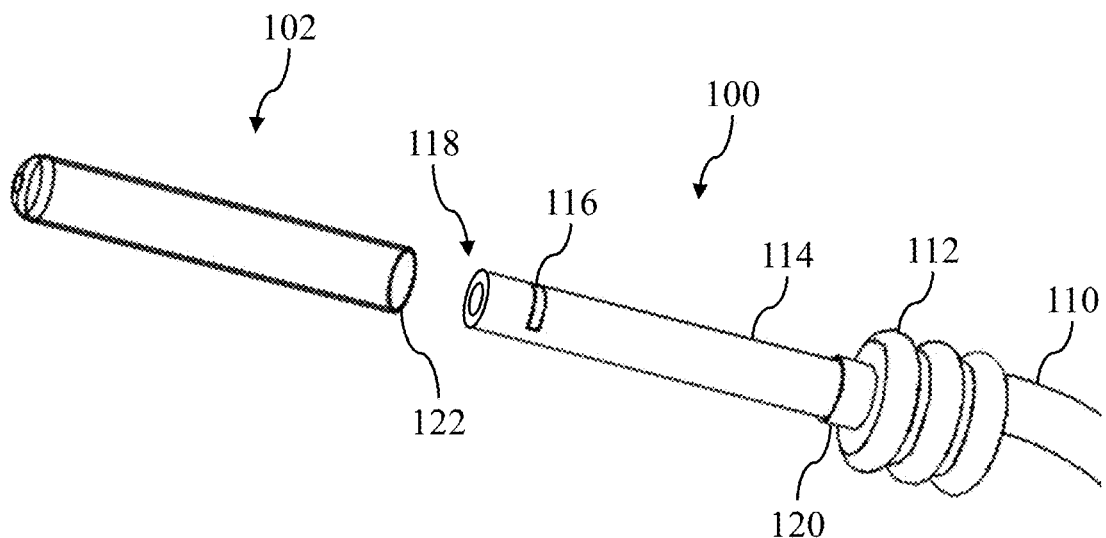
FIG. 2 is a perspective view of an exemplary endoscope and an exemplary endoscope sheath.

FIG. 2 is a perspective view of the endoscope (100) and endoscope sheath (102) prior to installation of the sheath. The endoscope (100) includes a handle (112) that may include one or more controls usable to provide inputs to the image processor (104) to control the behavior of the endoscope (100) and any associated software applications or user interfaces. As an example, the handle (112) may include a touch sensitive surface that may receive pressing, sliding, pinching, or other touch inputs, or may include buttons, switches, paddles, dials, scroll wheels, or other input controls. User inputs may be control specific (e.g., a button press that causes a the current endoscope image to be captured and saved to the image processor (104), endoscope sheath (102) or another device) or situational (e.g., a button that may be pressed once to freeze and display the current image via the image processor (104), or pressed twice to release the frozen frame and provide live images). Other features triggered by user inputs via the handle (112) or other controls may include capturing images, capturing video sequences, marking an area of interest in an image or video, marking an area of interest during a procedure timeline log, or marking an area of an image where ablation or other features were used.

A shaft (114) of the endoscope may be rigid or semi-rigid, and may contain cables, circuitry, or other connections that provide power to features at the distal tip (118) of the endoscope, and provide communication of data between features at the distal tip (118) and the image processor (104). In some implementations, such as those where the distal tip (118) includes an ablation feature, balloon dilation and inflation feature, or other capability, the shaft (114) may include channels or connections for such features. The shaft (114) is sized and shaped to receive and couple with the endoscope sheath (102). As an example, an interior of the endoscope sheath (102) may have substantially the same diameter as an exterior of the shaft (114), such that a friction fit is achieved during coupling. Retention of the endoscope sheath (102) once installed may be aided by high friction material included on the shaft (114), such as textured rubber surfaces that are slightly compressed by the endoscope sheath (102) during installation. The length of the shaft (114) will also correspond to the length of the endoscope sheath (102), and each may correspond to an intended purpose for that particular implementation (e.g., the shaft (114) will have varying lengths for use with ENT procedures, and may have different lengths for use with arthroscopic procedures) such that the handle (112) does not contact the treatment site, the entire shaft (114) is covered by the sterile barrier of the endoscope sheath (102), and only the endoscope sheath (102) contacts the treatment site.

In some implementations, the interior of the endoscope sheath (102) will have a length substantially the same as, or slightly longer than, the shaft (114) when the sheath is installed against a sheath receiver (120). In some implementations, the endoscope sheath (102) will be of a length that is substantially longer than the shaft (114). The sheath receiver (120) may be a flat surface that the proximal open edge (122) of the endoscope sheath (102) meets and rests against during installation (e.g., show more clearly in FIG. 6). In some implementations, the sheath receiver (120) may include a magnetic feature or friction fit feature to aid in retention of the sheath (102) after installation. In some implementations, the sheath receiver (120) may include a slot that the proximal open edge (122) of the endoscope sheath (102) slides into during installation. In such implementations, the sheath receiver (120) may further include a locking feature whereby a mechanical tab or key may be pressed into a corresponding slot at the proximal end of the endoscope sheath (102) to mechanically retain its position. The sheath receiver (120) may further include mechanical feature such as key-and-slot features to aid in achieving a proper rotational fit of the endoscope sheath (102) on the shaft (114), which may aid in aligning electrical connections, data connections, or other resource connections between the endoscope (100) and the endoscope sheath (102), as will be described in more detail below.

A sensor module (116) is integrated with the shaft (104), and includes one or more sensor capabilities that are configured to measure characteristics related to a procedure without interference from the endoscope sheath (102). Sensor capabilities of the sensor module (116) may include, for example, pressure sensors, navigation sensors (e.g., tri-axis location trackers usable with a wireless triangulation or magnetic field tracking system, or accelerometer and gyroscopic sensors), temperature sensors, and other sensors. Sensors may be calibrated to provide accurate readings that take into account the thickness and/or resistive properties of the endoscope sheath (102), and the endoscope sheath (102) itself may have a different structure at the position that rests over the sensor module (116) after installation to aid in the function of the sensors. As an example, the endoscope sheath (102) may be constructed of substantially transparent, substantially rigid plastic material, but may have a thinner wall and/or more flexible construction that aligns with the sensor module (116) to allow for a pressure force to be more readily communicated to the sensor module (116) from outside the endoscope sheath (102). Readings from the sensor module (116) may be communicated to the signal processor (104) or other devices, and may be used for general informational purposes, or may be used by automated imaging analysis features, or may be used for other purposes.

Figure 3:
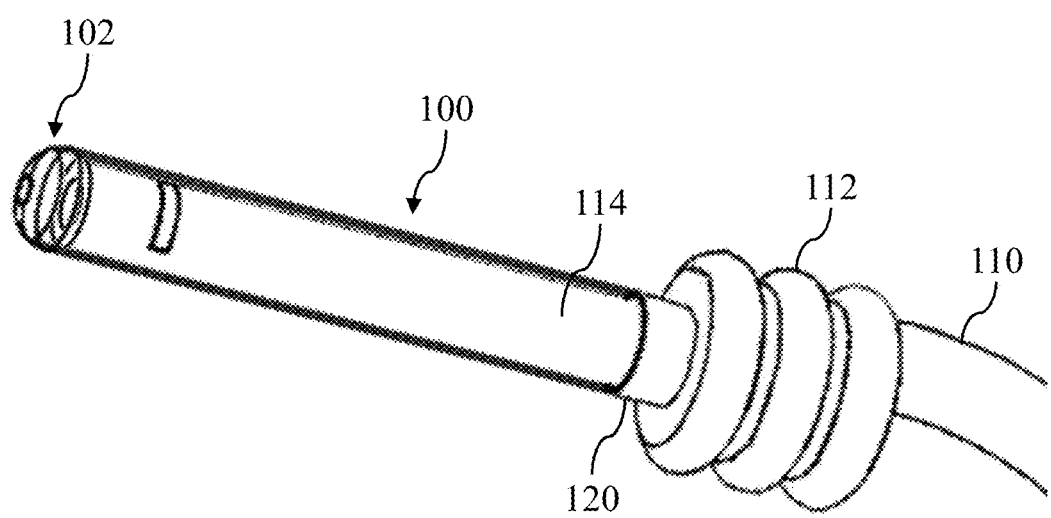
FIG. 3 is a perspective view of the endoscope sheath of FIG. 2 coupled to the endoscope of FIG. 2.

FIG. 3 is a perspective view of the endoscope sheath (102) coupled to the endoscope (100). In that figure, it can be seen that the shaft (114) of the endoscope (100) substantially occupies the interior of the endoscope sheath (102), and that the proximal open edge (122) of the sheath (102) rests against the sheath receiver (120), such that no portion of the shaft (114) may come into contact with the patient at the treatment site.

Figure 4:
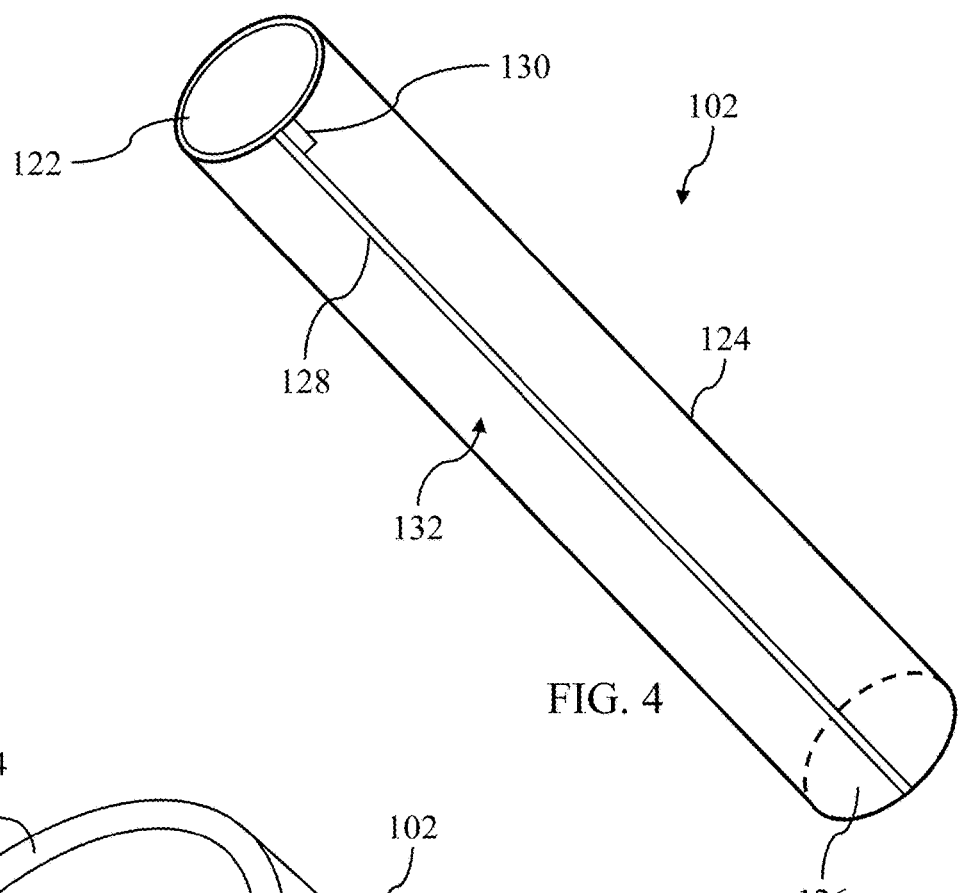
FIG. 4 is a perspective view of the endoscope sheath of FIG. 2.

FIG. 4 is a perspective view of the endoscope sheath (102), viewed from the proximal opening (122) that receives the endoscope (100). A body (124) of the sheath defines an interior (132) that is configured to receive the shaft (114) of the endoscope (100). A lens or optical interface (126) at the distal end of the endoscope sheath (102), opposite the proximal opening (122), may include materials or components with varying optical properties. The lens or optical interface (126) may be, for example, a substantially transparent plastic that is also used for the body (124), or a substantially transparent glass that is sealed into the body (124) to maintain a sterile barrier. The lens or optical interface (126) may be flat and/or non-disruptive in that it does not substantially alter the light passing through to the interior (132), or may have varying shapes and/or optical properties depending upon a particular implementation.

Optical characteristics or components of the lens may include, for example, a fish-eye view, macro view, wide angle view, magnified view, plano convex lens, plano concave lens, bi-convex lens, bi-concave lens, positive meniscus lens, and negative meniscus lens. The lens (126) may also be configured to diffuse LED light projected from the distal tip (118) of the endoscope (100) to provide a more ambient illumination rather than a focused beam, and such diffusion materials may be positioned to diffuse LED light without influencing images captured by a camera at the distal tip (118). The lens (126) and/or body (124) may also be configured to provide differing viewing angles for a camera at the distal tip (118), such that a single endoscope (100) may be fitted with different sheaths (102) to provide different viewing angles of the treatment site, such as 30, 45, and 70 degree angled scopes for example. The lens (126) may also be configured to filter certain types of light, or configured to filter portions of the resultant image to provide a narrower field of view.

Lens (126) capabilities and properties may be selected for different types of endoscope sheaths (102) to aid in image capture, and to provide images that may be readily analyzed by an automated image analyses process, such as that disclosed herein. For example, one implementation of the endoscope sheath (102) intended for imaging of the turbinate may have an angled lens that focuses the view on the anticipated position of the turbinate, and that includes opaque filters that obfuscate the anticipated position of the septum. A different implementation of the endoscope sheath (102) intended for imaging of the entire nasal canal may include a wide-angle lens that can capture a large field of view with no obfuscation. Since each sheath (102) may include a memory chip that contains data for pre-configuring a software application of the image processor (104) for specific procedures, changing between sheaths with purpose specific lenses may also cause the image processor (104) to automatically configure and prepare a corresponding software interface for the specific purpose.

Figure 5:
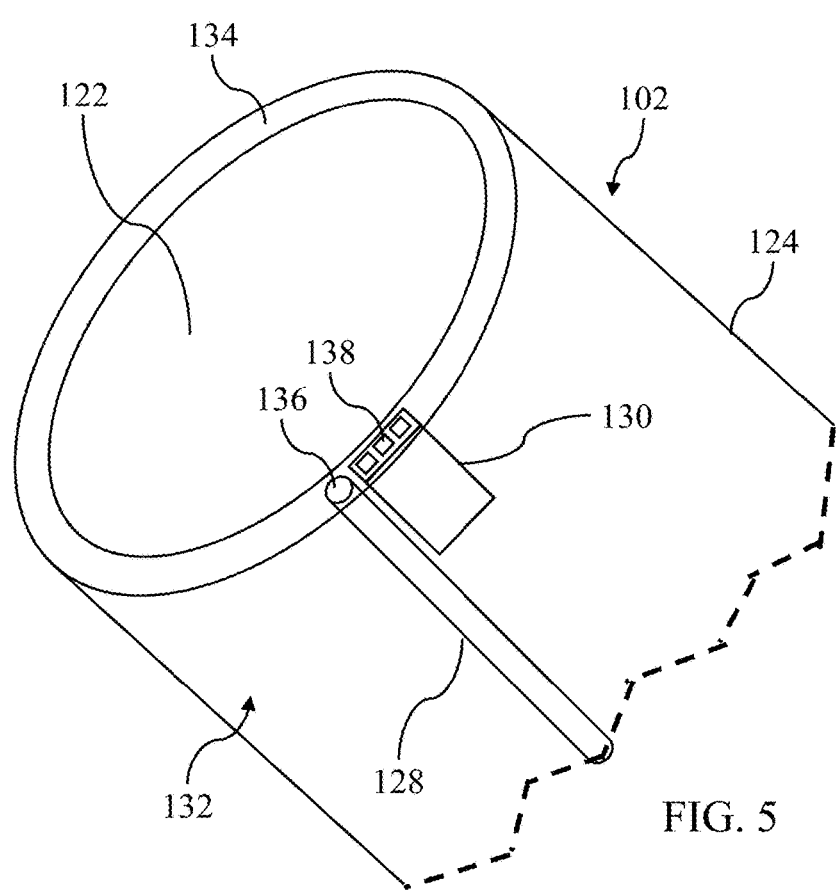
FIG. 5 is a perspective view of the endoscope sheath of FIG. 2, magnified on an open end of the endoscope sheath.

The sheath (102) also includes a channel (128) and a sheath memory (130). FIG. 5 is a perspective view of the endoscope sheath of FIG. 2, magnified on the proximal opening (122) of the endoscope sheath and more clearly showing the channel (128) and the sheath memory (130). The channel (128) runs the entire length of the endoscope sheath (102), beginning with a channel opening (136) within a rim (134) of the body (124) and terminating near the lens (126). The termination of the channel (128) will vary be implementation, but may include, for example, an opening through which irrigation fluid may be provided, in which case the channel (128) would provide fluid transmission, or an electrode that may be energized to ablate tissue, in which case the channel (128) would contain a power cable or wire for electrical transmission.

The sheath memory (130) is also shown embedded in a sidewall of the body (124), with a set of connectors (138) exposed at the rim (134). The connectors (138) may be, for example, conductive electrical connections through which electric signals can be transmitted to provide power and/or the exchange of data between the sheath memory (130) and the endoscope (100), as has been described. While the channel (128) and sheath memory (130) are each shown embedded within a sidewall of the endoscope sheath (102), this disclosure also contemplates that they may be mounted within the interior (132), or may be mounted on the exterior of the body (124), as may be desirable in varying implementations.

Figure 6:
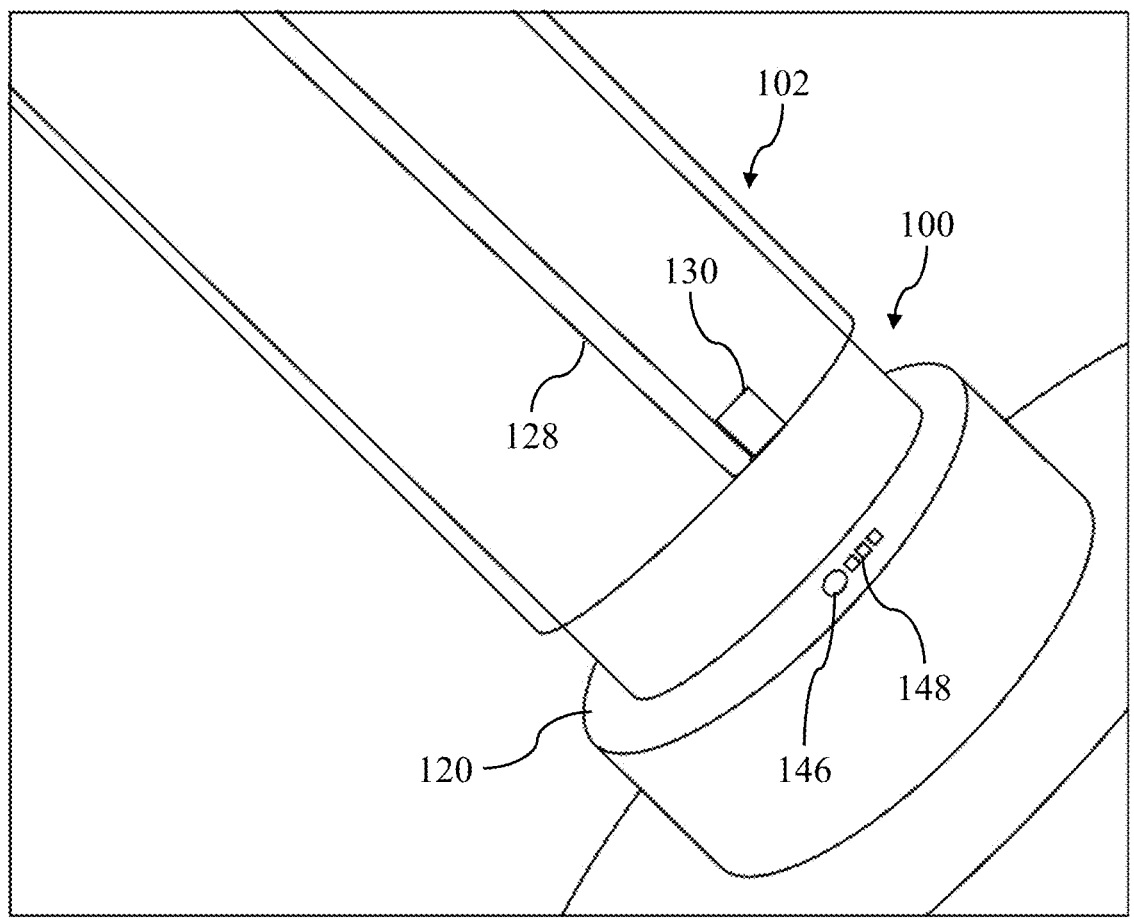
FIG. 6 is a perspective view of a proximal end of the endoscope sheath of FIG. 2 during coupling with the endoscope.

FIG. 6 is a perspective view of the proximal opening (122) of the endoscope sheath (102) during coupling with the endoscope (100). The sheath memory (130) and the channel (128) are shown in alignment with a corresponding channel coupling (146) on the surface of the sheath receiver (120), such that when the sheath (102) is fully installed the channel (128) and channel opening (136) will align with the channel coupling (146). In implementations where the channel (128) provides irrigation fluid to the distal tip, the channel coupling (146) may achieve a substantially impermeable seal against the channel opening (136) such that an irrigation fluid or liquid drug may be provided via the channel coupling (146) based upon a user input, and delivered to the distal tip (118) via the channel (128). Where the channel (128) contains an electrical coupling for an ablation electrode or other device at the distal tip (118), the channel coupling may include a conductive pad that contacts a corresponding conductive element within the channel opening (136) and achieves an electrical connection. It can be similarly seen that the set of connectors (138) will align with a connector coupling (148) on the surface of the sheath receiver (120), achieving an electrical connection and allowing for the exchange of electrical signals between the endoscope (100) and the sheath memory (130).

Figure 7:
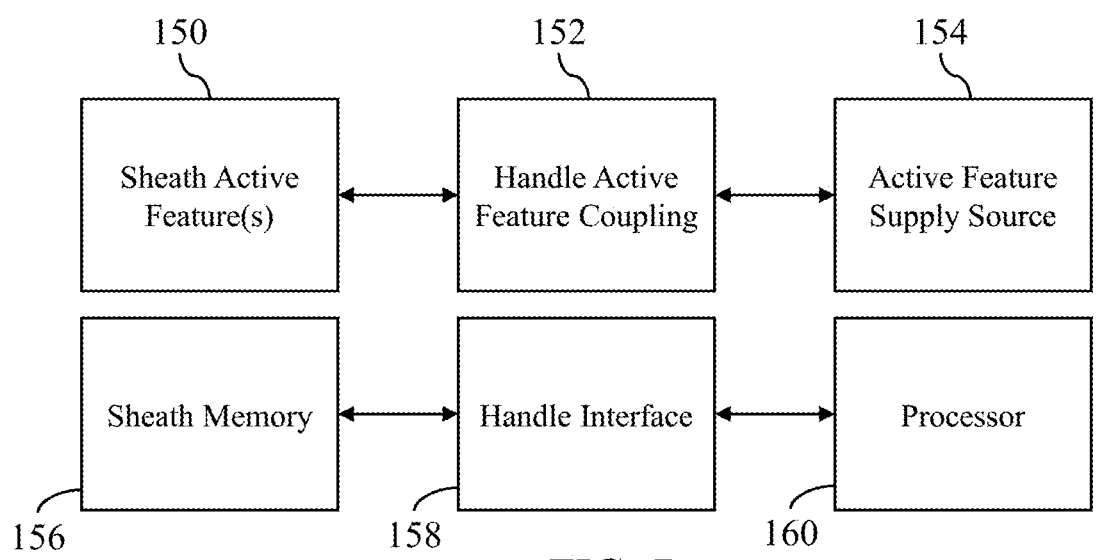
FIG. 7 is a schematic diagram illustrating functional characteristics of an endoscope sheath.

FIG. 7 is a schematic diagram illustrating the functional characteristics of an endoscope sheath such as the endoscope sheath (102) described above. The sheath may contain one or more active features (150) (e.g., irrigation, electrode ablation, drug delivery, balloon inflation, etc.) that are enabled when the sheath is coupled to a corresponding medical instrument (152), such as the endoscope (100). The resource or other condition required by the active feature can then be provided via the coupled medical instrument (154). This may include, for example, ablation power delivered from a generator, irrigation fluid delivered from an irrigation source, inflation delivered from an inflation source, and other delivery sources.

The sheath also includes a sheath memory (156) that couples to a memory coupling (158) of the medical instrument to allow for the exchange of data, as has been previously described. A processor (160) of the medical instrument, or an attached device such as the image processor (104), may access or receive data from the sheath memory (156), and may also write data to the sheath memory (156), as has been described. Based upon the diagram of FIG. 7, it can be seen that the medical device primarily acts as a pass-through for data, irrigation, or other features, which are achieved via connections such as that described above in the context of FIG. 6, in order to preserve the sterile barrier provided by the endoscopic sheath.

Figure 8:
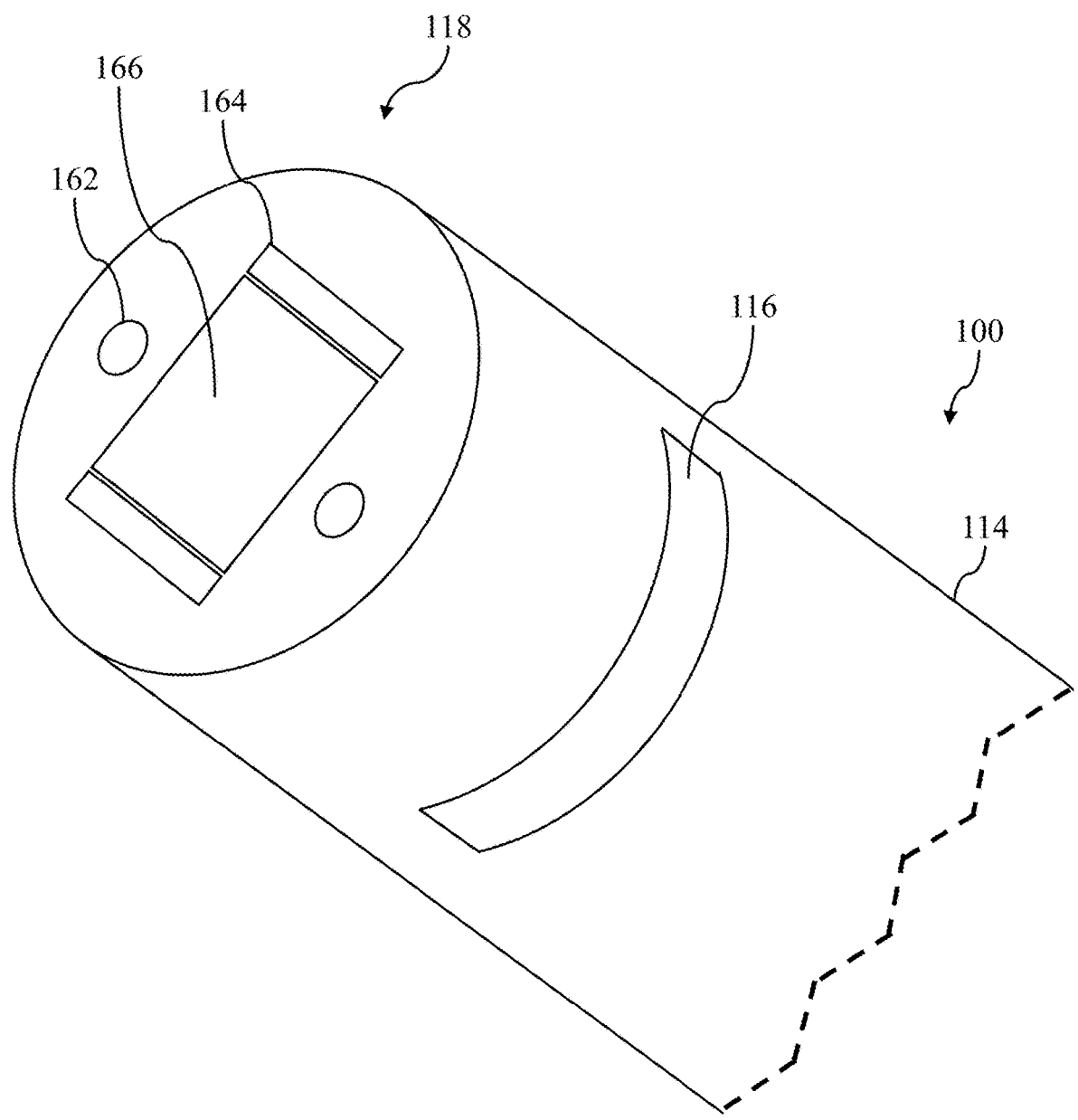
FIG. 8 is a perspective view of a distal tip of the endoscope of FIG. 2.

FIG. 8 is a perspective view of the distal tip (118) of the endoscope (100). The distal tip (118) includes one or more cameras (166) configured to capture images of patient anatomy, and transmit captured image data to the image processor (104) or another device. One or more light sources (164) may be LEDs or other illuminators, and may be selectively illuminated (e.g., with varying color, intensity, or sequence of lighting) based upon control signals from the image processor (104) or another device (e.g., such as manual input controls of the endoscope (100) itself). One or more laser emitters (162) may be arranged on the distal tip (118) with parallel optical axes, or orthogonal optical axes, and may be selectively activated (e.g., with varying intensity, sequence, or other characteristics) based upon control signals from the image processor (104) or another device. The light sources (164) may be configured to provide optimal lighting during procedures, and may operate on a feedback loop based upon captured images (e.g., where image glare or reflected light harms image quality, the light sources (164) may be re-configured for subsequent images to reduce glare). The laser emitters (162) may be used to provide range, depth, or scale indicators that are visible within images captured by the camera (166), and that may be used during image analysis to determine the depth or scale of portions of captured images, as has been described.

In some implementations, there may be an open space between the distal tip (118) and the endoscope sheath (102), while in others the lens (126) portion of the endoscope sheath (102) may be in direct contact with some or all of the features of the distal tip (118). As an example, a portion of the lens (126) may directly contact the camera (166) in order to provide a seamless optical transmission between the lens (126) and the camera (166). As another example, a portion of the lens (126) may contact the light sources (164) and filter, diffuse, focus, or otherwise modify the transmission of light through the lens (126). As yet another example, a portion of the lens (126) may contact the laser emitters (162) to change the angle of laser light transmission (e.g., a pair of emitted lasers with parallel optical axes may be modified to have orthogonal optical axes, such that they overlap at a pre-determined distance of projection that is relevant to a particular procedure), or to diffuse the projected laser light into a pattern or other focal point that may be usable to determine range, depth, topography, or other features of a target surface.

Figure 9A:
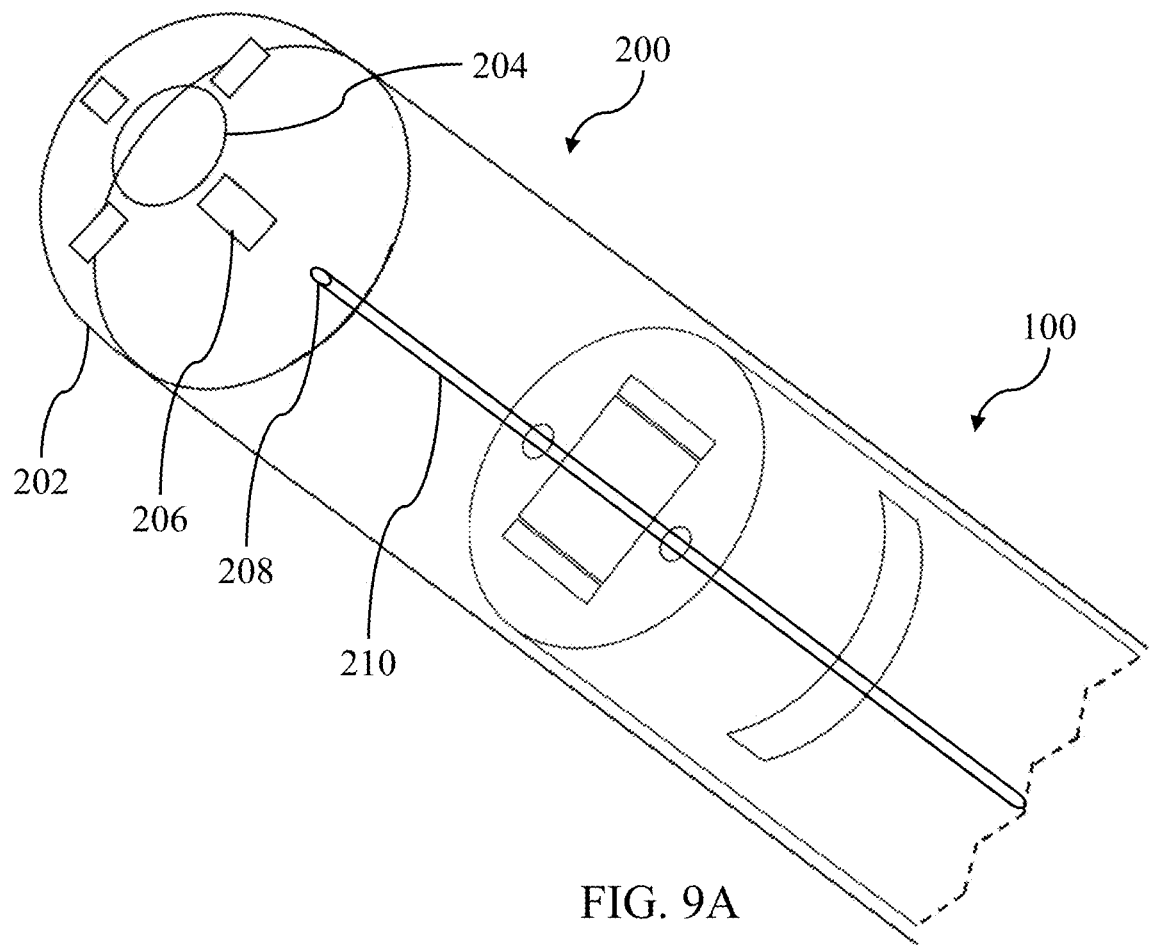
FIG. 9A is a front perspective view of a distal tip of the endoscope of FIG. 2 with an exemplary ablation sheath.

While the endoscope sheath (102) has been discussed above in some detail, it should be understood that varying types of endoscope sheaths may be implemented based upon some or all of the concepts discussed in relation to the endoscope sheath (102) and the schematic diagram of FIG. 7. As an example, FIG. 9A is a front perspective view of a distal tip of the endoscope (100) coupled with an ablation sheath (200). The ablation sheath (200) may include some or all of the characteristics of the endoscope sheath (102), and may be formed from substantially translucent plastics, glasses, or both. As with any other sheath disclosed herein, the ablation sheath (200) is configured to provide a sterile barrier between a medical instrument (e.g., the endoscope (100)) and a treatment site. As with any other sheath disclosed herein, the ablation sheath (200) may include a sheath memory that provides access and pre-configuration of software, stores information related to a procedure, and provides other functions, as has been previously described.

The ablation sheath (200) includes one or more channels (210) for transferring fluid from a source at the proximal end of the ablation sheath (200), to one or more fluid outlets (208) at the distal end of the ablation sheath (200). Each fluid outlet (208) may have a dedicated channel that is directly coupled to a fluidic connection in the endoscope (100) or other medical instrument on a one-to-one basis, or the ablation sheath (200) may include a manifold to distribute fluid from a single source or connection to a plurality of fluid outlets (208). The distal end of the ablation sheath (200) includes a rounded convex tip (202) where the fluid outlets (208) are located. Fluid provided via the fluid outlets may include saline or other irrigation fluids for irrigating a treatment site and/or the convex tip (202) itself, and may also be used to provide liquid carrying drugs or substances related to treatment to the treatment site. A lens (204) is positioned substantially centrally in the convex tip (202), and may have some or all of the characteristic of other lenses described herein (e.g., such as the lens (126)). In some implementations, the entirety of the convex tip (202) may be considered part of the lens (204) for viewing and imaging purposes. Fluid may be provided via the fluid outlets (208) manually based upon user inputs to clear the lens (204) of blood, tissue, or other contaminants, or may be provided automatically where analysis of images captured by the endoscope (100) indicate that the lens is obstructed by blood or tissue. The fluid outlets (208) may include hoods or other fluid diverters to direct irrigation fluid towards the lens (204) or in other directions.

The tip (202) also includes one or more electrodes (206) positioned on an exterior surface where they may come into contact with tissue at a treatment site. Electrodes may be biopolar or monopolar, and can be used to transmit reversible electroporation for drug delivery, or irreversible electroporation for tissue ablation. Power may be provided to the one or more electrodes (206) to ablate tissue during a procedure, and may be provided via a channel within the ablation sheath (200) that contains a wire coupling the one or more electrodes (206) to a power source of the coupled medical instrument or another device, such as a surgical generator. When the ablation sheath (200) is coupled to the endoscope (100) or another medical instrument, fluidic, electric, and data connections may be completed, as has been previously described (e.g., such as in the context of FIG. 6). The channel (208) and/or fluid outlets (208) may each include unidirectional valves or seals that allow fluid to be provided while preventing backflow, thus preserving the sterile barrier.

Figure 9B:
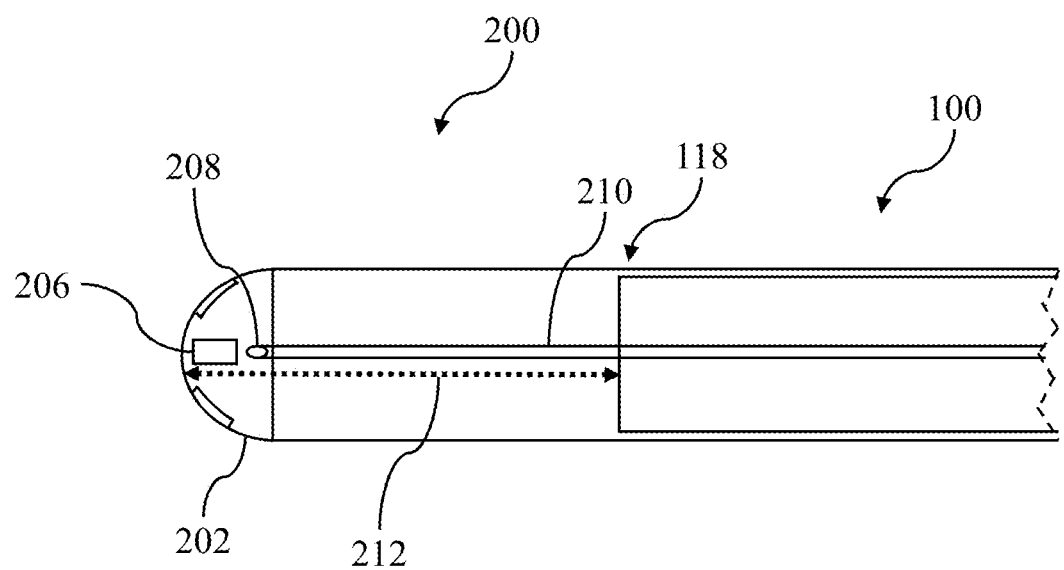
FIG. 9B is a side elevation view of a distal tip of the endoscope of FIG. 2 with the ablation sheath of FIG. 9A.

As can be seen in FIG. 9B, the ablation sheath (200) is of a length that there is a distance (212) separating the distal tip (118) of the endoscope (100) from the tip (202) of the ablation sheath (200) after it is firmly installed. As a result of this offset, images captured by the endoscope (100) may be from an offset perspective relative to the tip (202) through which anatomy is viewed, and will also include the one or more electrodes (206). As an example, FIG. 9D shows an image illustrating the field of view captured by the endoscope (100) when paired with the ablation sheath (200). An image (230) of the anatomy is shown, with a reticle (232) formed by the pattern of electrodes (206). In this manner, the tip (202) may be placed into contact with tissue, such that activation of the electrodes (206) will cause ablation of the tissue, and the endoscope (100) will continue to provides images of the treatment site that will also include the reticle (232) indicating the area where tissue ablation will occur. The distance (212) may be adjusted to increase/decrease the relative size of the reticle (232), as may be desired for a particular implementation of the ablation sheath (200).

Figure 9C:
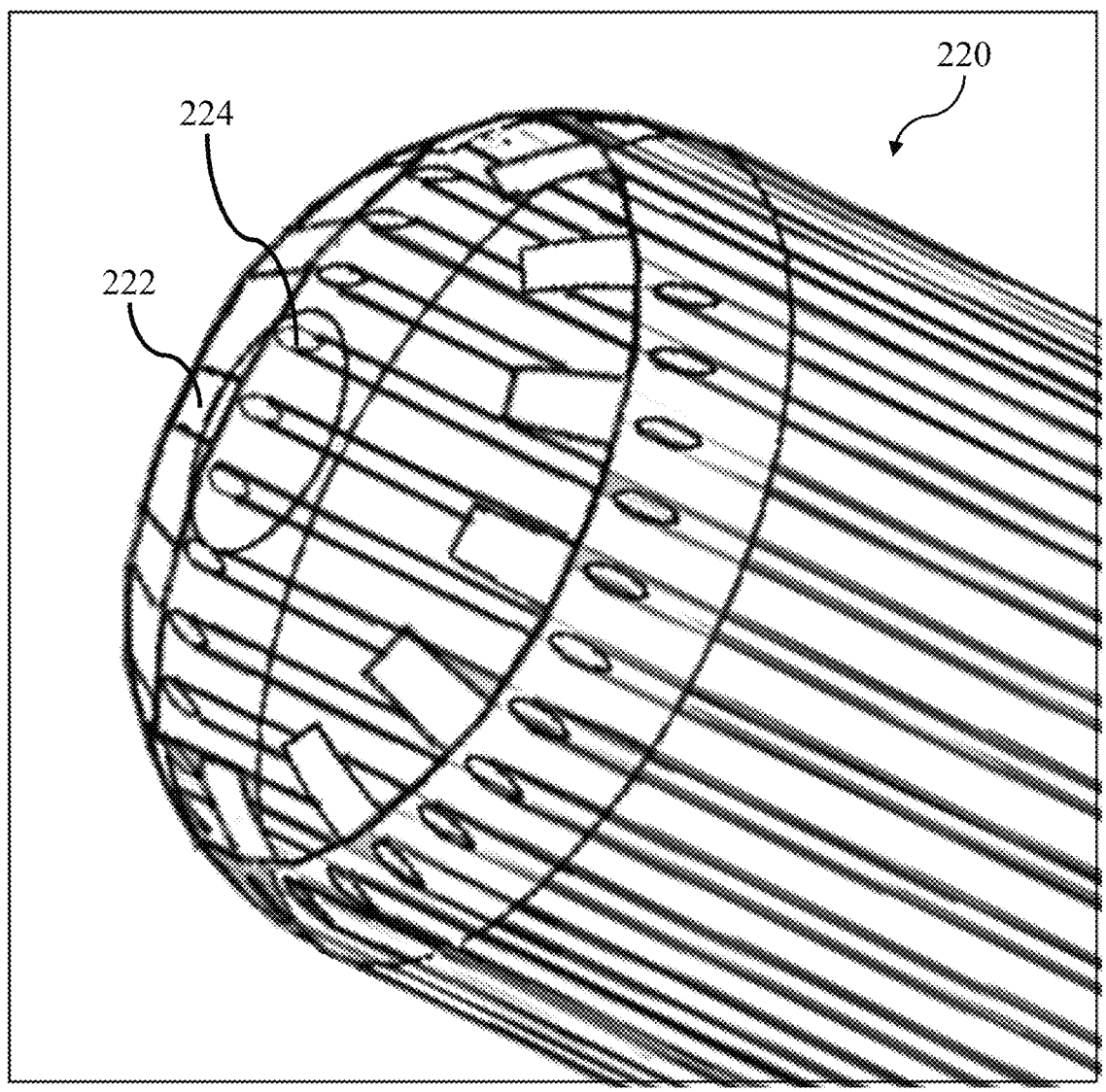
FIG. 9C is a perspective view of another ablation sheath usable with the endoscope of FIG. 2, which includes channel outputs for irrigation and/or drug delivery.
Figure 9D:
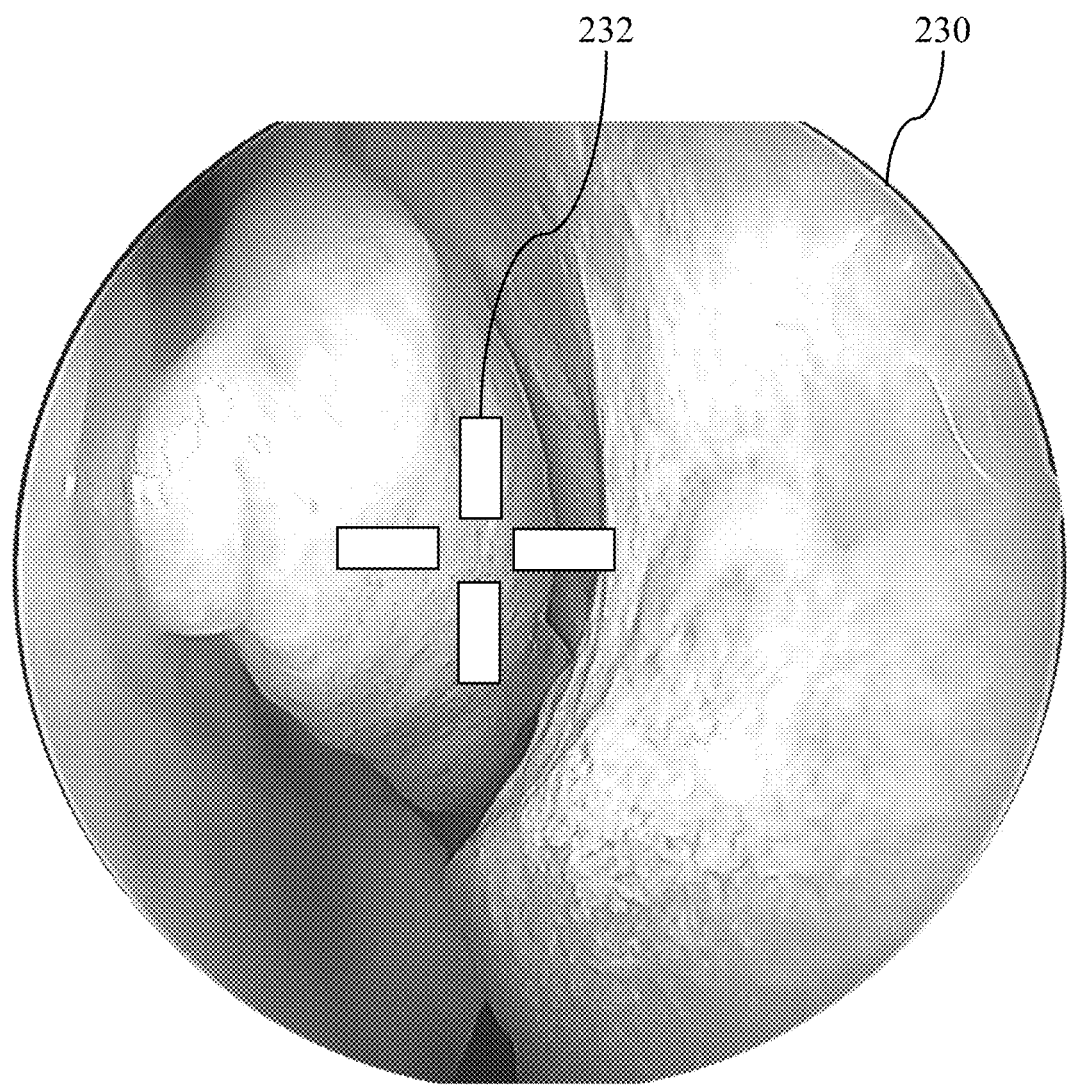
FIG. 9D is a schematic diagram illustrating an exemplary interface for viewing patient anatomy with an ablation reticle.

FIG. 9C is a perspective view of another ablation sheath (220) usable with the endoscope (100) or other medical instruments. The ablation sheath (220) of FIG. 9C is similar to the ablation sheath (200) previously described, but includes a plurality of irrigation outlets (224) distributed around the entire circumference of the tip (202), as well as an increased plurality of electrodes (224) that are also distributed around the circumference of the tip (202). As illustrated in FIG. 9C, implementations of an ablation sheath may have varying numbers of irrigation outlets (224) (e.g., between 1 and about 30, or more depending upon the size of the tip (202) and the size of each outlet (224), and varying numbers of electrodes (222) (e.g., between 1 and about 20, or more depending upon the size of the tip (202) and the size of each electrode (222)). The irrigation outlets can be used for drug and other agents delivery, and furthermore these drugs and/or other agents can be used in sync with the ablation elements to accelerate the absorption of the drug, such as when the elements are used to deliver reversible electroporation enabling the cell pores to open up so the drugs and/or other agents are absorbed quicker than without this feature.

In some implementations of an ablation sheath, such as the ablation sheath (200) of FIG. 9B, a length of the distal end of the sheath that may be less than or equal to the distance (212) may include a flexible sidewall, and/or a flexible biasing member such as a spring, that will allow that portion to flex away from a neutral position as the ablation sheath is pressed against tissue, which allows the tip (202) and electrodes (206) achieve full contact with a target tissue without requiring reorientation of the endoscope (100) itself, resulting in more stable and predictable delivery of energy to the tissue. As the tip (202) is pulled away from the target tissue, the flexibly biased portion will return to a neutral position, allowing for extraction of the endoscope (100) and sheath, or allowing for re-deployment and tissue ablation at another location within the patient. Some implementations of an ablation sheath and endoscope, such as the endoscope (100), may include a strain gauge or force sensor that detects a level of force applied to the target tissue by the tip of the ablation sheath.

As an example, with reference to FIG. 3, the sheath receiver (120) may include a force sensor that detects a force transmitted through the coupled sheath during use (e.g., little or no force during navigation of the endoscope, or a varying degree of force as the tip of the sheath is compressed against a target tissue to prepare for ablation). Such information may be displayed via the image processor (104) or another device, which may be configured to provide alerts based on insufficient or excessive force readings, or may be configured to allow/disallow an ablation function based on sufficient or insufficient force readings (e.g., a low force reading may prevent ablation, as it may indicate a poor contact between the electrodes and the target tissue).

Figure 10A:
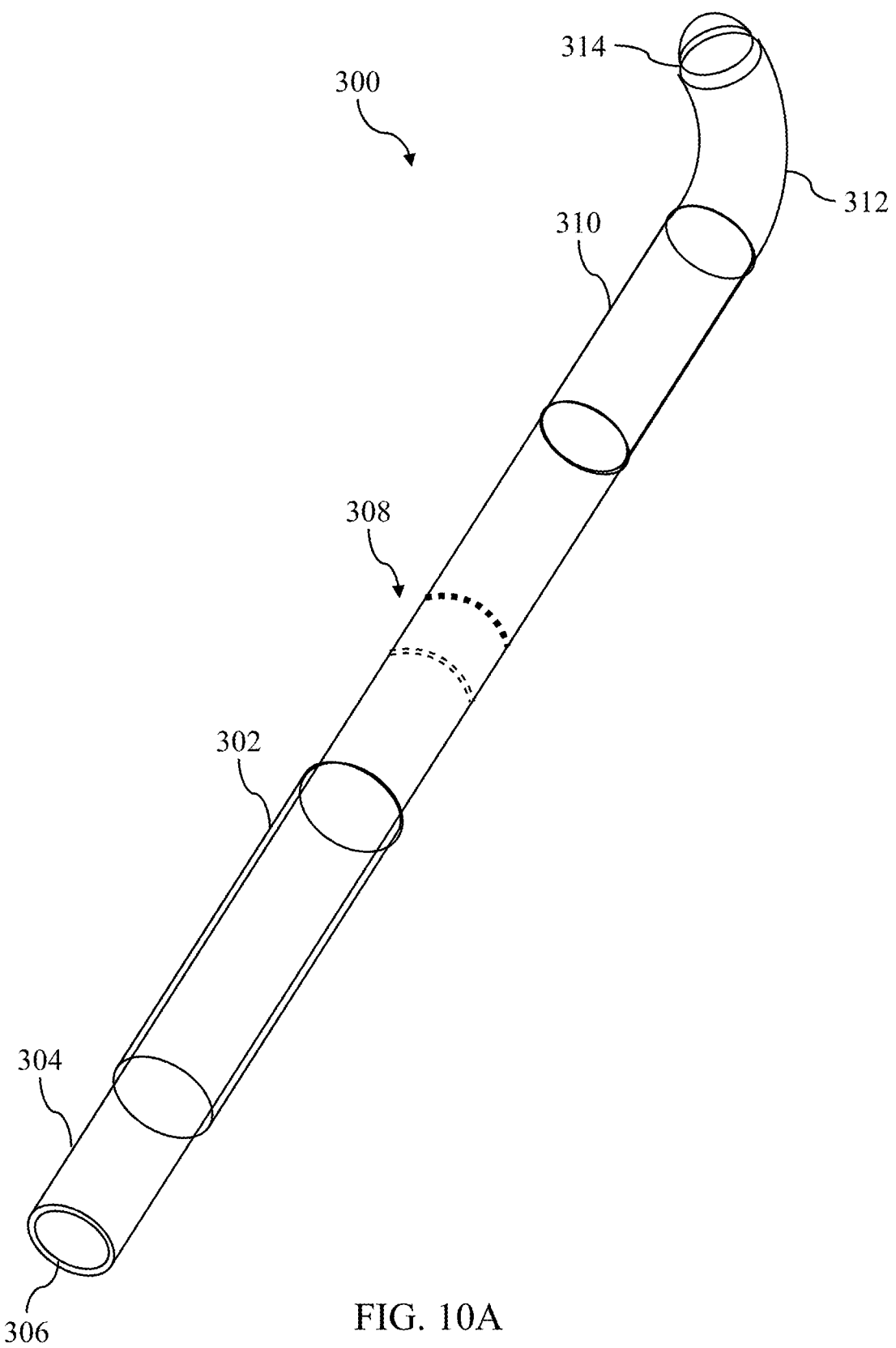
FIG. 10A is a front perspective view of an exemplary balloon dilation sheath.

As another example of a functional sheath and medical instrument implementation in accordance with this disclosure, FIG. 10A is a front perspective view of a balloon dilation sheath (300). Varying implementations of the balloon dilation sheath (300) may include some or all of the features disclosed in relation to the endoscope sheath (100) or other sheaths, as well as the schematic diagram of FIG. 7. For the avoidance of doubt, it should be understood that the ablation sheath (300) may include a sheath memory, channels for irrigation or fluid delivery, power delivery, or other features, and may be configured to couple such features with a corresponding coupling of the medical instrument upon installation (e.g., such as described in FIG. 6) via a rim (306) of the sheath.

Figure 10B:
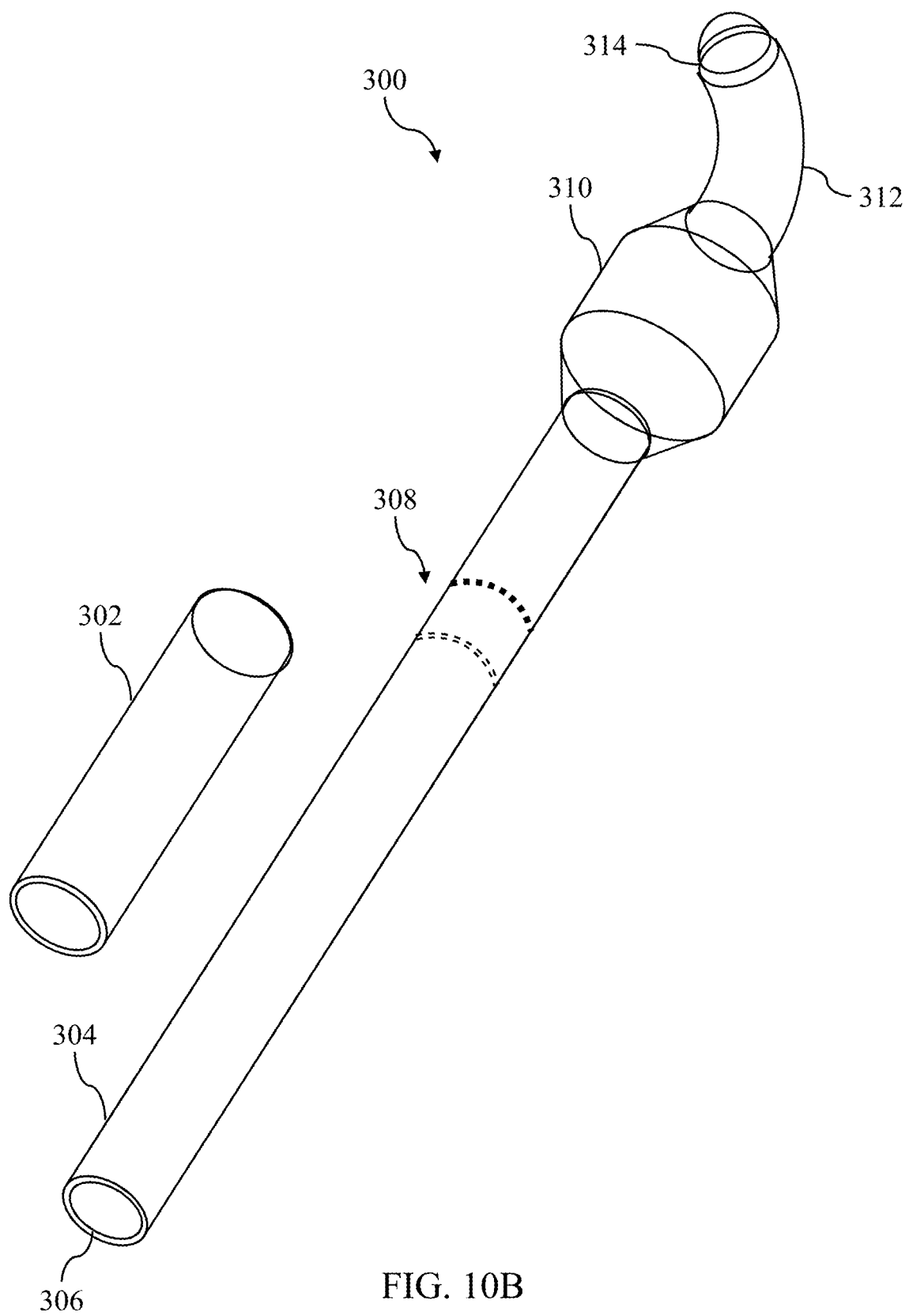
FIG. 10B is a front perspective view of the balloon dilation sheath of FIG. 10A with an exemplary inner sheath removed from an exemplary outer sheath, and an expanded balloon portion.
Figure 11A:
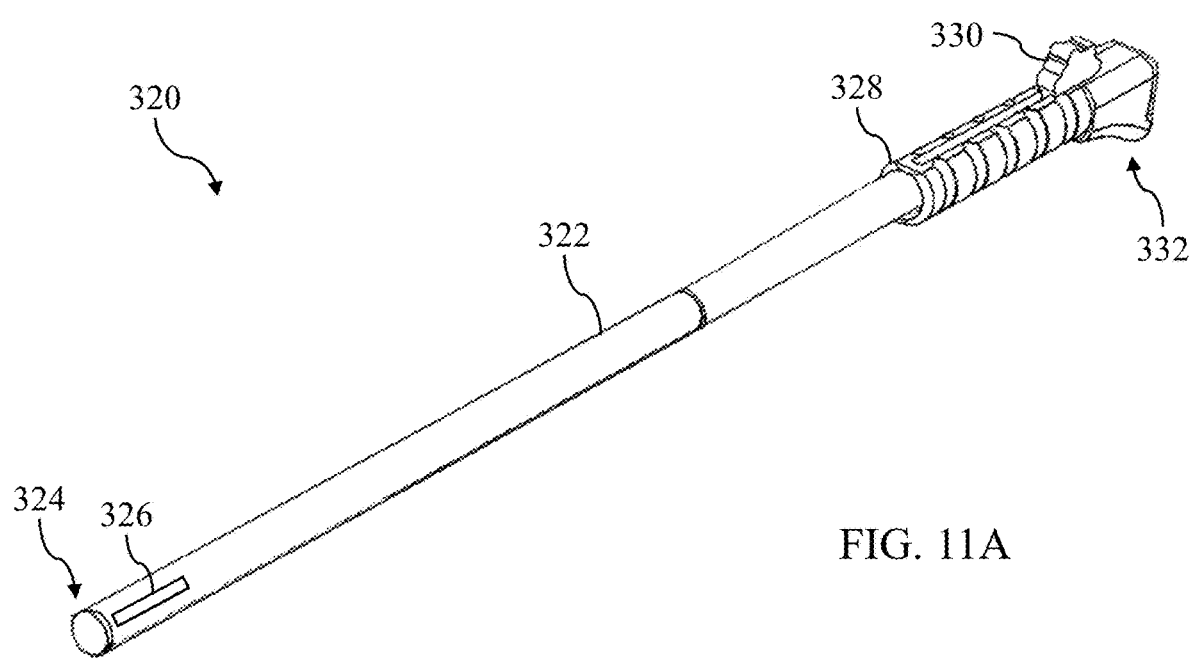
FIG. 11A is a front perspective view of an exemplary driver usable with the balloon dilation sheath of FIG. 10A.

The balloon dilation sheath (300) may be usable with a driver (e.g., such as the driver (320) shown in FIG. 11A) or other medical instrument during a balloon sinuplasty procedure. The balloon dilation sheath (300) includes an outer sheath (302) that statically couples with the driver (320), and an inner sheath (304) that is slidably positioned within the outer sheath (302). Operation of the driver (320) may cause the inner sheath (304) to extend and retract while the outer sheath (302) remains in a fixed position. This arrangement maintains the sterile barrier between the driver (320) and the treatment site, as the only portions of the inner sheath (304) that may come into contact with the treatment site will be confined within the length of the outer sheath (304), and so there can be no contamination of the driver (320) itself during use. FIG. 10B shows the outer sheath (302) removed from the inner sheath (304).

The balloon dilation sheath (300) may also include one or more depth markings (308) at varying positions along its length, which may be used to aid in insertion and positioning of the distal end of the sheath during a procedure. Each depth marking (308) may be visually distinct, and may indicate a shallow insertion, a sufficient insertion, a dangerously deep insertion, and so on.

The balloon dilation sheath (300) also includes a balloon (310), which may be formed from the sidewall of the balloon dilation sheath (300) itself, or may be a separate sheath or piece surrounding the inner sheath (304) that is in fluid communication with the inner sheath (304), while being sealed against the exterior to preserve the sterile barrier. The balloon (310) may be inflated by delivery of a liquid via the driver (320) or via a channel accessible via the rim (306) or sidewall of the sheath (300). As an example with reference to FIG. 11A, the driver (320) may include an inflation slot (326) at a distal end of a shaft (322) that is configured to provide a liquid for inflation of the balloon (310) once it is positioned at a treatment site. Alternatively, a channel of the sheath (300) may achieve a fluid coupling with a corresponding channel of the driver (320) during installation, such that fluid supplied will travel within the channel along the sheath (300) to expand the balloon (310). The balloon (310) will be capable of expanding to varying sizes, and may be confirming such that it will substantially match the shape of the anatomical cavity in which it is inflated. FIG. 10B illustrates the balloon (310) in an inflated state. The inflation source, whether provided by the driver (320) or a channel of the sheath (300) may also be used to extract the liquid and return the balloon (310) to its original size.

While not required, the driver (320) may include a camera, light sources, or other features at a distal tip, as described in relation to the endoscope (100). The balloon dilation sheath (300) may be formed by combinations of plastics, glasses, or other suitable materials, and such materials may be substantially translucent to provide visibility for an integrated camera, or to more generally improve visibility at the treatment site for a separately deployed endoscope, or secondary camera positioned at an offset from the distal end of the driver (320). As one example, the balloon dilation sheath (300) may be formed of semi-rigid plastics, save for the balloon (310), which may be formed of a highly flexible plastic that allows for expansion during inflation.

The balloon dilation sheath (300) may also include a preformed bend (312) at a distal end to aid in navigation of the balloon (310) to the treatment site. The performed bend (312) shown in FIGS. 10A and 10B may aid in navigating to the Eustachian tube, for example. The balloon dilation sheath (300) may also include a bulb shaped tip (314) that includes a rapidly expanding circumference, which may be sized and selected to prevent the distal end of the sheath (300) from being inserted so deeply that it enters the middle ear of a patient.

FIG. 11A shows the driver (320), which may be used with the balloon dilation sheath (300), as has been described. The driver (320) includes a handle (328) with a slider (330) that is operable to advance and extract the inner sheath (304) during deployment of the balloon (310)). A set of connectors (332) on the rear side of the handle (328) may be coupled to a power source (e.g., to power a camera or light source), data source (e.g., to transmit information read from a sheath memory of the sheath (300)), inflation source (e.g., to inflate and deflate the balloon (310)), or other device or resource, depending on the capabilities of the driver (320). A shaft (322) extends from the handle (328) and is sized and shaped to fit within the inner sheath (304) of the balloon dilation sheath (300), as has been previously described.

The shaft (322) may contain channels for electrical, data, or fluid delivery to the distal tip (324) of the shaft (322). An inflation slot (326) is positioned near the distal tip (324), such that an inflation medium (e.g., saline or another fluid) may be delivered via the slot (326) to inflate the balloon (310), and then extracted via the slot (326) to deflate the balloon (310). The inner sheath (304) slides relative to the shaft (322) during extension and retraction, and so the inflation slot (326) may be positioned on the shaft (322) to accommodate the maximum and minimum extension of the inner sheath (304) while still allowing inflation of the balloon (310).

Figure 11B:
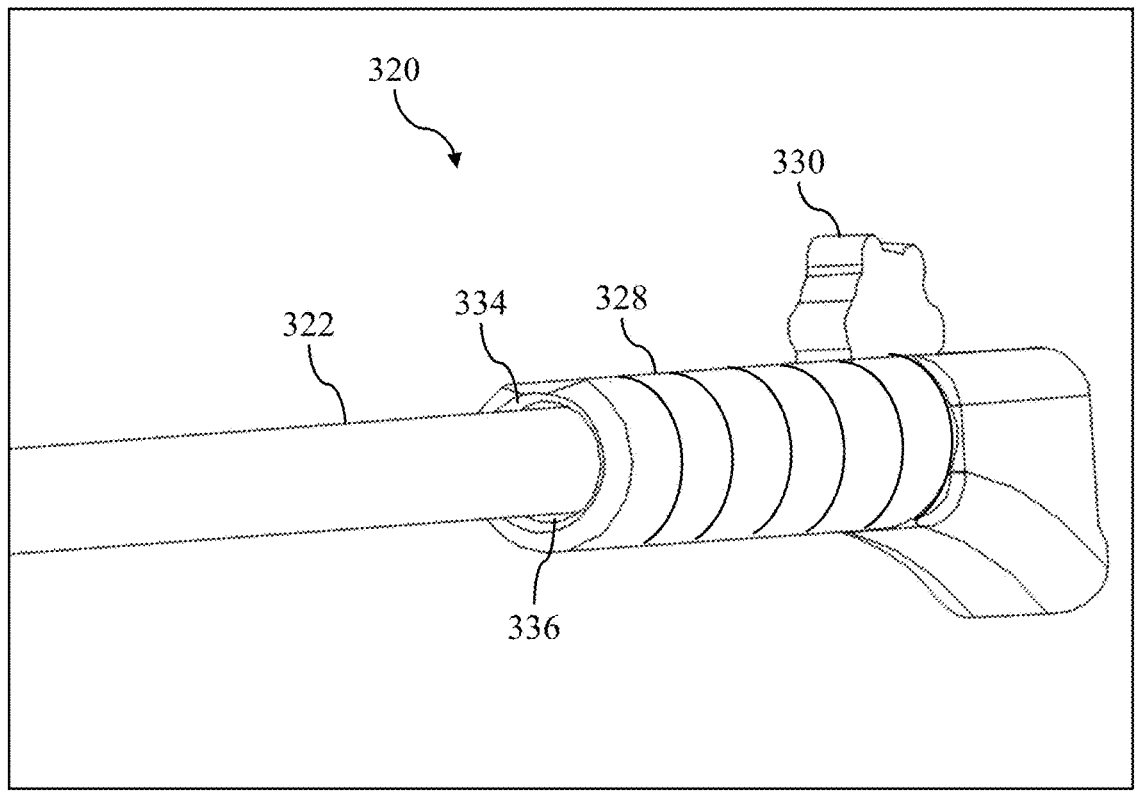
FIG. 11B is a magnified view of the driver of FIG. 11A.

FIG. 11B is a magnified view of the driver (320), focusing on the area of the handle (328). An outer sheath receiver (334) can be seen where the shaft (322) meets the handle (328), and is positioned to receive and seal against the outer sheath (302) when the balloon dilation sheath (300) is installed. Since the outer sheath (302) does not move during extension and retraction of the inner sheath (304), this sterile barrier is maintained throughout use. An inner sheath receiver (336) is visible as an opening around the shaft (322) that extends into the handle itself (328), and is configured to receive the inner sheath (304). The inner sheath (304) may be inserted into the handle (328) until it engages with the slider (330). Once engaged, a movement of the slider (330) will cause a proximal portion of the inner sheath (304) to extend from, or retract into, the handle (328) via the inner sheath receiver (336). Engagement of the inner sheath (304) with the slider (330) may be by way of a friction fit or mechanical connection that occurs upon installation of the sheath (300).

Figure 12A:
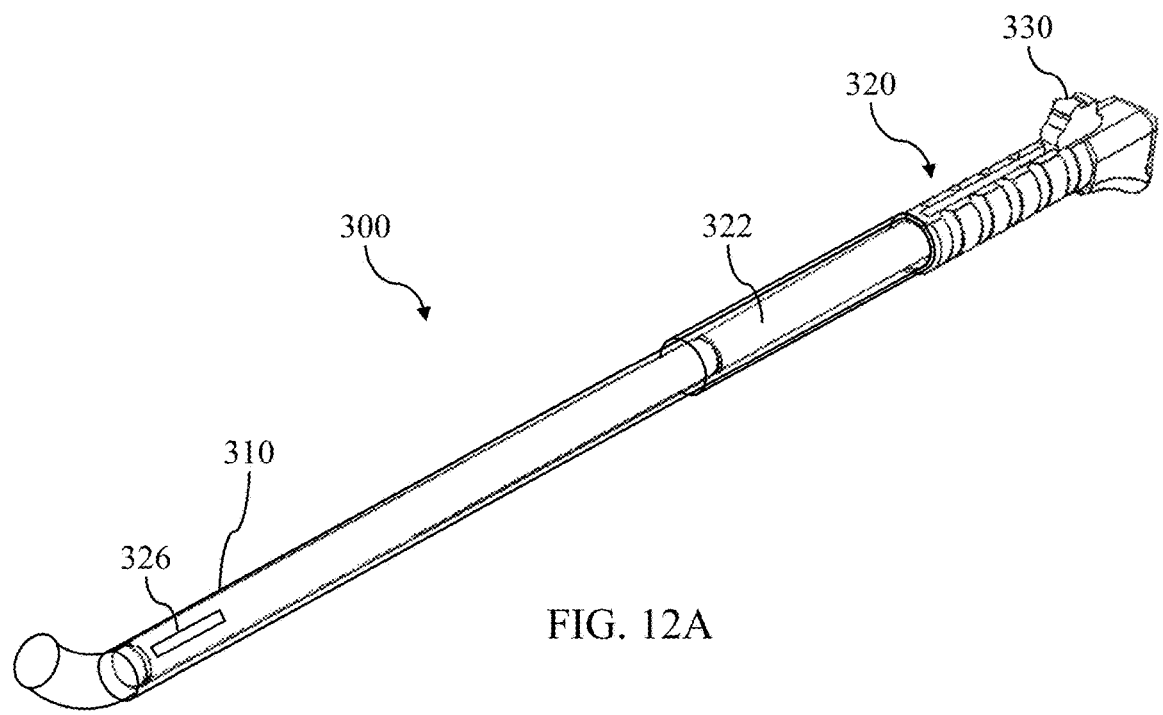
FIG. 12A is a front perspective view of the balloon dilation sheath of FIG. 10A coupled to the driver of FIG. 11A.
Figure 12B:
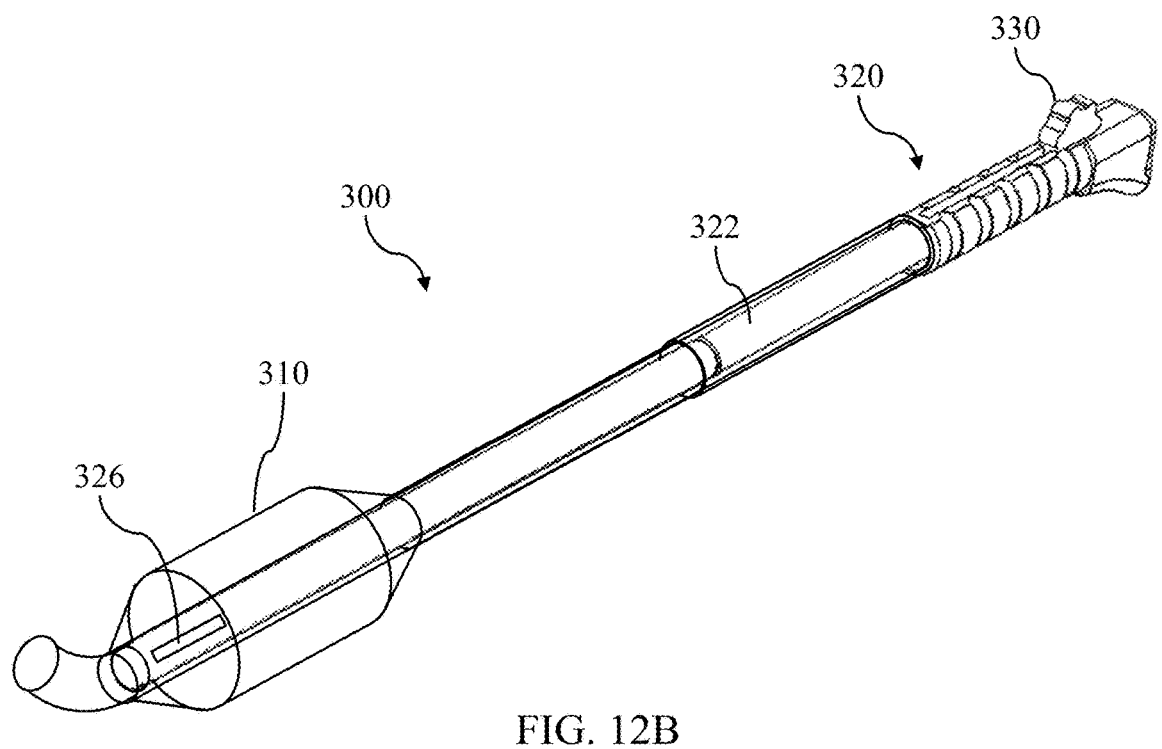
FIG. 12B is a front perspective view of the assembly of FIG. 12A with an expanded balloon portion.

FIGS. 12A and 12B show the fully assembled balloon dilation sheath (300) and driver (320) in a first state where the balloon (310) is not inflated, and a second state where the balloon (320) is inflated, respectively.

Figure 13:
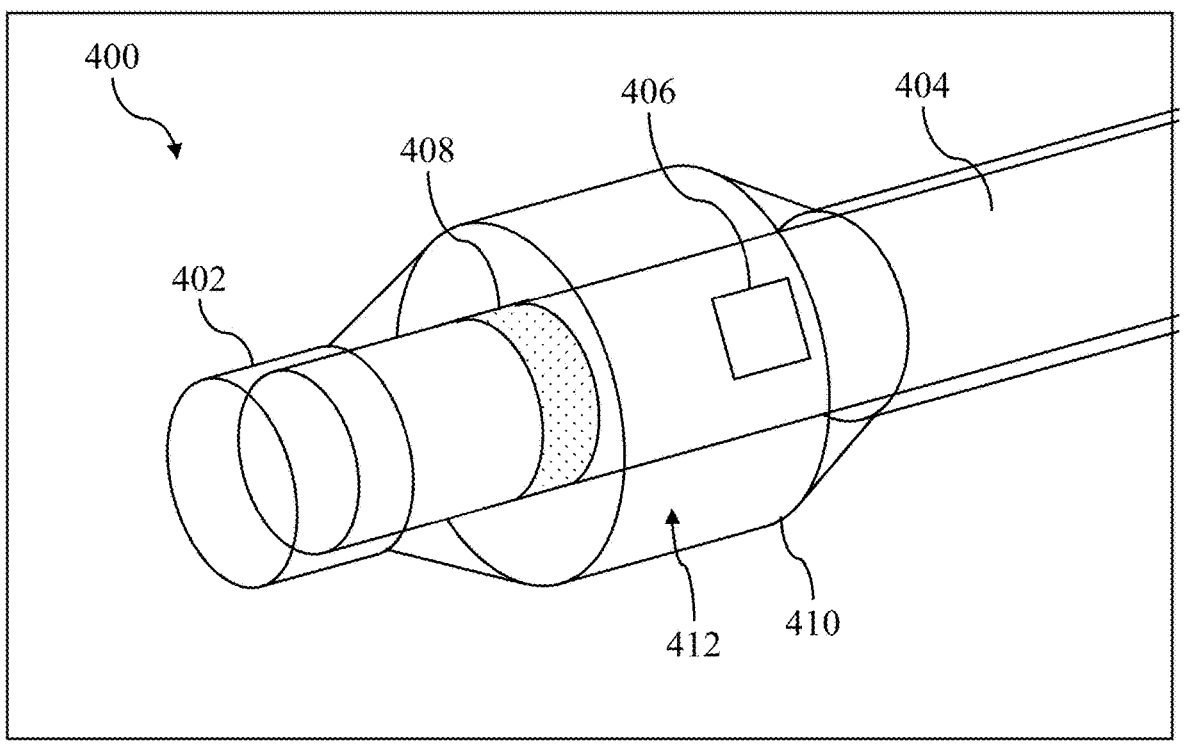
FIG. 13 is a magnified perspective view focusing on a distal tip area of an assembly that includes an exemplary sonic ablation element and sonic ablation instrument.

As another example of a functional sheath, FIG. 13 is a magnified perspective view focusing on a distal tip area (400) of an assembled sonic ablation sheath (402) and sonic ablation instrument (404). The sonic ablation instrument (404) includes a sonic delivery ring (408), which may be, for example, a piezo crystal or other structure capable of producing and/or transmitting sonic power received through a shaft of the sonic ablation instrument (404). The sonic ablation instrument (404) also includes an inflation slot (406) that is configured to deliver and extract a liquid, as similarly described in the context of the inflation slot (326) of FIG. 11A. The sonic ablation instrument (404) may include some or all of the features described in the context of the endoscope (100) or other medical instruments, such as cameras, light sources, depth or range finders, and other features.

Similarly, the sonic ablation sheath (402) may include some or all of the features described in the context of the endoscope sheath (102), such as channels for delivery of irrigation, power, data, inflation, or other resources to the distal tip area (400) of the assembly, as well as sheath memory, as has been previously described. The sheath (402) includes a balloon (412) positioned at the distal tip area (400) that may be inflated and deflated via delivery of liquid via the inflation slot (406) of the sonic ablation instrument (404), as has been described. The balloon (410) is shown in FIG. 13 in an inflated state. As with prior disclosed examples of sheaths, the sonic ablation sheath (402) provides a sterile barrier that prevents contact between the treatment site and the medical instrument (404), and may be removed and replaced between procedures without requiring sterilization of the medical instrument (404) itself.

When the balloon (410) is inflated by liquid delivery, as shown in FIG. 13, it will substantially conform against nearby anatomy, which may be tissue that is targeted for ablation. As a result, the targeted tissue will be in contact with the liquid media within an interior of the balloon (410), separated only by the relatively thin membrane of the balloon (410) wall. In this manner, the liquid within the balloon (410) acts as a sonic transmission media (412), efficiently transmitting sonic power that is delivered by the sonic ring (408) out of the balloon (410) and into proximate tissue, causing ablation of the affected tissue. Sonic power transmits poorly through air pockets resulting in signal/power loss and unpredictable behavior, while transmission via the sonic transmission media (412) is efficient and predictable. As a result, the sonic power delivered via the sonic ring (408) may be fine-tuned for a desired power at a desired distance, resulting in predictable ablation of affected tissue. While the sonic ring (408) is shown as surrounding some or all of the circumference of the medical instrument's distal end, it should be understood that it may be implemented in varying shapes, sizes, positions, patterns, and numbers (e.g., two or more sonic rings) as may be desired for a particular implementation.

Figure 14:
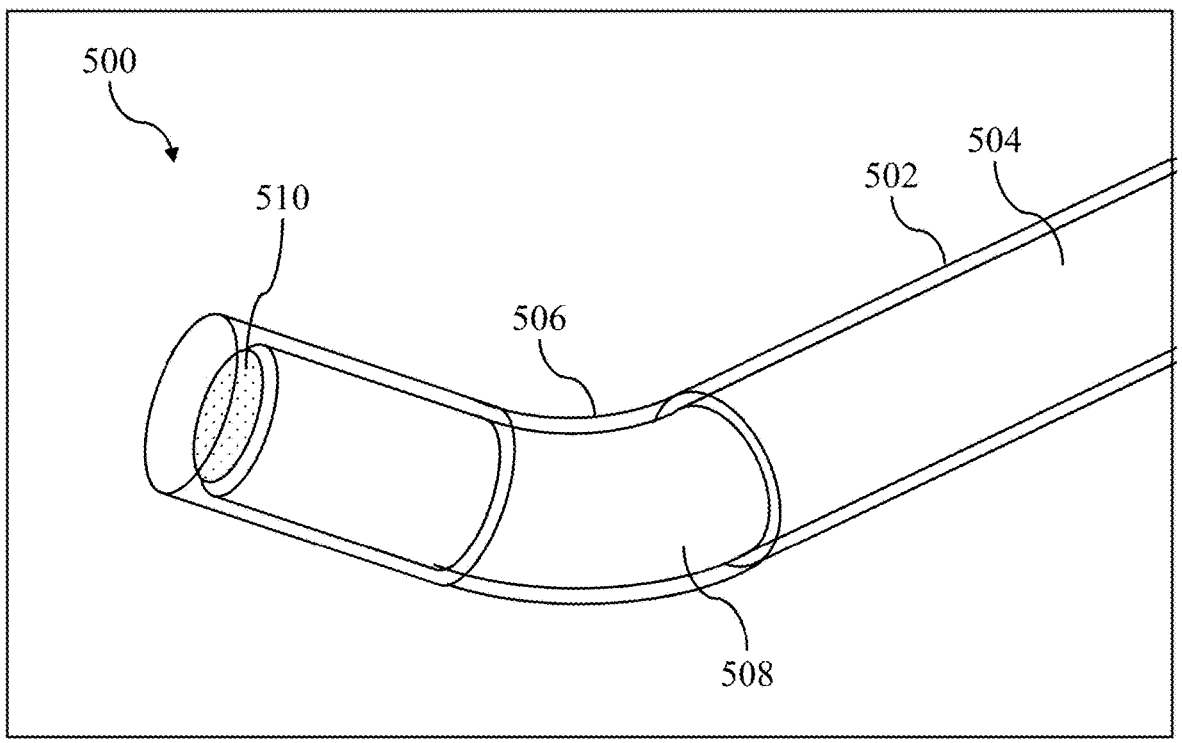
FIG. 14 is a magnified perspective view focusing on a distal tip area of an alternative assembly that includes an exemplary sonic ablation element at the tip of the instrument and sonic ablation instrument.

FIG. 14 is a magnified perspective view focusing on a distal tip area (500) of another assembled sonic ablation sheath (502) and sonic ablation instrument (504). The sonic ablation instrument (504) includes a sonic crystal (510) at a distal tip that is configured to generate and/or transmit sonic power to nearby tissue during an ablation procedure. The sonic instrument (504) includes a flexible portion (508) near the distal tip area (500) that may be flexed to a desired angle for a particular procedure. In some implementations, adjustment of the flexible portion (508) may be performed using mechanical and/or electrical articulation, which may be accomplished via extension and retraction of control lines within the shaft of the medical instrument, via an electrical current applied to an electro-reactive surface or member of the medical instrument (504), or in other ways. In some implementations, adjustment of a malleable flexible portion (508) may be performed manually using a shaping tool, or by hand, to create a desired angle.

The sonic ablation sheath (502) may have some or all of the features of other disclosed sheaths, such as the endoscope sheath (100), and provides a sterile barrier between the medical instrument (504) and the treatment site. The sonic ablation sheath (502) may be formed of similar materials as other sheaths, and may include a flexible portion (506) made from the same materials, or a more flexible material, such that the sonic ablation sheath (502) will confirm to the shape of the flexible portion (508) of the medical instrument (504) as it is formed or articulated to a desired angle. Projection of sonic power via the sonic crystal (510) may occur through a small open area between the crystal (510) and the distal tip of the sonic ablation sheath (502), or the sonic ablation sheath (502) may be configured to fill that area with a liquid transmission media via delivery of liquid via the medical instrument (504) or a channel of the sheath (502), as has been previously described.

Figure 15:
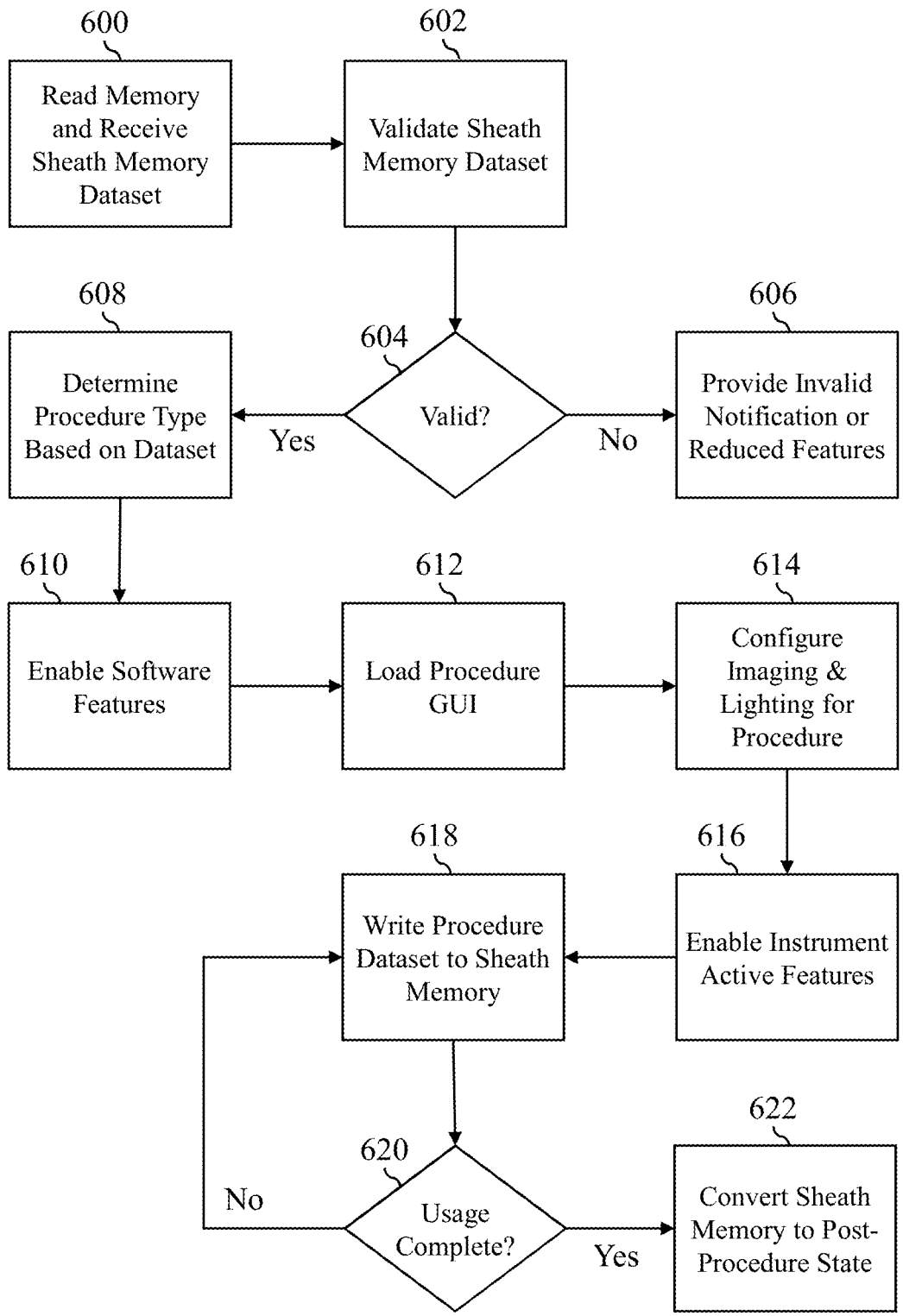
FIG. 15 is a flowchart of an exemplary set of steps that may be performed to configure a medical instrument for use with a functional sheath.

FIG. 15 is a flowchart of an exemplary set of steps that may be performed to configure a medical instrument for use with a functional sheath. The steps of FIG. 15 may be performed with a variety of assembled sheaths and medical instruments, which may include sheaths having a sheath memory, as well as sheaths that enable functional features of the medical instrument such as delivery of irrigation fluid to the treatment site, delivery of electric power to an ablation electrode, and other features, as have been previously described. The steps of FIG. 15 may be performed by or with one or more of the described devices, such as a medical instrument, the image processor (104), the remote server (106), or other devices.

When a sheath is coupled to a medical instrument, a sheath memory dataset may be received (600) that includes data related to the use of the sheath. This may include, for example, an authorization or activation key or code, a model and serial number, software configuration settings for image capture, image analysis, or other features, and other information. The receiving device may validate (602) the sheath memory dataset to verify that the sheath is usable with the medical instrument, and what features, if any, are available for use. Validation may include verifying the dataset against a locally stored table, validating the dataset by use of a decryption key or hashing algorithm, querying a remote database, or otherwise. Where the dataset is invalid or unavailable, such as where the sheath has already been used for a procedure, or has been disabled due to a manufacturers recall or other safety issue, the system may provide a notification via a display or other device indicating that the sheath is not usable, or may only be used with a reduced feature set (e.g., automated image analysis, tissue ablation, or other features may be disabled).

Where the dataset is valid (604), the system may determine (608) the type of procedure or procedures that the sheath is usable for based on the dataset. As an example, one sheath may be usable for one or more ENT related imaging and diagnosis procedures, which may be determined based upon the received dataset.

The system may also enable (610) one or more software features based upon the dataset and procedure type. Continuing the above example, where the sheath is usable for automated image analysis for ENT related characteristics, the system may enable a software application that is configured to provide such analysis.

The system may also load (612) a procedure or use specific graphical user interface (GUI) so that it is ready for use via the image processor (104) or another device. Continuing the above example, the image processor (104) may automatically being displaying an interface that the practitioner may use to perform ENT imaging and analysis.

The system may also configure (614) a camera and light sources for the particular procedure, which may include loading configurations specific to that procedure to set a desired image resolution, framerate, light intensity, or other characteristics that have been selected and/or optimized for that procedure.

The system may also enable (616) one or more active features of the medical instrument and/or sheath, which may include enabling an ablation, irrigation, balloon dilation, or other feature for use and activation via manual user controls or software interface controls.

The system may also write (618) various types of procedure data to the sheath memory, which may include captured images, captured video, error logs, software logs, and other data produced during the procedure that may be useful to patients, practitioners, or others.

When the system determines that use of the sheath is complete (620), which may be determined in response to a user input, removal of the sheath from the medical instrument, after the passage of a certain period of time, after the use of certain features, or after a limited number of uses of certain features have been exhausted, the system may disable activated features and software, and may convert (622) the sheath to a post-procedure state. This may include erasing or overwriting portions of the sheath memory to prevent future validation, while maintaining data that was written (618) to the memory during the procedure.

Figure 16:
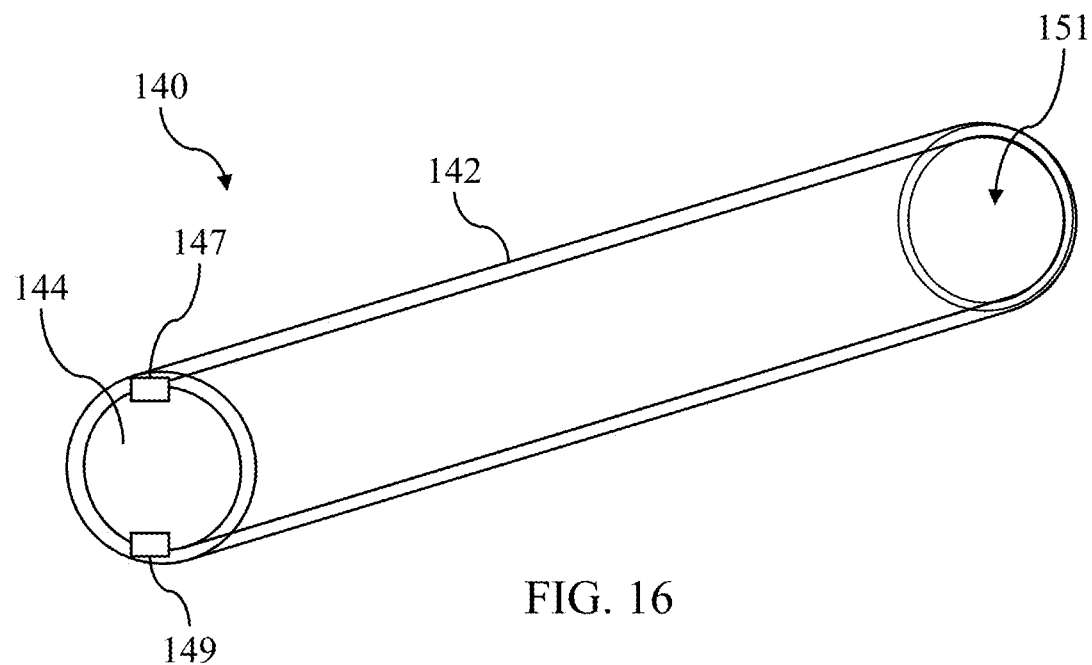
FIG. 16 is a perspective view of an alternate exemplary endoscope sheath with lens integrated light emitting diodes.

As another example of sheaths usable with systems such as that shown in FIG. 1, FIG. 16 is a perspective view of an alternate exemplary endoscope sheath (140) with a pair of lens integrated LEDs (147, 149). The LEDs (147, 149) may be positioned on a surface of a lens (144) through which an endoscopic camera may capture images of anatomy. The sheath (140) includes a substantially transparent body (142) that defines an opening (151) into an interior cavity into which an endoscopic shaft may be inserted, as has been described above. The LEDs (147, 149) are positioned at the exterior edges of the lens (144) such that the endoscope view from within the opening (151) is minimally obstructed. Illumination provided by the LEDs (147,149) is not transmitted through the lens (144) or any other portion of the sheath (140), which prevents lens flare and other undesirable lighting artifacts from appearing in captures images. A wire providing power and control signals to the LEDs (147, 149) may be contained within a sidewall of the body (142) (e.g., such as within the channel (128), as described above).

The lens (144), as well as other lenses or optical surfaces through which light is transmitted or imaging performed disclosed elsewhere herein, may include anti-glare, anti-flare, and anti-fogging treatments to improve imaging quality and reliability within the nasal cavity and other anatomical passages.

Figure 17A:
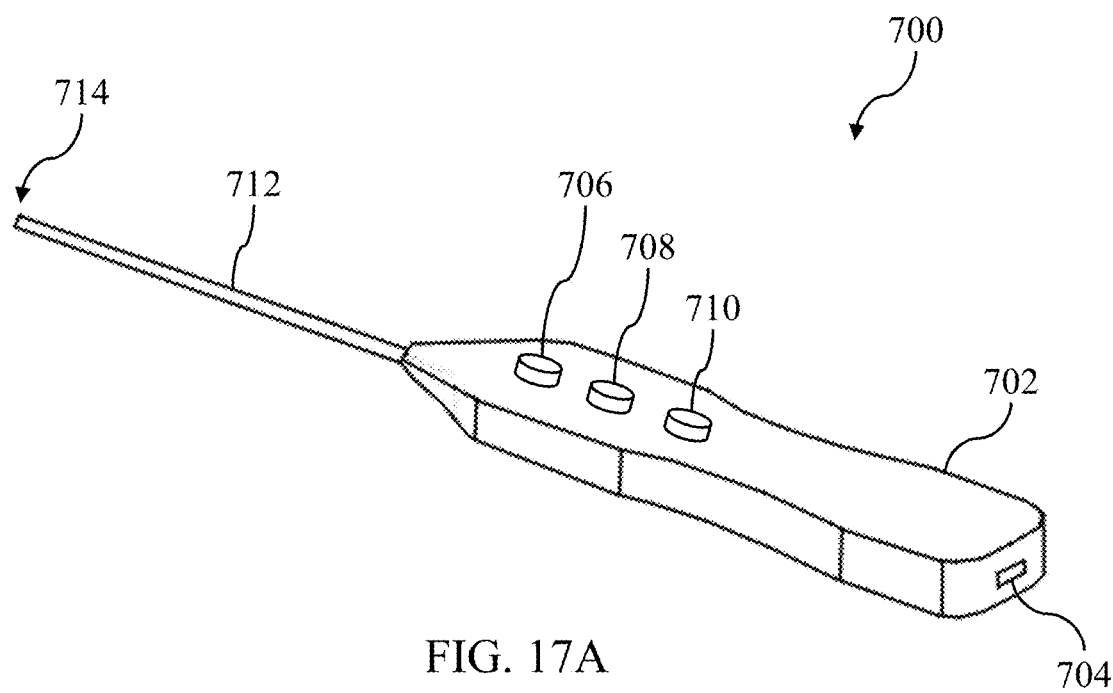
FIG. 17A is a perspective view of an alternate exemplary endoscope.

As another example of an endoscope usable with systems such as that shown in FIG. 1, FIG. 17A is a perspective view of an alternate exemplary endoscope (700) that may be used instead of or in addition to the endoscope (100). The endoscope (700) may couple to the image processor (104) or another device via a wireless connection (e.g., Bluetooth, Wi-Fi) or a wired connection (e.g., USB-C, the cable (110)). The endoscope (700) includes a body (702) that may include one or gripping features (e.g., contoured edges, high friction or grip surfaces, thumb or finger rests), and that contains internal circuitry and other components of the endoscope (700).

A set of controls (706, 708, 710) are included on the body (702) and may be interacted with by a user during use of the endoscope (700). The set of controls (706, 708, 710) are depicted as press buttons in FIG. 17A, but may also be implemented as a multi-directional control column or other multi-directional switch, a pressure sensitive surface, a motion controlled optical sensor, a toggle switch, or other control interfaces. The set of controls (706, 708, 710) may be used to activate or configure characteristics of the endoscope (700) including, for example, capture of images, capture of video, intensity of LEDs, application of cleaning fluid or other fluids to the sheath distal tip, and image color and brightness adjustments (e.g., white balance, color correction, grayscale mode). A shaft (712) extends from the body (702), and in some implementations may be formed rigidly and with a static length that is selected based upon the procedure depth of common ENT procedures. A distal tip (714) of the shaft (712) may contain a camera, LEDs, irrigation channels, and other features described above (e.g., such as those relating to the distal tip (118) of FIG. 8). The endoscope (700) may advantageously be held and operated with a single hand, and may be used in a variety of procedures without requiring any bending or articulation of the shaft (712), management of attached cables such as the cable (110), or other distractions present with many other endoscopes. A port (704) may be configured to receive a cable for charging an internal battery, powering the endoscope (700), and exchanging data between the endoscope (700) circuitry and an attached device, for example.

FIGS. 17B and 17C show side elevation views of the endoscope (700), with the view shown in FIG. 17C being a cross sectional view. As can be seen in FIG. 17C, a power and data cable (713) couples the camera, LEDs, and other components of the distal tip (714) with a control board (718), which may be a circuit board including logic for image capture, local image processing, LED control, and other functions. The control board (718) is coupled to a procedure board (716) which may include a memory and further logic enabling the storage of procedure data, the storage and execution of advanced imaging features, and data relating to usage tracking, usage control, and enabling or disabling of advanced features. The port (704) is coupled to the procedure board (716), and a device attached via the port (704) may receive data stored on the procedure board (716) (e.g., images, video, procedure data), or write data to the procedure board (716) (e.g., enabling features, disabling features). In some implementations, the port (704), a wireless communication device, or another device through which the endoscope (700) communicates with the image processor (104) may be disabled or non-functional until a valid dataset is read from the sheath memory (130) or another location (e.g., such as when the sheath (102) is coupled to the endoscope (700), or upon activation of the endoscope (700) features in another manner, as will be described below).

In some implementations, some or all of the power and data cables (713), which may be one or several cables, may couple to a signal amplifier (719) that is configured to receive signals from the camera, and amplify or otherwise condition the signals. It may be advantageous to minimize the length of the cables (713) between the camera and the signal amplifier (719) in order to minimize the length of travel of the signal, and reduce the opportunity for signal degradation or noise to be introduced to the signal. In some implementations, the section of cables (713) coupling the camera chip to the signal amplifier (719) may be selected based upon the required length of transmission in order to maximize the received downstream signal quality. This may include, for example, highly conductive twisted strands of wiring capable of transmitting low amplitude signals with minimal noise or signal degradation.

The quality of image signals may be further preserved by locating the control board (718) or another component capable of processing image signals proximately to the signal amplifier (719) or the terminal point of the cables (713) in order to ensure that the control board (718) receive the highest quality signal possible. Upon receiving image signals, whether amplified or not, the control board (718) may perform additional processing to preserve the received signal, which may include converting or encoding the signal into a binary format or other format that may be more readily stored and transmitted without compromising image quality. In some implementations, the amplifier (719) may be positioned at the distal tip (714) of the shaft (712) rather than within the body (702) of the endoscope (700), to further minimize the distance of signal travel.

While the endoscope (700) has been described as being re-usable multiple times with the sheath (102) being disposable after use, it should be understood that different components may be reusable and/or disposable in varying implementations. As an example, with continued reference to the endoscope (700) of FIGS. 17A-17C and other endoscopes described herein, it should be understood that in some implementations the shaft (712) portion (e.g., the shaft (712), cables (713), and distal tip (714)) may be removable from the body (702) so that they may be disposed and replaced after a certain number of uses, or if damaged, or for other reasons. In such implementations, the removable shaft (712) portion may be temporarily or permanently coupled with the sheath (102), such that each may be removed and replaced individually as needed, or such that the sheath (102) and shaft portion may be removed and replaced as a single piece.

In some implementations, the shaft (712) may be comprised of various metals, and may be formed as a hollow cylinder of varying length and sidewall thickness. In this manner, the cables (713) may be contained within a channel defined within the hollow shaft (712). As a result, the cables (713) may be passively shielded from signal interference from outside the shaft (712) based upon the metallic materials and characteristics of the shaft (712). In such implementations, the shaft (712) may be coupled to an electrical ground (717) by a ground cable (715), such that any signals or electrical charge received by the shaft (712) may be directed to the ground (717) rather than transferred to the cables (713), where image signals may be negatively influenced. In such implementations, it may be advantageous to ensure that the shaft (712) provides this passive shielding effect along substantially the entire length of the cables (713), such that there is minimal or no unshielded length prior to coupling to the signal amplifier (719) or the control board (718).

Figure 18:
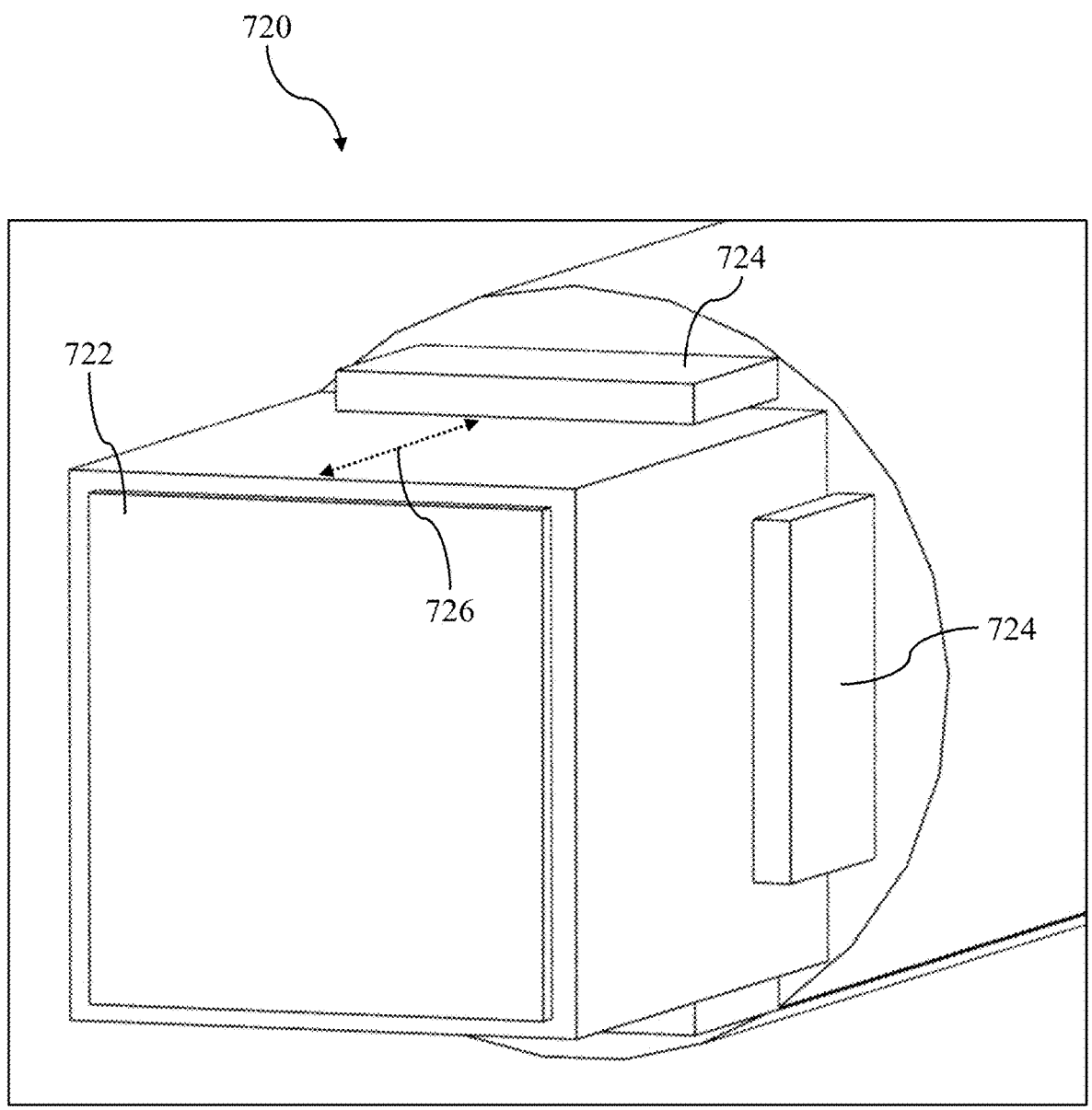
FIG. 18 is a magnified perspective view focused on an exemplary distal tip of an endoscope.

As further example of the features and variations on distal tips, FIG. 18 is a magnified perspective view focused on an exemplary distal tip (720) of an endoscope, such as might be implemented with the endoscopes (100, 700) disclosed herein. A camera chip lens (722) (e.g., charge-coupled device ("CCD"), complementary metal-oxide semiconductor ("CMOS")) is offset a distance (726) beyond a set of four surrounding LEDs (724), such that illumination from the LEDs (724) does not directly strike the camera chip lens (722). The lens (144) or another sheath lens may snugly fit to the camera chip lens (722) when the sheath is installed, creating a direct optical interface. Light from the LEDs (724) is transmitted through the sidewalls and/or other portions of the sheath instead of the lens (144), providing desirable illumination of local anatomy while minimizing glare, flare, and undesirable lighting artifacts.

Figure 19:
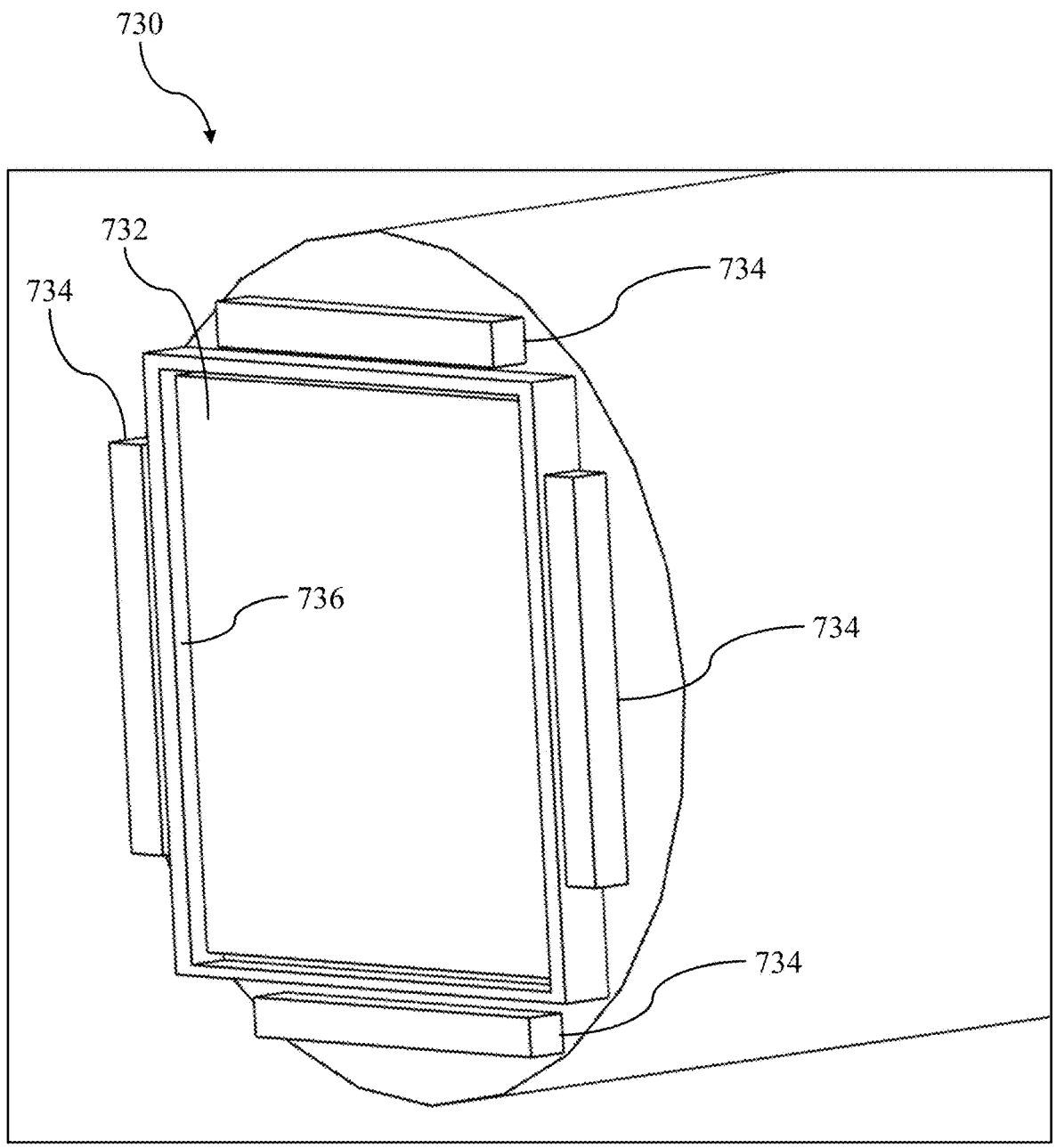
FIG. 19 is a magnified perspective view focused on an alternate exemplary distal tip of an endoscope.

FIG. 19 is a magnified perspective view focused on an alternate exemplary distal tip (730) of an endoscope, such as may be implemented at the distal tip of any of the endoscopes (100, 700) disclosed herein. A camera chip lens (732) is positioned at a depth within an enclosure (736) that includes a raised sidewall that extends beyond the surface of the camera chip lens (732). A set of four LEDs (734) surround the enclosure (736), and light emitted from the LEDs (734) is prevented from directly striking the camera chip lens (732) by the enclosure (736). As with the example of FIG. 18, the lens (144) or another lens may be shaped to insert within the enclosure (736) and achieve a direct optical interface with the camera chip lens (732). Illumination from the LEDs (734) is transmitted through portions of the sheath other than the lens (144), providing reflective illumination without causing glare, flare, or other lighting artifacts.

Figure 20A:
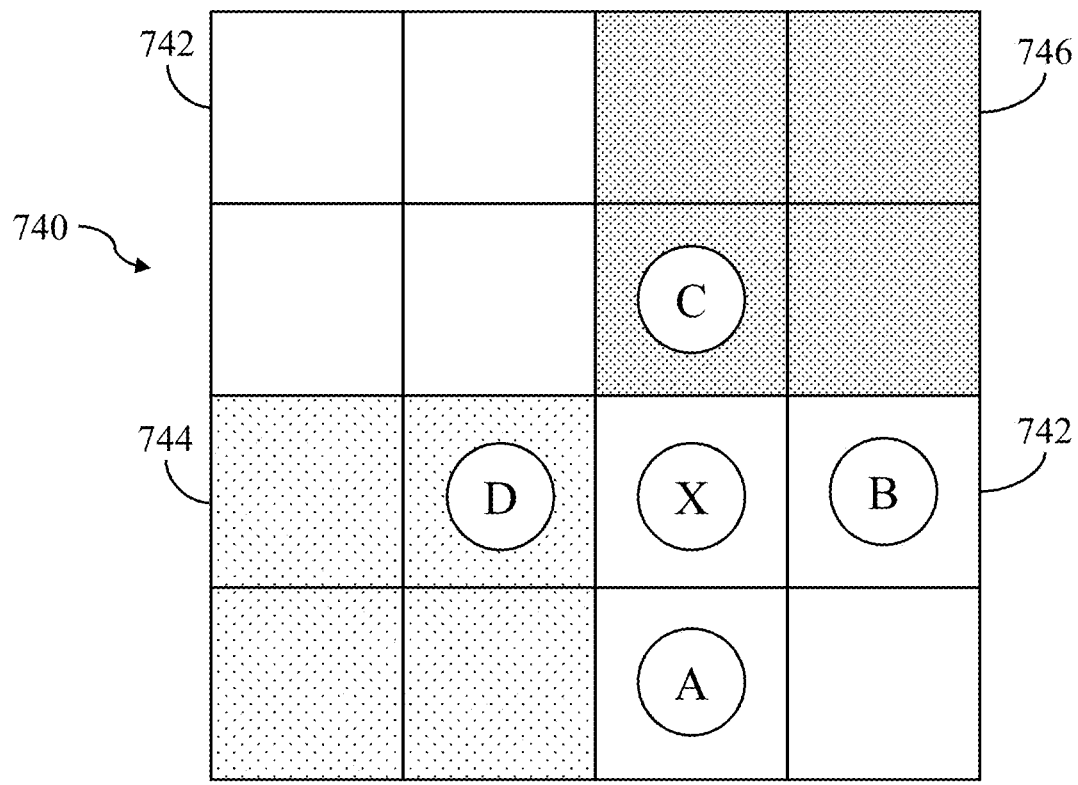
FIG. 20A is a schematic diagram illustrating a region of pixels of a charge-coupled device (CCD) of an endoscope camera.

FIG. 20A is a schematic diagram illustrating a region (740) of pixels of a CCD of an endoscope camera, though the teachings may also be applied to CMOS variations on digital imaging. The region (740) includes two green pixel regions (740), a blue pixel region (744), and a red pixel region (746). Due to the scale at which endoscopic imaging is captured as disclosed herein, debris present on a lens (e.g., tissue, mucus) or fogging or misting of the lens that is invisible to the human eye may obstruct one or several regions of an image when captured by the CCD, resulting in poor image quality and/or undesirable imaging artifacts. Analysis of resulting images (e.g., using an expert module, machine learning system, or other image recognition module) can identify regions where the image is obstruction both in isolation, and in the context of surrounding image data.

For example, where a single pixel, or small grouping of pixels captures an image that is mostly white or grey, where all surrounding pixels capture an image that is a rich pink or red associated with healthy tissue, it can be determined that there is likely an obstruction by mucus, fogging, or other material. Referring to FIG. 20A, suppose that the region "X" is detected as likely being obstructed in this manner. The captured image may be adjusted to correct for this obstruction, either locally to the endoscope (e.g., such as on the control board (718) as images are captured) or another device (e.g., the image processor (104), the remote server (106)). To correct the image, the obstructed region "X" may be recreated from image data from nearby unobstructed pixels, such as those labeled "A", "B", "C", and "D". The image data that is interpolated from surrounding pixels may replace the obstructed image data, which will reduce the number of obstructed regions displayed to an end user when the resultant image is shown.

Figure 20B:
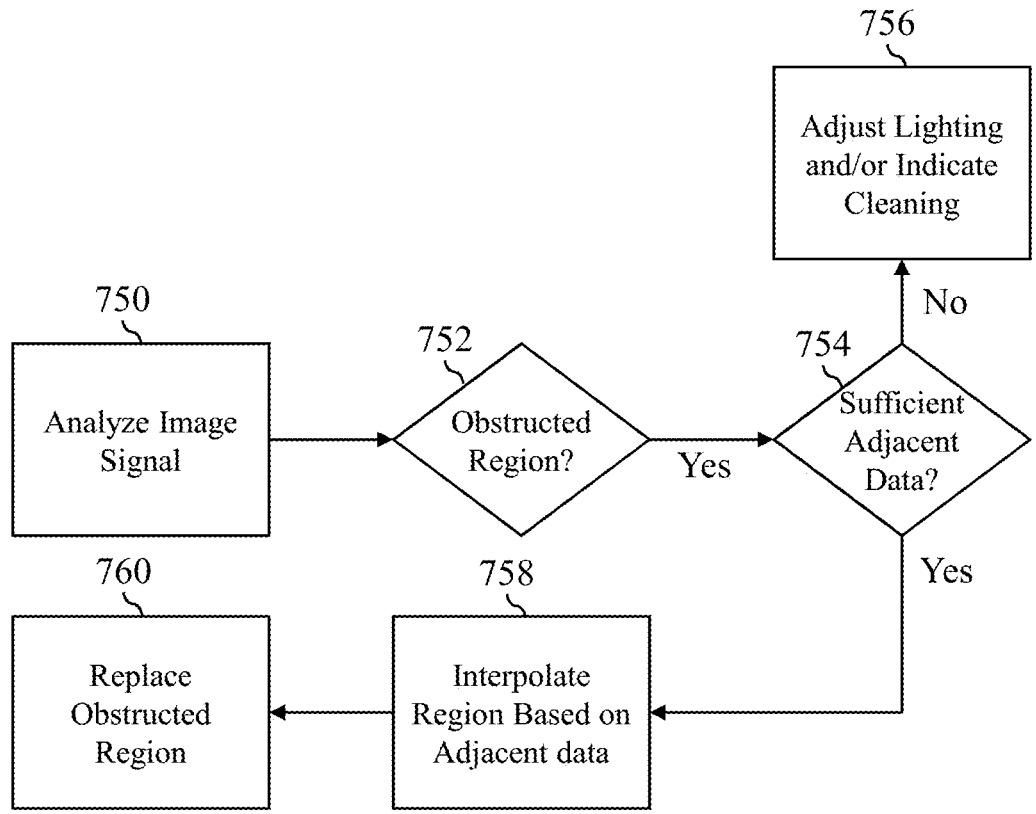
FIG. 20B is a flowchart of an exemplary set of steps that may be performed to correct image errors resulting from obstructed CCD pixels.

As an example of the above, FIG. 20B is a flowchart of an exemplary set of steps that may be performed to correct image errors resulting from obstructed CCD pixels. A received image signal is analyzed (750) using an expert module, artificial intelligence, or other machine vision or object recognition process. Where an obstructed region is detected (752), the system will determine where there is sufficient adjacent image data (754) to correct the obstruction, based upon the size and shape of the obstruction (e.g., a largely circular or square obstruction covering a number of pixels will be a poor candidate for correction, while contiguous pixels that are arranged in narrow, irregular tracks or trails will be a good candidate). If there is not sufficient adjacent data (754), the system may automatically adjust (756) the lighting provided by endoscope LEDs to determine if increased or decreased illumination resolves the imaging issue, or may provide a warning to the user that the endoscope lens may need to be cleaned.

Where there is sufficient data (754), the system may interpolate (758) replacement pixels for each region or sub region of obstructed pixels based on the available adjacent image data. Such interpolation may be based upon direct replacement by a most proximal pixel, or may be based upon a blended replacement from several nearby pixels (e.g., a color determined by the combination of pixels "A" through "D", in the example of FIG. 20A). Upon interpolation of each affected region, the obstruction region may be replaced (760) prior to display of the captured image.

Figure 21A:
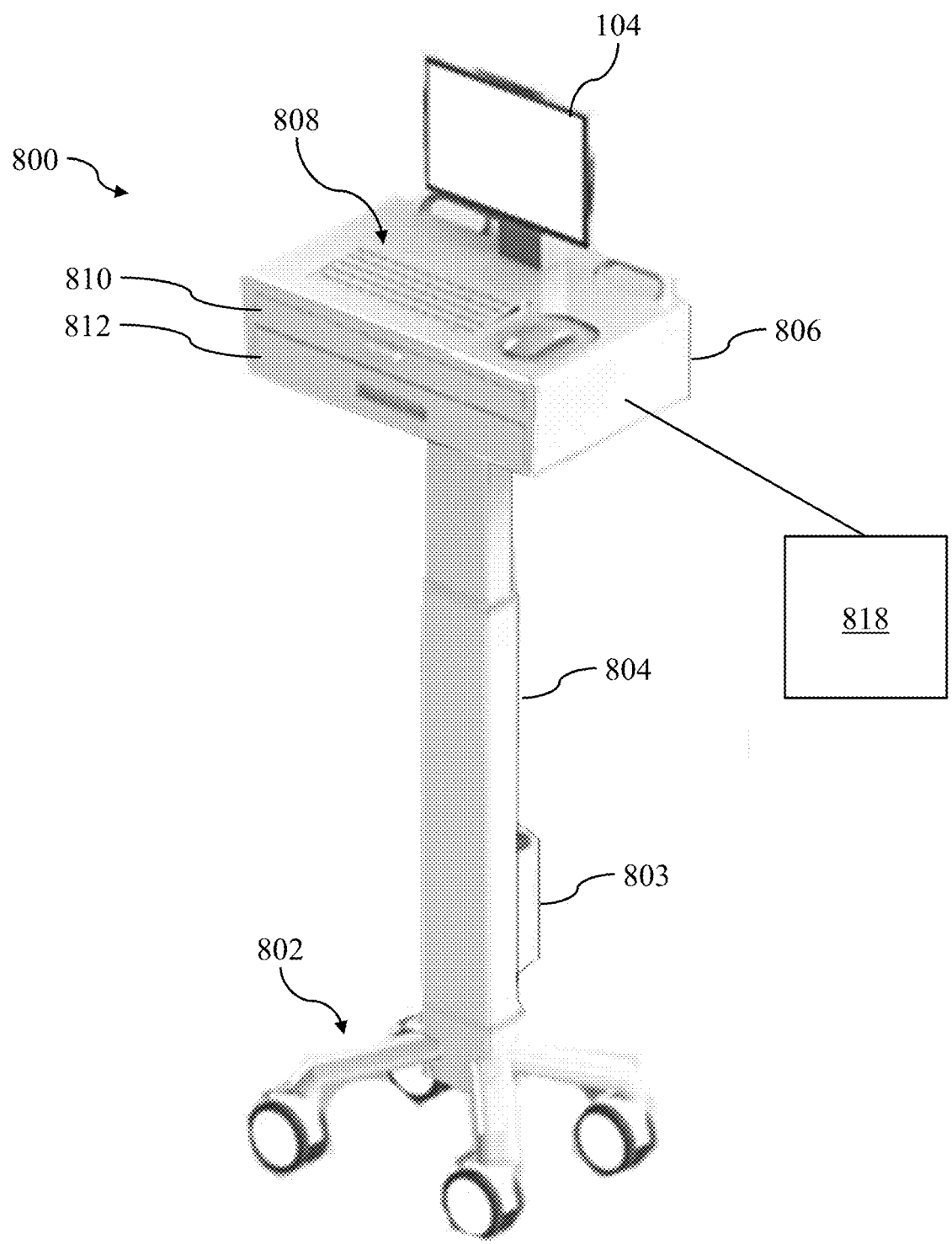
FIG. 21A is a perspective view of an exemplary cart usable with the system of FIG. 1.

FIG. 21A is a perspective view of an exemplary cart (800) usable with the system of FIG. 1. The cart (800) includes a set of wheels (802) allowing the cart to (800) to be wheeled between locations. The set of wheels (802) are arranged with a relatively small footprint, which may be achieved by arranging the equipment carried by the cart (800) to provide a low center of gravity. The resultant footprint is advantageous for moving the cart through doorways, and into ideal locations within small exams rooms for performance of procedures.

A height adjustable column (804) extends upwards from the set of wheels (802), and may allow a cabinet (806) of the cart (800) to be raised or lowered, with the range of adjustment varying between about 12 inches and about 36 inches. The column (804) also defines a hollow interior cavity through which cabling may be run. A lower equipment case (803) is mounted to the column (804) just above the set of wheels (802), and contains one or more battery packs that are capable of powering the electrical components of the cart (800) for substantial lengths of time without recharge, allowing the cart (800) to be operated in varying locations without requiring the use or presence of a nearby wall outlet. The low mounted batteries also serve to lower the center of gravity of the cart (800) providing a more stable base, despite the small footprint.

Figure 21B:
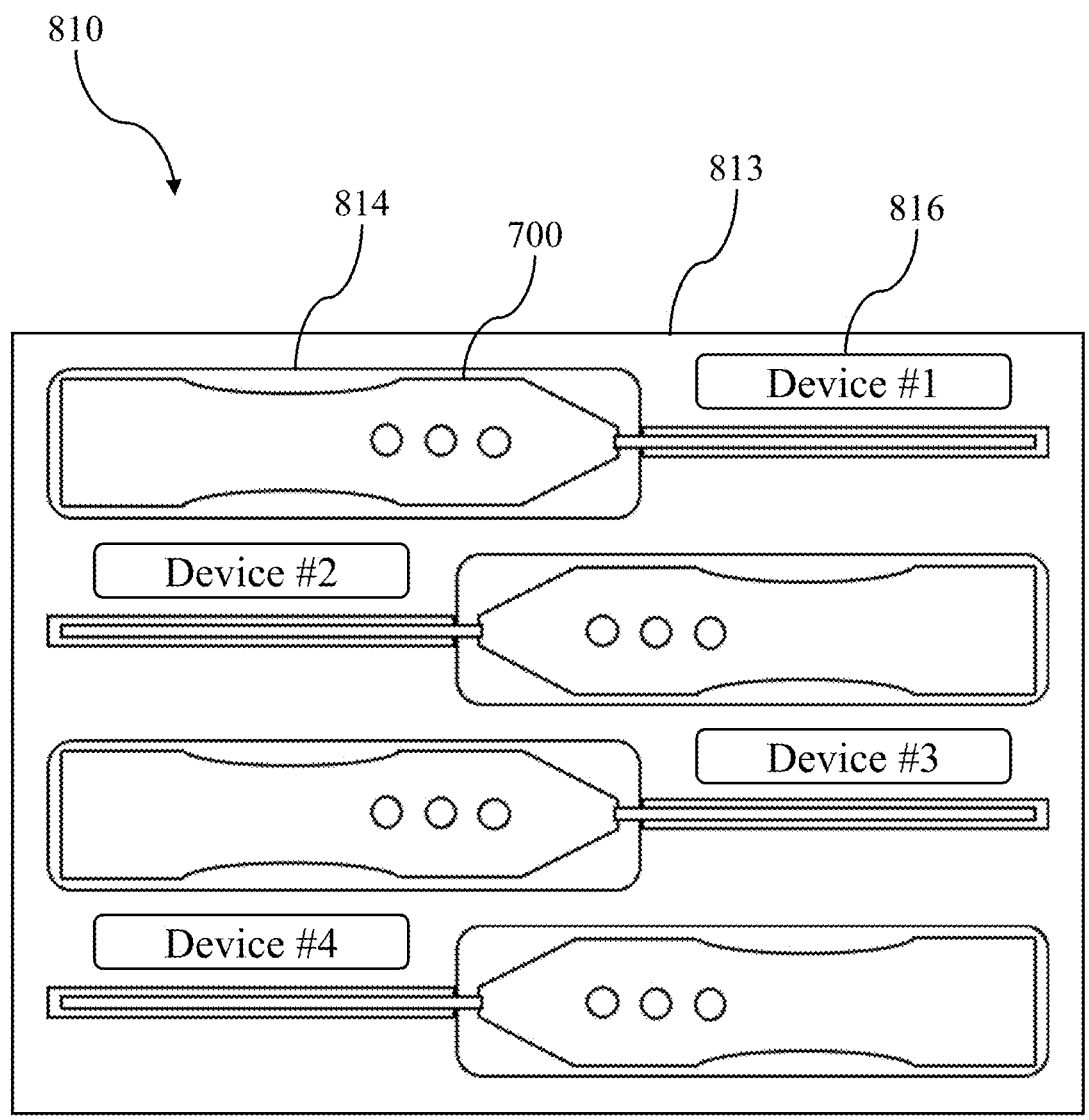
FIG. 21B is a top-down view of a first exemplary drawer arrangement of the cart of FIG. 21A.
Figure 21C:
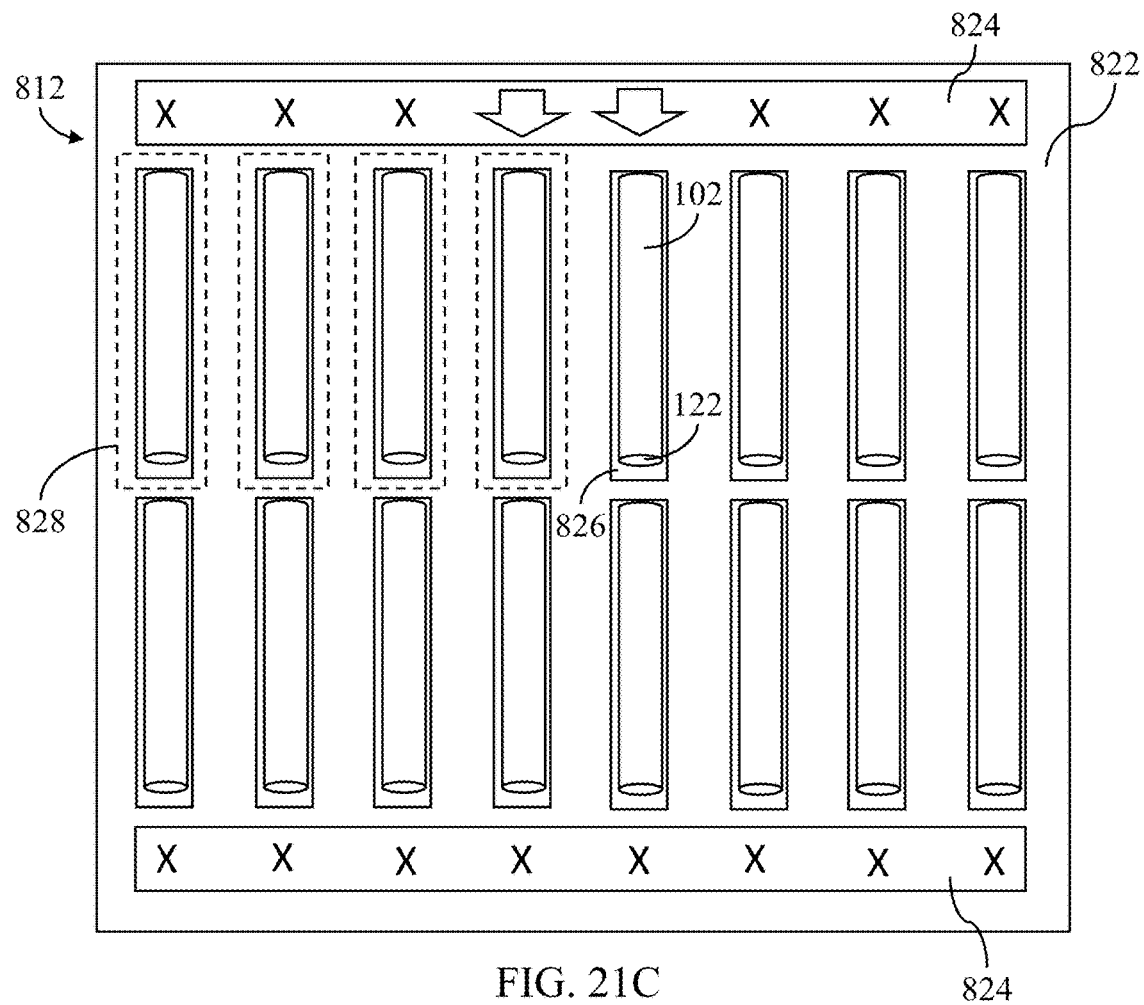
FIG. 21C is a top-down view of a second exemplary drawer arrangement of the cart of FIG. 21A.

The cabinet (806) provides a work surface on which one or more user interface devices may be operated (e.g., keyboard, mouse, writing pad), and a mounting point for the image processor (104) or another processing and display device configured for use with the system. The cabinet (806) also includes a first drawer (810) and a second drawer (812), which are configured to store and provide easy access to endoscope and sheath components, as illustrated by FIGS. 21B and 21C. The cabinet (806) also includes one or more ultraviolet light emitters (818) disposed within the cabinet, and directed to emit ultraviolet light towards the contents of the first drawer (810), the second drawer (812), or both, with such light being emitted continuously or intermittently, depending upon a particular configuration, at an intensity that provides a surface sterilizing effect. As one example, the light emitter (818) may function automatically for the entire duration of time that an associated drawer is closed, or may function for a pre-determined period of time (e.g., 60 seconds) each time an associated drawer is closed.

While the disclosed sheaths are typically disposed after one use, the same handheld endoscope may be protected from contamination by the sheath, and used for several procedures in quick succession, and may only be subjected to conventional sterilization methods occasionally or not at all. Instead, the handheld endoscope may be stored in the cabinet (806) for brief periods of time between uses, and will undergo surface sterilization by operation of the light emitter (818). In this manner, the cabinet (806) provides a point-of-care storage and sterilization solution for an endoscope with removable and disposable sheath, and so does not require lengthy periods of time where the endoscope is out of service, and does not require sterile and non-sterile packaging, transport, etc.

FIG. 21B is a top-down view of an exemplary interior arrangement of the first drawer (810) or the second drawer (812). An insert (813) may be constructed of plastic, metal, foam, or other materials, or combinations thereof, and includes a set of cutouts (814) sized to hold an endoscope such as the endoscope (700) shown in FIG. 17A. Each device position includes a status indicator (816) at which a temporary label or writing may be placed to identify or indicate the status of an associated endoscope (700). In some implementations, the status indicator (816) for each position may instead be a liquid crystal display ("LCD") or LED display ranging from a simple multi-segment alpha-numeric display, to a full color high resolution display. In such implementations, the electronic displays for each position may communicate with the device placed at that position (e.g., wirelessly, or via a USB-C or other wired data connection that is completed when the endoscope (700) is placed for storage) to identify the device and display status information (e.g., battery charge, usage information, enabled features). Alternately, a single-board computer ("SBC") or other small form factor computing device included with the card (e.g., positioned within the lower equipment case) may be configured to drive each display based upon data locally stored or access over a network (e.g., a serial number or other identifier may be received from the endoscope (700), and used to retrieve and display additional information from a remote source).

FIG. 21C is a top-down view of an exemplary interior arrangement of the first drawer (810) or the second drawer (812). An insert (822) may be constructed of plastic, metal, foam, or other materials, or combinations thereof, and includes a set of cutouts (826) sized to hold a set of sheaths such as the sheath (102) of FIG. 1, or other sheaths disclosed herein. Some or all of the cutouts (826) may be covered with a sterile film (828) that may be peeled away, cut, or punctured in order to access each stored sheath at procedure time.

Figure 21D:
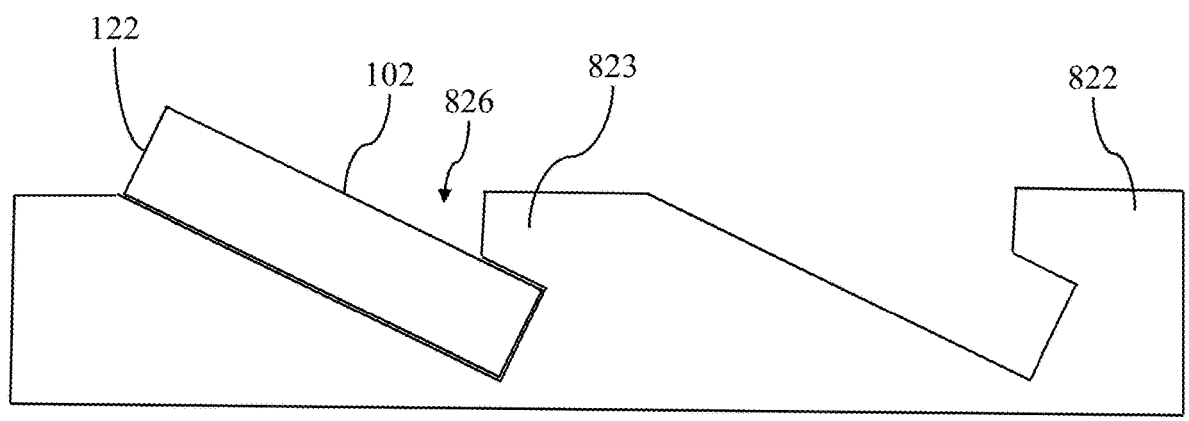
FIG. 21D is a schematic diagram illustrating the second drawer arrangement of FIG. 21A with each sheath stored at an angle.

The cutouts (826) in which the sheaths rest during storage may provide an inclined angle for the sheaths to aid in mounting the sheath to the endoscope (700). As an example, FIG. 21D shows a schematic diagram of a sheath (102) stored at an inclined angle within a cutout (826) portion of the insert (822). In this manner, the open edge (122) is presented to a user opening the drawer (812), allowing for the shaft (712) to be inserted into the sheath (102) without requiring that a user pick up or touch the sheath. The cutout (826) also includes a grip portion (823), which may be formed of flexible foams, rubbers, or other friction materials, which stabilizes the sheath (102) during insertion of the shaft (712) and then releases the sheath (102) as the endoscope (700) is pulled outwards. In some implementations, the grip portion (823) may extend along substantially the entire length of the sheath (102) such that only the sheath open edge (122) is visible. In this manner, the insert (822) may preserve the sterility of the sheath exterior until it is mounted to an endoscope (700) and removed for procedure use.

Returning to FIG. 21C, that figure also shows an indicator panel (824) positioned above a row of sheaths, and another indicator panel (824) positioned below a second row of sheaths. The indicator panel (824) may provide a surface for writing or placing a label indicating the status of each sheath, or, in some implementations, may be an LED or LCD display configured to programmatically provide information related to each sheath. Displayed information may be determined based upon information read from the sheath memory (130) or another memory device associated with the sheath, or may be accessed and retrieve from a remote data source, and may indicate the status or usability of the sheath. In some implementations, the configuration of the system for use with a particular patient, or for use during a particular procedure, may be used to identify which sheaths are usable or compatible with that procedure. For example, as illustrated in FIG. 21C, two sheaths are marked by an arrow indicator, while all others are marked by an "X" indicator. This might be the case where the patient is a child, and the two marked sheaths are sized for use with a child, or might be the case where the configured procedure requires certain capabilities (e.g., sheath hardware capabilities, such as balloon dilation or power delivery, or software capabilities enabled for certain sheaths, such as machine learning based object recognition of certain anatomy). In this manner, the display (824) may automatically update when the drawer is opened to clearly indicate which sheath should be mounted to the endoscope (700).

Referring to the ultraviolet light emitter (818) of FIG. 21A, the cabinet (806) may include one or more such emitters positioned to emit light onto exposed surfaces of the endoscopes (700) and sheaths (102) as has been described. This might include two light emitters (818), each positioned within the cabinet (806) above a respective drawer, or a single light emitter (818) positioned above a single drawer (e.g., the sheaths should be stored in a sterile manner already, but the endoscopes (700) may be handled and placed back within the drawer). In some implementations, the inserts (813, 822) may be fully or partially constructed from translucent plastics with high optical transmitting rates, such that the emitted ultraviolet light can reflect within the drawer and reach all surfaces of the sheath (102) and/or endoscope (700). In such implementations, a single ultraviolet emitter (818) may be positioned between the first (810) and second drawer (812) and configured to emit light in all directions, through the light transmissive inserts (813, 822) such that a single ultraviolet light source may be used to emit ultraviolet light onto substantially all of the surfaces of the endoscopes (700) and sheaths (102) stored in both drawers.

Figure 22:
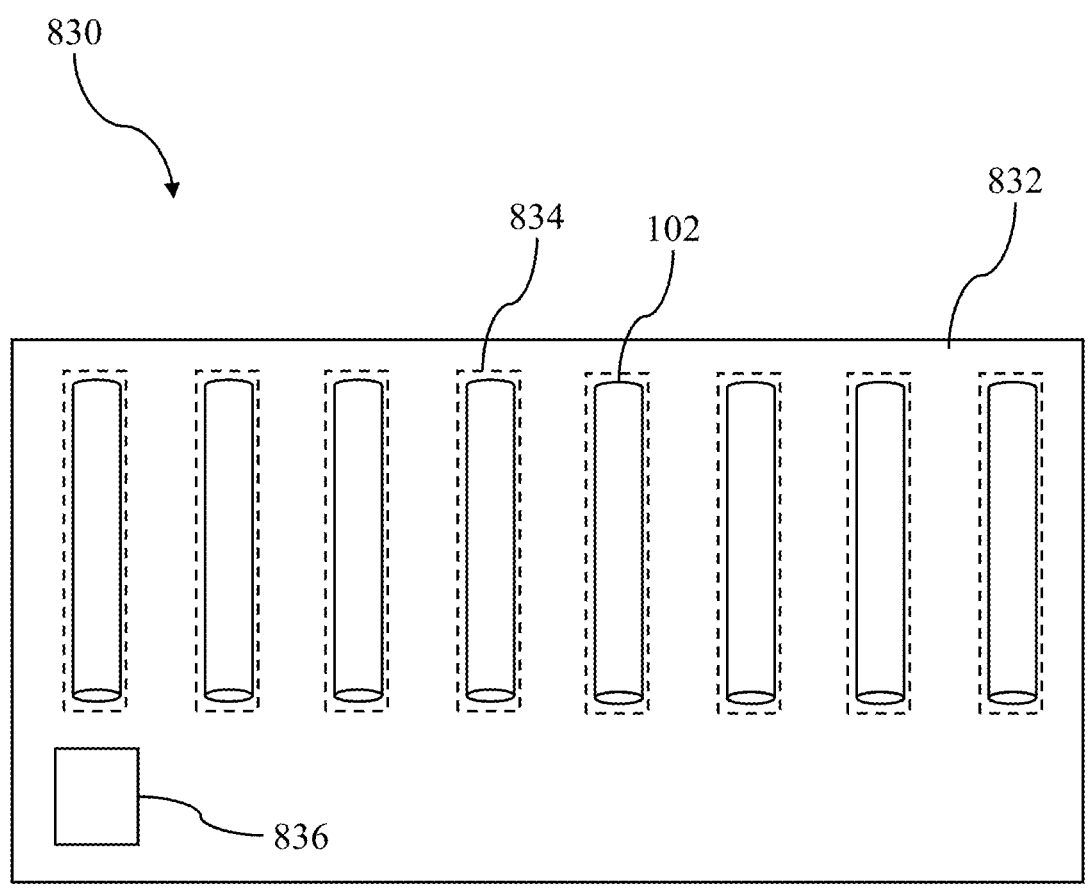
FIG. 22 is a top down view of an exemplary sheath package usable with the system of FIG. 1.

FIG. 22 is a top down view of an exemplary sheath package (830) usable with the system of FIG. 1. The sheath package (830) provides an additional way to access and use sheaths, such as the sheath (102) of FIG. 1 or other sheaths disclosed herein, and may be used instead of or in addition to the cart (800) or other devices. The package (830) includes a body that may be formed of plastic, papers, or other materials, in which a set of sheaths (102) may be removably positioned. Each sheath (102) may be isolated from the others to preserve sterility, and may be sealed to or sealed within the body (832) by a removable seal (834) that may be, for example, a removable adhesive strip, or a plastic membrane that may be cut or punctured to provide access.

In this implementations, it is not necessary for each sheath (102) to include a sheath memory (130) or other integral memory device or communication chip, as a package indicator (836) is instead provided as part of the sheath package (830). The package indicator (836) may be used to enable one or more advanced features of the endoscope (700) in place of the sheath memory (130), as described in FIG. 15 and elsewhere. As an example, the package indicator (836) may itself be a memory chip which couples to the endoscope (700) (e.g., via the port (704) or another data connection, to which it might removably connected, or might be inserted and stored within) to enable certain features, and each usage that enabled such features may decrement a use counter stored on the memory chip (e.g., the implementation of FIG. 22 may provide 8 uses, corresponding to the 8 included sheaths (102)). As another example, the package indicator (836) may be an RFID memory chip or other wirelessly accessed memory device, having a similar function of enabling a feature and maintaining a local usage count corresponding to the number of provided sheaths. As yet another example, the package indicator (836) could be a QR code or other computer readable optical code which may be scanned by the endoscope (700) camera, or another camera, and may enable limited use features. In such an implementation, the endoscope (700) itself may locally track usage associated with the optical code, or may access a remote server to verify or modify usage based upon the optical code.

Usage tracking for basic features of endoscopes disclosed herein, as well as advanced features that may be enabled by a sheath memory or packaged memory chip, are important to prevent misuse, overuse, abuse, or other unsafe uses (e.g., re-use of sheaths that are designed for single use, and are not robust enough to undergo sterilization procedures). The disclosed system may be configured to provide various types of usage tracking, including time limited use (e.g., an advanced feature might be enabled for between 5 and 30 minutes depending upon a particular procedure), activation limited use (e.g., an advanced feature for measuring the cross sectional volume of an airway might be limited to between 2 to 4 uses once activated), and other limitations.

In order to communicate usage tracking to a user of an endoscope such as the endoscope (700), that device might include a multi-color LED indicator, other visual indicator, audio indicator, or other user feedback device that is configured to provide an indication of available usage. As an example, an audio indicator might provide regular audible instructions, by way of a machine simulated voice, indicating the remaining time left, number of uses left, or other limitation on use. As another example, an LED indicator may go through varying stages of display indicating exhaustion of time, activations, or other usage (e.g., a blinking green light might indicate that a sheath needs to be attached, a solid green light indicates the endoscope is ready to use, a solid orange light indicates about 50% of usage left, a solid red light indicates about 25% of usage left, and a blinking red light indicates less than 10% of usage left).

Figure 23A:
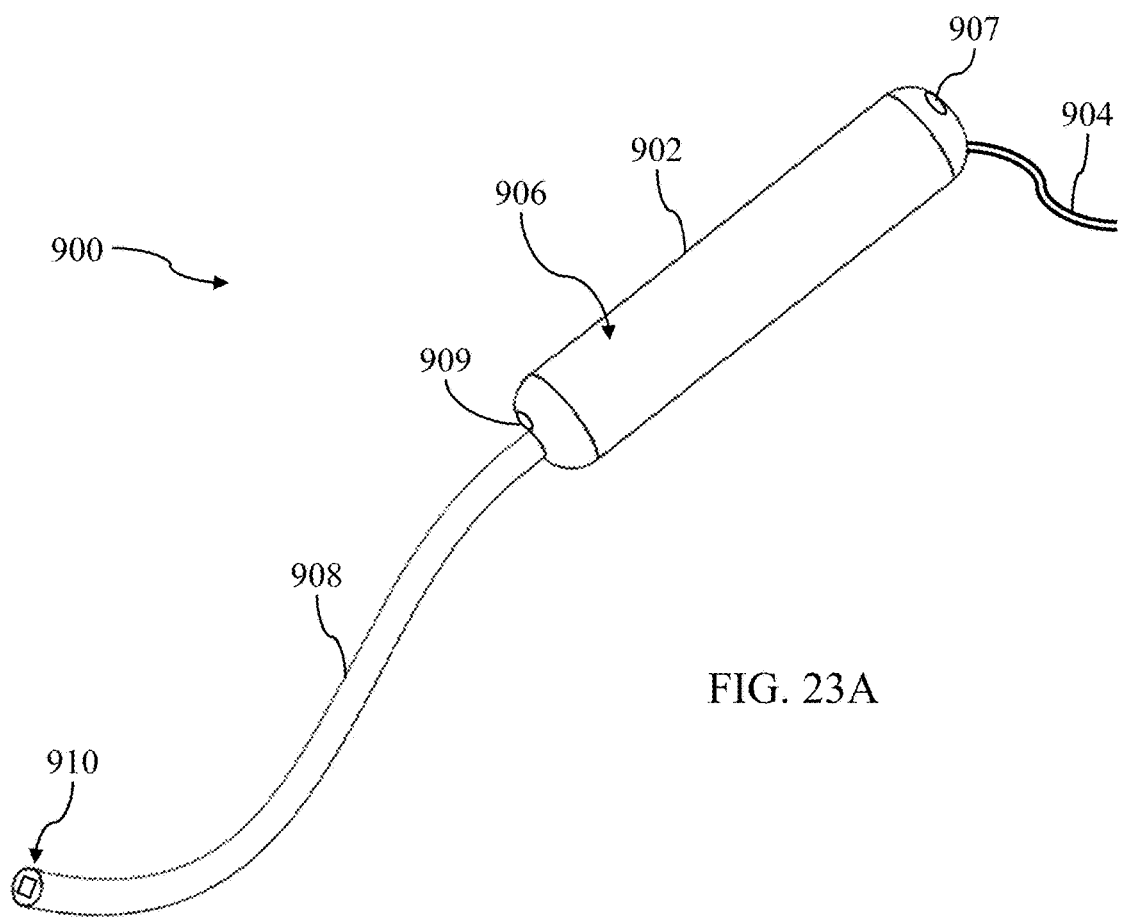
FIG. 23A is a perspective view of an alternate exemplary endoscope that includes a shaft and working channel port.

FIGS. 23A-23D illustrate another example of an endoscope and sheath usable with systems such as that shown in FIG. 1. FIG. 23A is a perspective view of an alternate exemplary endoscope (900) that includes a shaft (908) and a working channel port (909). The working channel port (909) defines an opening to a channel (906) that passes through a body (902) of the endoscope (900) and terminates at a channel opening (907) to the rear of the body (902), just above a cable (904) that provides power and/or data communication between the endoscope (900) and a power source or data source.

A distal tip (910) of the shaft (908) may include any of the components or features associated with distal tips of endoscopes, sheaths, or both, as disclosed herein. In some implementations, the shaft (908) may be flexible or malleable, such that it may be formed into a desired shape (e.g., by hand, or with a forming tool), while in other implementations the shaft may be rigid and pre-formed into a desirable shape or configuration for specific procedures. Where flexible, the shaft (908) provides a malleable, semi-rigid interface for positioning the distal tip (910) during a procedure, and also contains interfaces (e.g., cables, channels) allowing for power (e.g., to power LEDs or cameras), data (e.g., images from a camera), irrigation, and other resources to be provided at or received from the components of the distal tip (910).

Figure 23B:
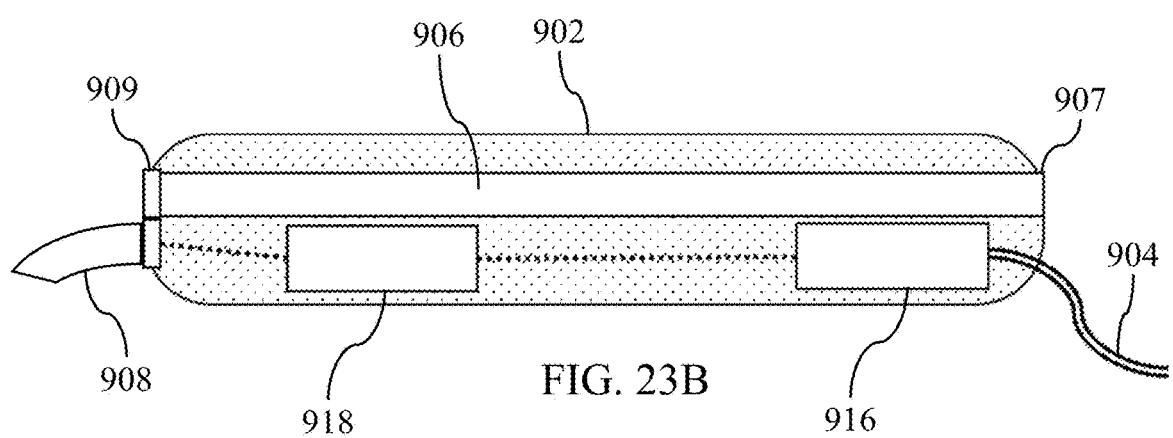
FIG. 23B is a schematic diagram illustrating a cross sectional view of an exemplary body of the endoscope of FIG. 23A.

FIG. 23B is a schematic diagram illustrating a cross sectional view of an exemplary body of an endoscope such as that shown in FIG. 23A. The channel (906) is more clearly seen passing through the body (902) of the endoscope (900). Deployable flexible surgical instruments that are used during minimally invasive surgical procedures may be inserted into the channel opening (907) and advanced through the channel (906) until an operative tip of the instrument exits the channel (906) via the working channel port (909). As will be shown and described in more detail below, a sheath configured to be coupled to the working channel port (909) and the shaft (908) is positioned to receive and guide the operative tip of an advancing surgical instrument to a point near the distal tip (910) of the endoscope (900) for use at a surgical site. The body (902) also contains a control board (918) and a procedure board (916), having a similar function and features as the commonly named components described in the context of FIG. 17C above. As with other endoscopes, the body (902) of the endoscope (900) may also contain additional components such as batteries, wireless communication devices, memory chip reading devices, and other components as may be required to perform the features and functions of endoscopes described herein.

Figure 23C:
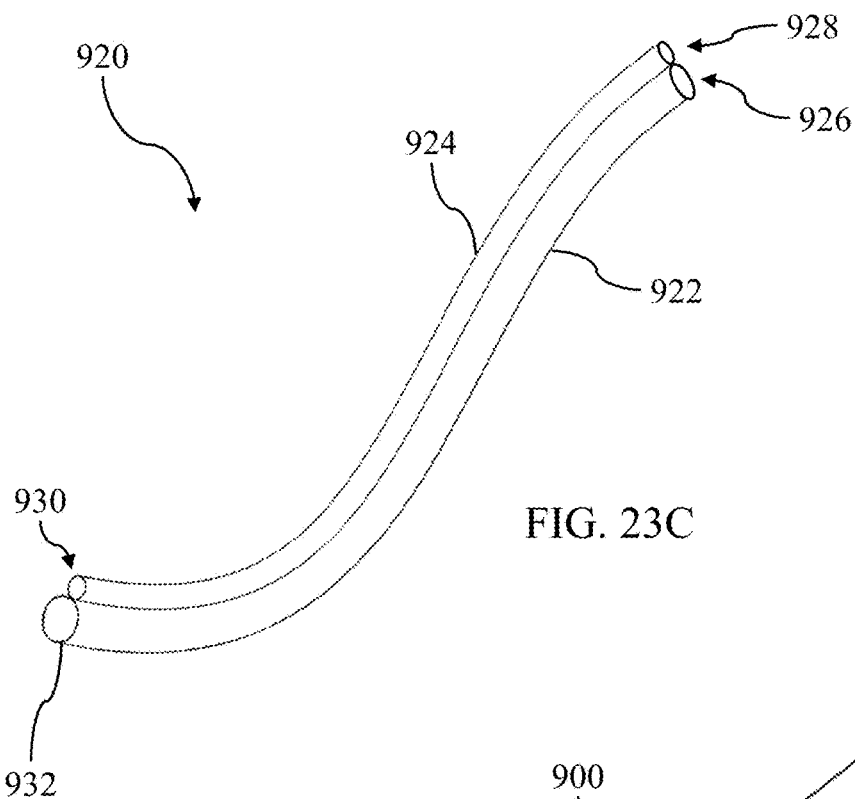
FIG. 23C is a perspective view of an exemplary flexible sheath usable with the endoscope of FIG. 23A.

FIG. 23C is a perspective view of an exemplary flexible sheath (920) usable with an endoscope such as the endoscope (900) of FIG. 23A, and which may be referred to as a dual sheath. The flexible sheath (920) includes an endoscope sheath (922) and a working channel sheath (924). The flexible sheath may be comprised of resilient flexible materials such as plastics or polymers, and may also include metals (e.g., for integrated electrical or data connections), glass or rigid plastics (e.g., lenses and optical interfaces). The endoscope sheath (922) is sized to snugly fit the shaft (908) and provide a disposable sterile barrier that may be fitted to the endoscope (900) during a procedure, as has been described in relation to other sheath disclosed herein. The shaft (908) distal tip (910) may be inserted into a proximal opening (926) of the sheath (920), and the shaft (908) may be advanced into the endoscope sheath (922) until the proximal opening (926) contacts the body (902). In some implementations, the endoscope sheath (922) may couple to the body using a friction fit or mechanical fit (e.g., a semi-flexible ridge that expands around a complementary rigid tab or edge of the body (902)), a magnetic fit (e.g., a magnetic coupling between magnetic components), or other fitting type.

When the endoscope sheath (922) is fully seated onto the shaft (908), a port connector (928) of the working channel sheath (924) will engage with the working channel port (909) and created a sealed connection between the working channel sheath (924) and the channel (906). A distal end of the working channel sheath (924) includes a work opening (930) through which an operative tip of a deployed surgical instrument may access anatomy at a surgical site. A distal end of the endoscope sheath (922) includes an optical interface (932), which may be a substantially transparent surface, or may include lenses and more advanced optics as described herein.

Figure 23D:
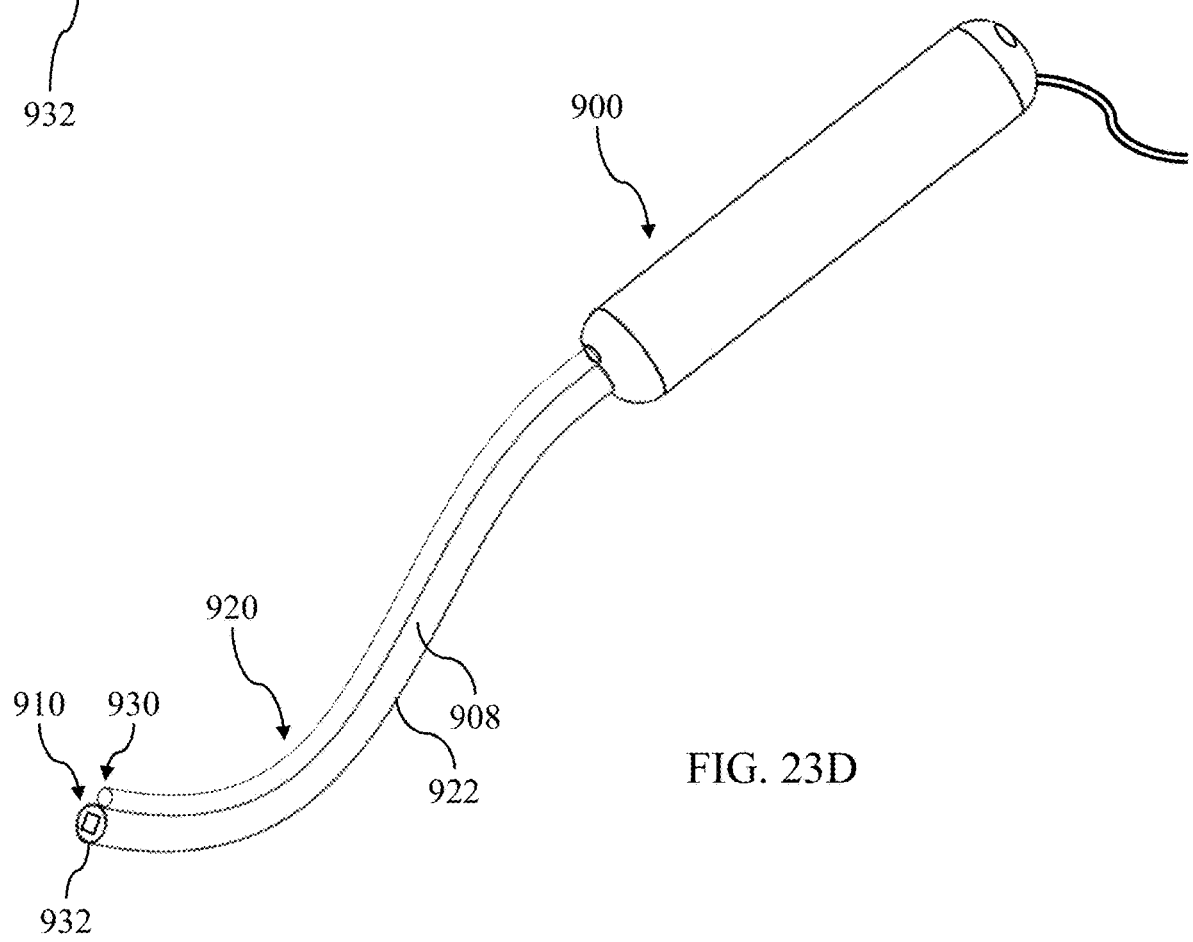
FIG. 23D is a perspective view of the endoscope of FIG. 23A coupled with the sheath of FIG. 23C.

FIG. 23D is a perspective view of the endoscope (900) of FIG. 23A coupled with the sheath (920) of FIG. 23C. As can be seen, the shaft (908) of the endoscope (900) is fully seated within the endoscope sheath (922). In isolation, the sheath (920) is flexible and will generally be biased towards the shape in which it was formed (e.g., linear, or a curve such as shown in FIG. 23C). However, when fitted to the shaft (908), the endoscope sheath (922) will confirm to the shape of the shaft (908) as it is flexed or manipulated during a procedure. Since the working channel sheath (924) is coupled to the endoscope sheath (922) along its length, the working channel sheath (924) will similar conform to the shape of the shaft (908) during a procedure. In this manner, the work opening (930) will always be positioned proximally to the distal tip (910) and optical interface (932), such that a surgical instrument may be readily advanced to the work opening where it may be operated in view of the cameras, and with the benefit of any LEDs, of the distal tip. As with other sheaths disclosed herein, the sheath (920) may include some or all of the features herein disclosed in relation to sheaths, including memory chips for usage tracking and storage of procedure data, integrated LEDs, irrigation channels, suction channels, balloon dilation, and other such features.

With reference to the distal tip (720), in some circumstances the light projected from the LEDs (724) through a sheath such as the sheath (102) may result in lighting artifacts at the sheath tip. Even where the sheath lens through which light is projected is highly transmissive, light may reflect off imperfections and "bleed" into the edges of images captured by a centrally positioned camera. While central focal points of the image may not be influenced by such light bleeding, details at image edges may be lit inconsistently relative to other portions of the image, or may be entirely obscured in some cases. This may negatively impact both images captured and viewed by a surgeon using the endoscope in real time, but may also negatively impact the usability of captured image data for automated identification of anatomical features, for artificial intelligence or machine learning training processes, and for other purposes.

Figure 24A:
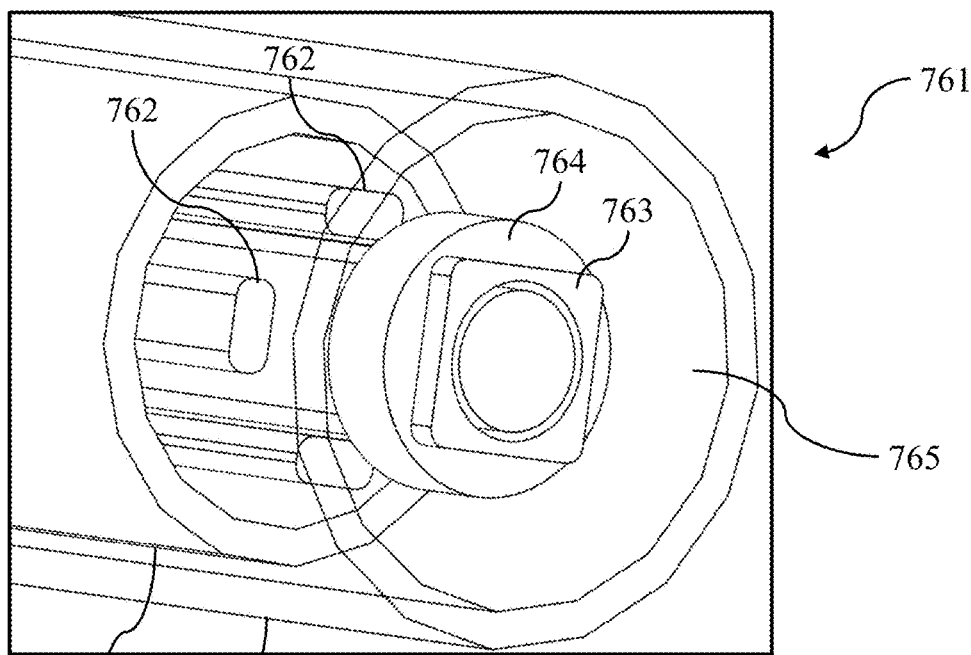
FIG. 24A is a perspective view of a distal tip of an endoscope that includes an optical shield.

FIGS. 24A through 27B show embodiments of endoscopes that include features for the prevention of light reflection, light glare, light bleeding, and other lighting artifacts. Features of the shown implementations may be combined with any of the disclosed endoscopes, including the endoscope (700). Referencing that endoscope as an example, FIG. 24A shows a distal tip (761) of the endoscope shaft (712) with the endoscope sheath (102) installed on the shaft (712) and over the distal tip (761). A set of LEDs (762) are positioned at a set off from the distal tip (761), with a camera (763) positioned at the distal tip (761), and an optical shield (764) positioned between the set of LEDs (762) and the camera (763). A lens (765) of the sheath (102), through which light is projected and images are captured, may be positioned in front of the camera (763) such that it is in contact with the camera (763) or separated from the camera (763) by a small distance (e.g., fractions of a millimeter).

Figure 24B:
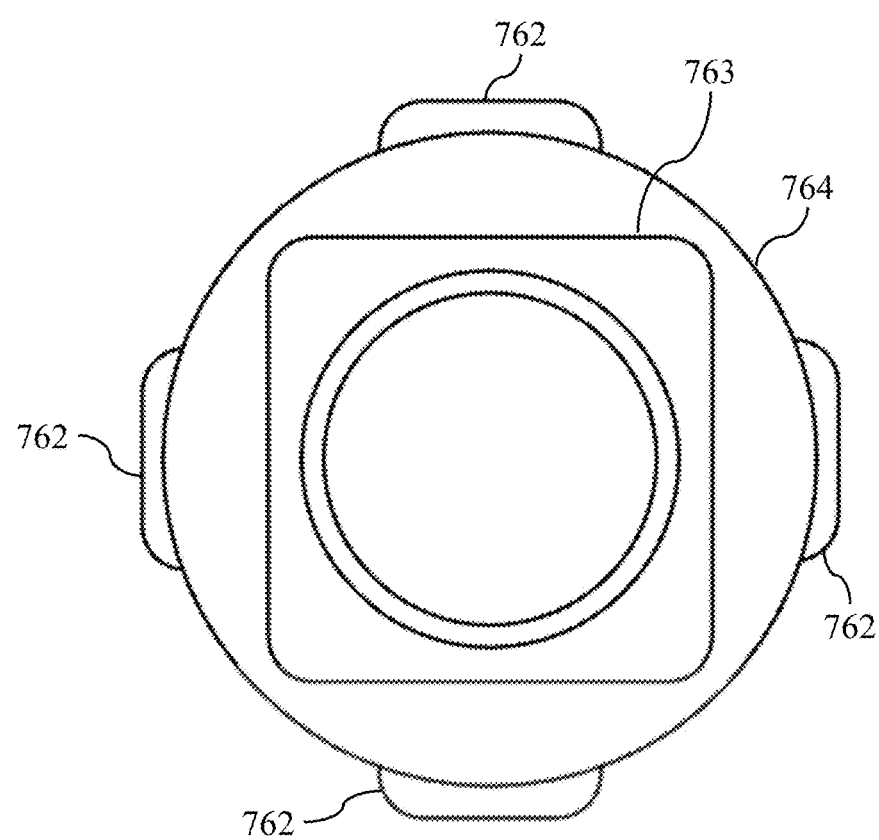
FIG. 24B is a front elevation view of the distal tip of FIG. 24A.

The presence of the optical shield (764) serves to prevent a portion of the light projected by the set of LEDs (762) from striking the lens (765) of the sheath (102), in particular, light emitted from the LEDs (762) that would otherwise strike the lens (765) at a perpendicular angle, proximate to the optical field of view of the camera (763). This is clearly illustrated in FIG. 24B, which shows a front elevation view of the distal tip (761), with the sheath (102) removed. As can be seen, the optical shield (764) extends into and at least partially obstructs the path of light projected from each LED (762) past the camera (763) and towards the lens (765). While the optical shield (764) is shown in FIG. 24B as obstructing around 50% of the LEDs (762) facing towards the lens (765), it should be understood that the size and shape of the optical shield (764) may be varied to provide a differing level of obstruction (e.g., obstruction between about 25% and about 100% may provide desirable mitigation of lighting artifacts). An optical shield such as that shown in FIG. 24B advantageously provides a circular obstruction which mirrors the circular shape of the camera (763) field of view.

Figure 25A:
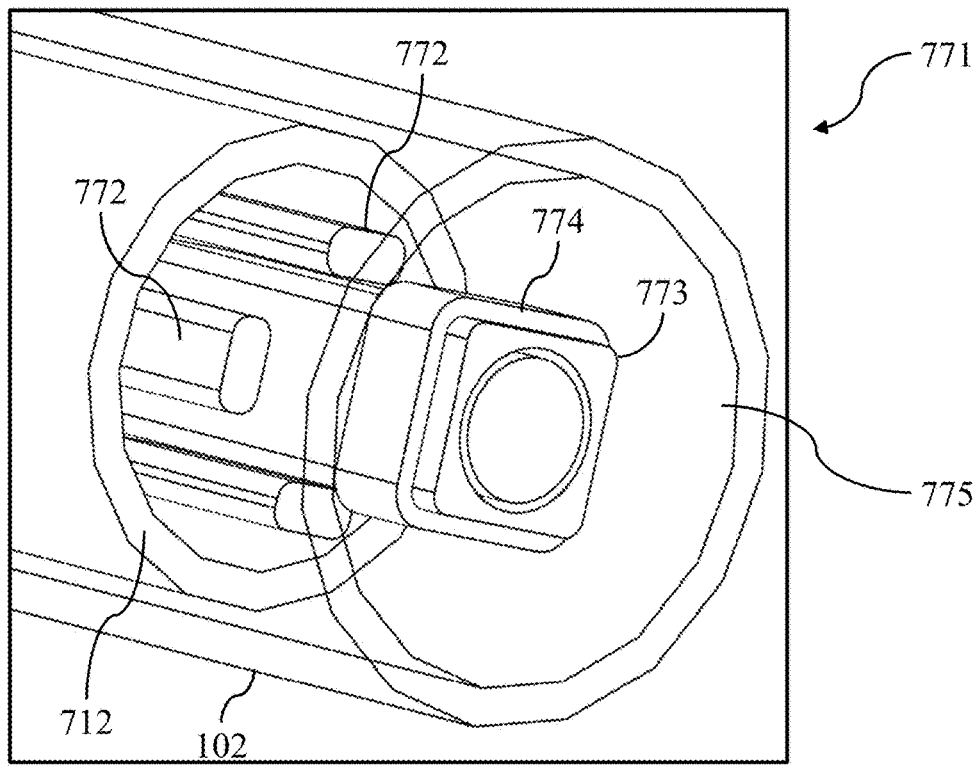
FIG. 25A is a perspective view of an alternate distal tip of an endoscope that includes an optical shield.
Figure 25B:
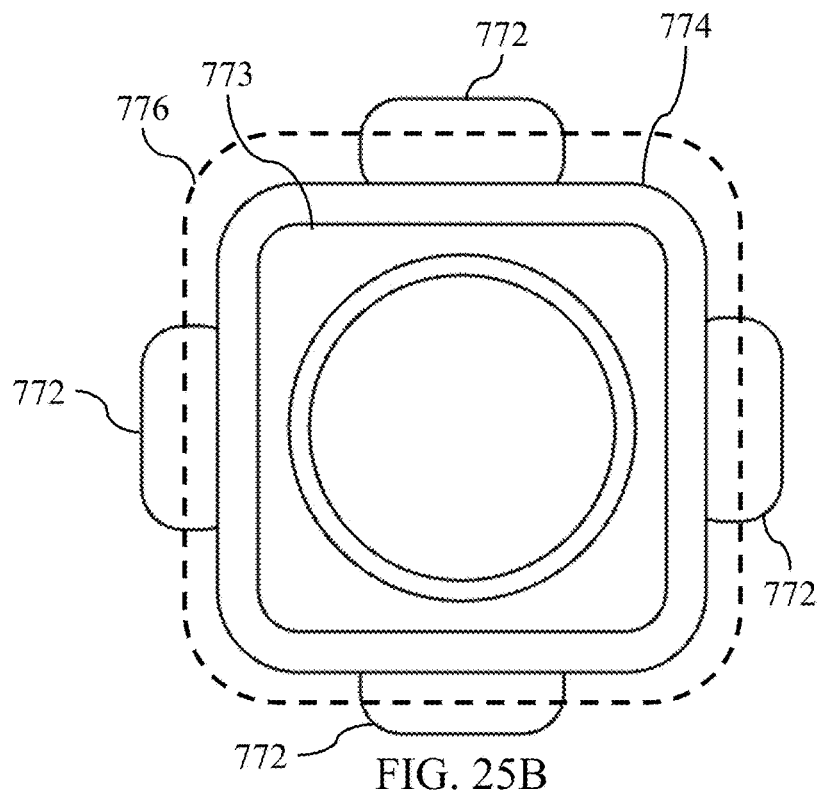
FIG. 25B is a front elevation view of the distal tip of FIG. 25A.

FIG. 25A shows an alternate distal tip (771) having similar features and functions as the distal tip (761). A set of LEDs (772) are positioned at a set off from the distal tip (771), with a camera (773) positioned at the distal tip (771), and an optical shield (774) positioned between the set of LEDs (772) and the camera (773). A lens (775) of the sheath (102), through which light is projected and images are captured, may be positioned in front of the camera (773) such that it is in contact with the camera (773) or separated from the camera (773) by a small distance (e.g., fractions of a millimeter). The optical shield (774) functions similarly to the optical shield (764) described in the context of FIG. 24A, and illustrates a variable shape (e.g., a square with soft edges) and size (e.g., about 25% of the LEDs (772) are obscured by the optical shield (774)), as illustrated in FIG. 25B. An alternate size (776) of the optical shield (774) is illustrated as a dashed line, which provides about 50% or more obfuscation of the LEDs (772), and some implementations may fully obstruct the path of light from the LEDs (772) to the lens (775).

Figure 26A:
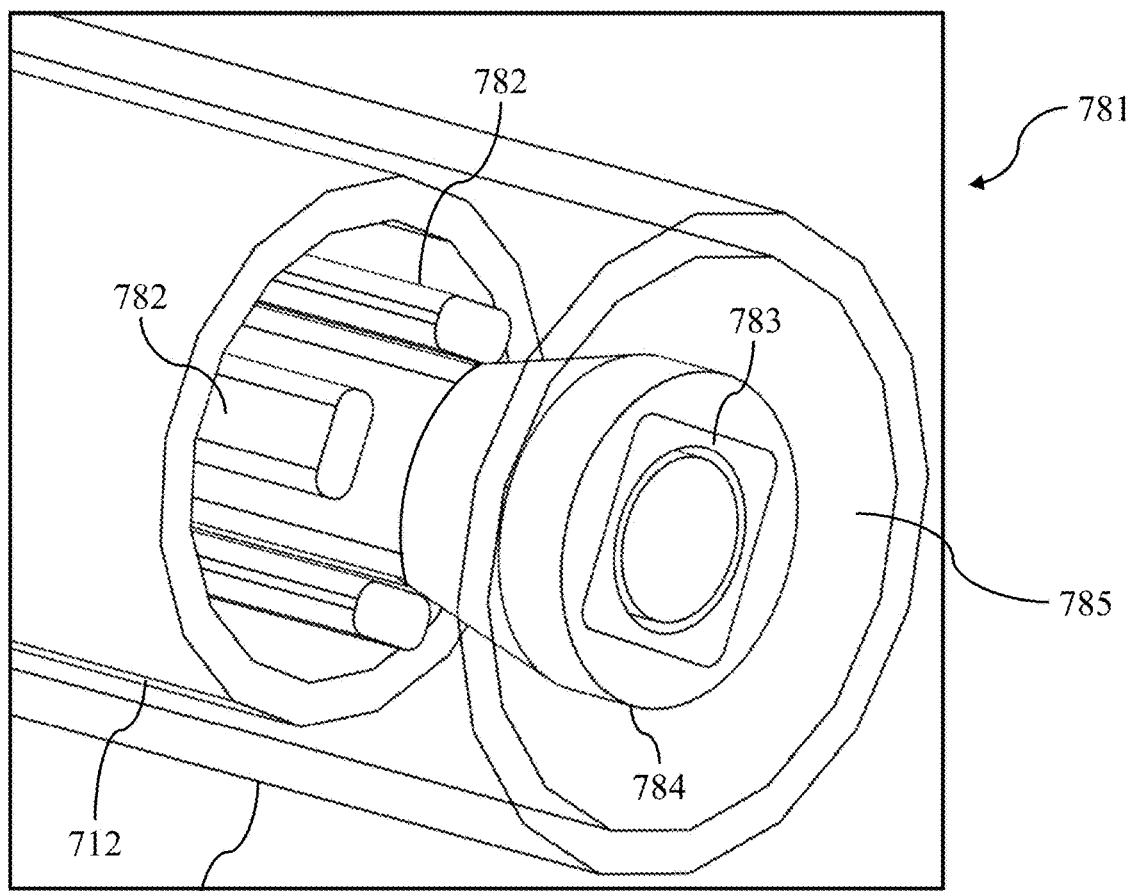
FIG. 26A is a perspective view of another alternate distal tip of an endoscope that includes an optical shield.
Figure 26B:
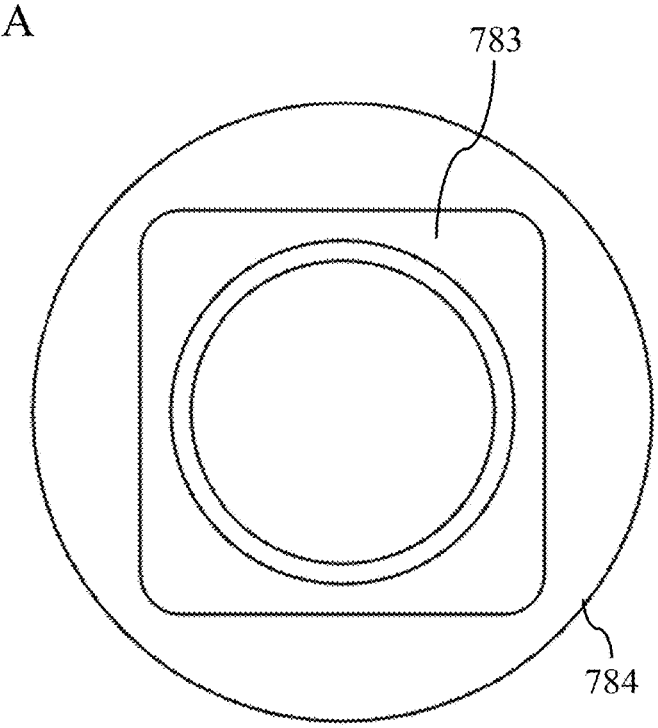
FIG. 26B is a front elevation view of the distal tip of FIG. 26A.
Figure 26C:
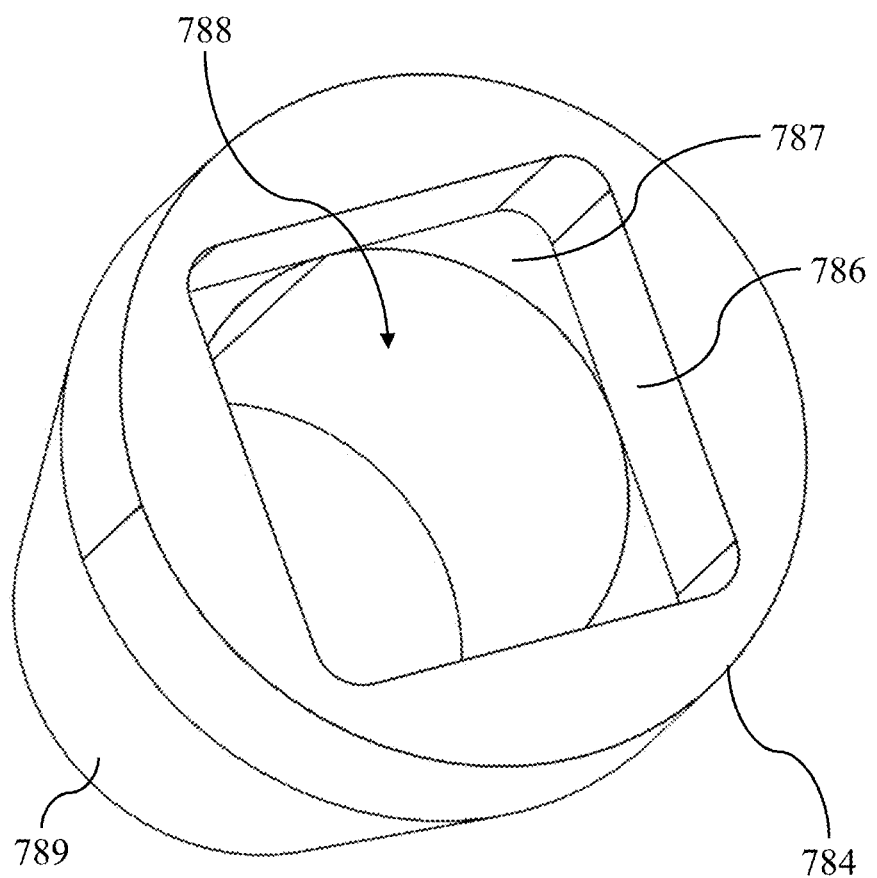
FIG. 26C is a perspective view of the optical shield of FIG. 26A.

FIG. 26A shows an alternate distal tip (781) having similar features and functions as the distal tip (761). A set of LEDs (782) are positioned at a set off from the distal tip (781), with a camera (783) positioned at the distal tip (781), and an optical shield (784) positioned between the set of LEDs (782) and the camera (783). A lens (785) of the sheath (102), through which light is projected and images are captured, may be positioned in front of the camera (783) such that it is in contact with the camera (783) or separated from the camera (783) by a small distance (e.g., fractions of a millimeter). The optical shield (784) functions similarly to the optical shield (764) described in the context of FIG. 24A, as can be seen in FIG. 26B, with the path of the LEDs (782) fully obstructed by the optical shield (784). FIG. 26C shows the optical shield (784) in isolation from the rest of the distal tip (781). As can be seen, the optical shield (784) defines a channel (788) through which a portion of the internal structure of the shaft (712) may pass. A lip portion (787) can be seen which the edges of the camera (783) rest upon when positioned within the channel, and a sidewall (786) extends from the lip portion (787) a height that corresponds to, or may exceed, the height of the camera (763) body within the optical shield (784) (e.g., this may also be referred to as a hood or a shroud). A lower portion (789) of the optical shield (784) that faces the LEDs (782) is angled such that projected light strikes the optical shield (784) at a non-perpendicular angle, which may cause the light to reflect outwards through a sidewall of the sheath (102) rather than reflecting back towards the source.

Figure 27A:
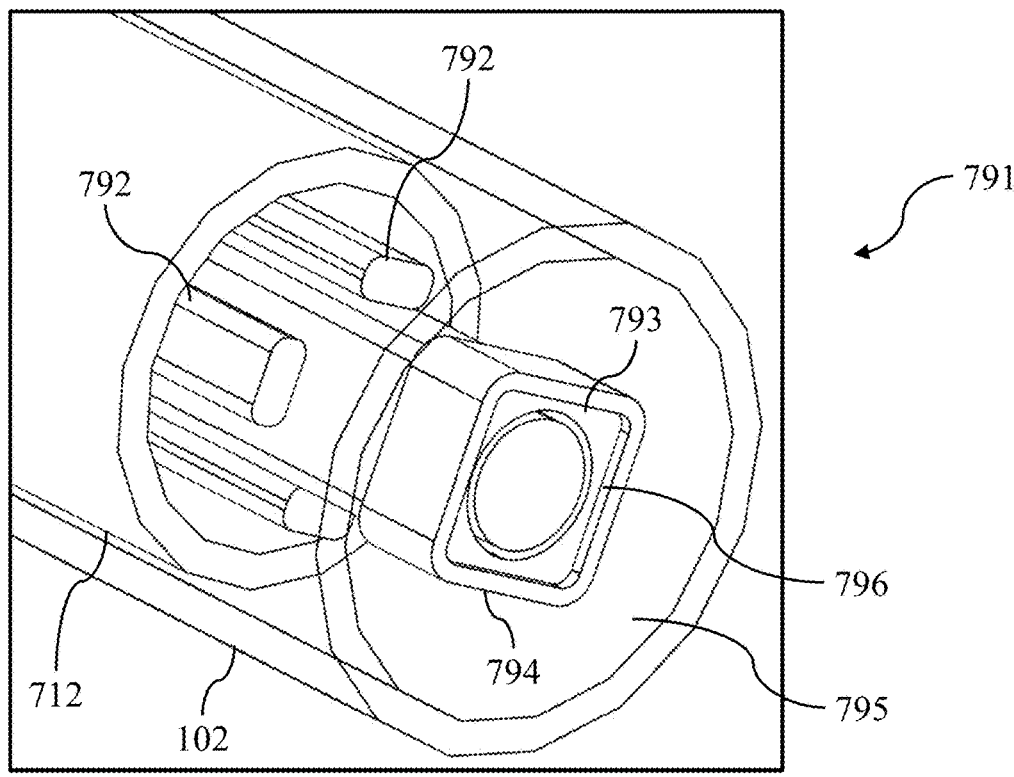
FIG. 27A is a perspective view of yet another alternate distal tip of an endoscope that includes an optical shield.
Figure 27B:
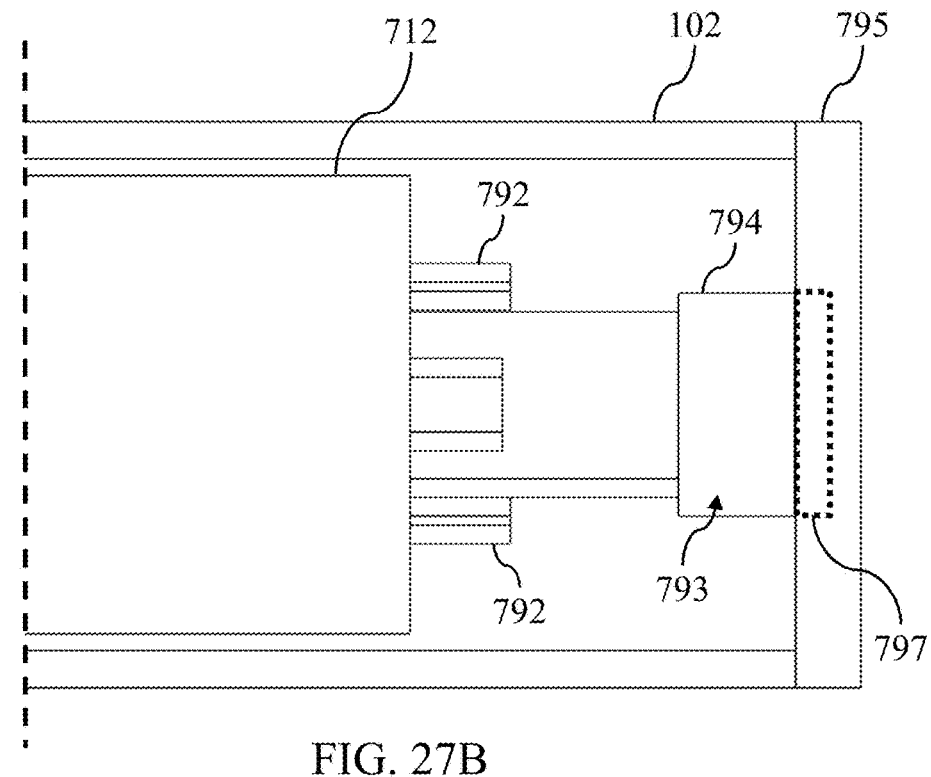
FIG. 27B is a side elevation view of the distal tip of FIG. 27A.

FIG. 27A shows an alternate distal tip (791) having similar features and functions as the distal tip (761). A set of LEDs (792) are positioned at a set off from the distal tip (791), with a camera (793) positioned at the distal tip (791), and an optical shield (794) positioned between the set of LEDs (792) and the camera (793). A lens (795) of the sheath (102), through which light is projected and images are captured, may be positioned in front of the camera (793) such that it is in contact with the camera (793) or separated from the camera (793) by a small distance (e.g., fractions of a millimeter). The optical shield (794) functions similarly to the optical shield (764) described in the context of FIG. 25A, but additionally includes a sidewall (796) that extends beyond the edge of the camera (793) towards the lens (795) such that the camera is set back within the optical shield (794). The sidewall (796) may extend all the way to the lens (795), such that the camera (793) field of view and lens (795) are fully isolated from projected light within the sheath (102) (e.g., both directly projected light and reflected light are prevented from striking the central portions of the lens (795)). FIG. 27B shows a side profile view of the distal tip (791), illustrating that the optical shield (794) is in contact with the interior face of the lens (795). In some implementations, the lens (795) may have a slot (797), illustrated by dashed lines in FIG. 27B, corresponding to the shape and position of the optical shield (794) such that the shield may be in contact with, and extend a depth into the lens (795).

With each of the optical shield examples described above, the shield may define an internal channel (e.g., such as the channel (788)) through which a portion of the structure of the shaft (712) passes, and which may receive and hold a portion of the camera. In some implementations, any of the optical shields may be comprised of a soft, flexible, or pliable material (e.g., rubber, foam) that both absorbs vibrations to mitigate camera instability, and that prevents damaging contact between the sheath (102) and the distal tip during installation and use of the sheath (102) (e.g., such as where over insertion or a strong force causes the distal tip to strike and scratch or damage the lens, or vice versa). In some implementations, a surface of the optical shield may be treated with, covered with, or comprised of materials having particular reflective properties. As an example, some optical shields may include a non-reflective (e.g., black, or other absorptive color or surface) surface. With reference to FIG. 24A, where the optical shield (764) includes a non-reflective surface, light striking the shield will be reflected to a minimal degree. In other examples, an optical shield may include a highly reflective surface (e.g., white, mirrored). With reference to FIG. 26C, where the lower portion is a reflective surface, light projected from the LEDs will strike the lower portion (789) at a non-perpendicular angle and will be reflected outwards from the sheath (102). In this manner, reflected light may improve ambient lighting around the distal tip without reflecting directly into the lens.

Figure 28:
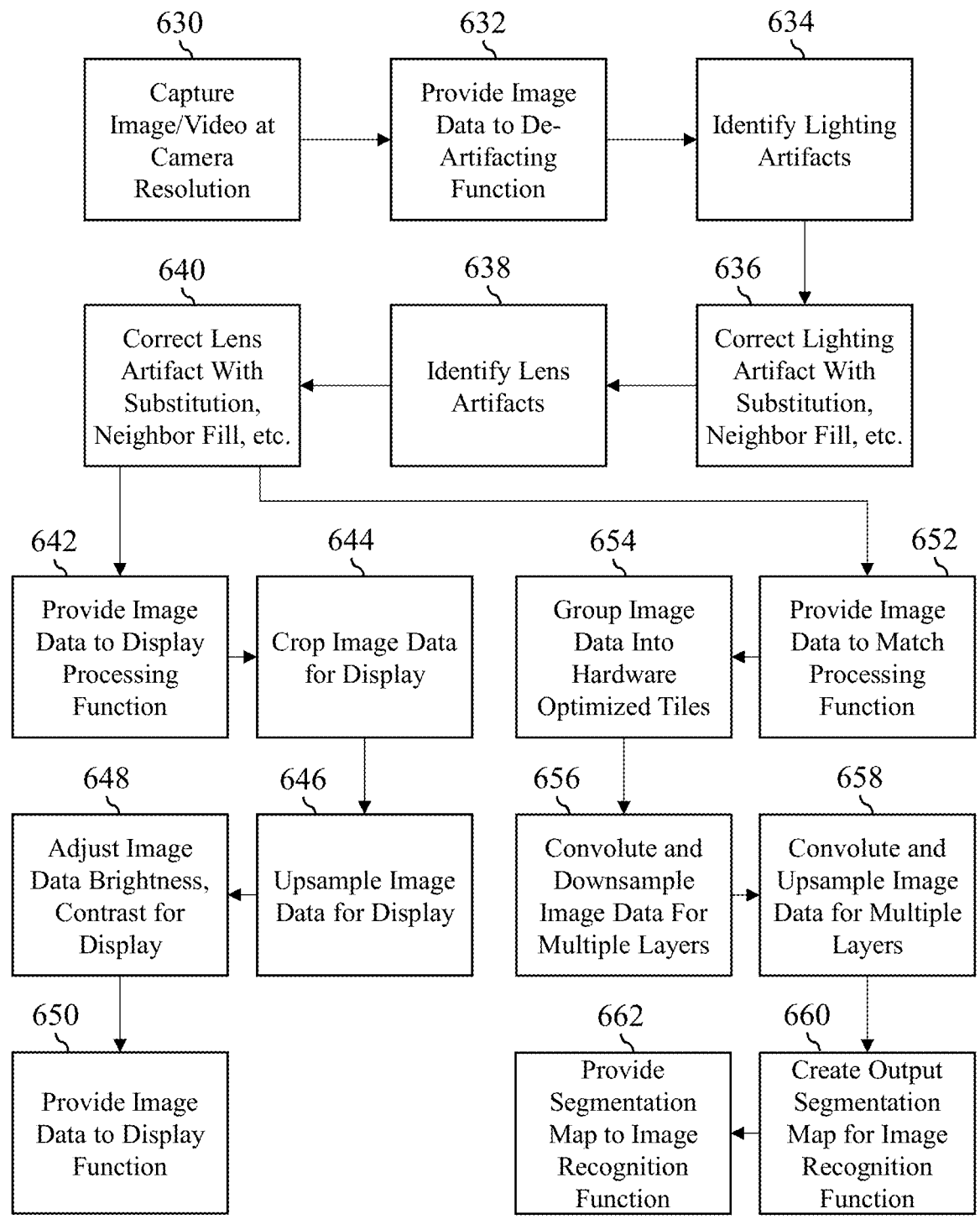
FIG. 28 is a flowchart of an exemplary set of steps that may be performed to provide local and/or remote image processing to improve image characteristics for display and image recognition.

As another example of image processing that may be performed with captured images, FIG. 28 shows steps that may be performed to provide local and/or remote image processing to improve image characteristics for display and image recognition. The steps of FIG. 28 may be performed by one or more devices in varying implementations, and for example may be performed by the image processor (104), remote server (106), user device (108), processor (160), control board (718), or other processors or devices.

As images are captured (630) by an endoscope camera such as those disclosed herein, they will initially be captured as raw image data having a resolution, format, color depth, and other visual characteristics determined by the source camera. This image data may also contain digital and other image artifacts, such as blooming, chromatic aberrations, moire, and image noise, and particularly for endoscopic imaging may also contain lighting artifacts related to endoscopic lighting, and lens artifacts related to obstruction of the lens (e.g., by debris or biological materials, fogging, liquid droplets, and other materials that may be present in the endoscope environment).

To address artifact issues, the system may be configured to provide (632) captured image data to an image processing function that is configured to mitigate the effect of artifacts on the image data, and to produce image data with improved characteristics for display to users during an endoscope procedure and for advanced image analyses such as object recognition or pattern recognition, such as may be performed by, for example, an appropriately configured machine learning, neural network, artificial intelligence, or expert module.

The de-artifacting function (632) may itself include one or more appropriately configured machine learning, neural network, artificial intelligence, or expert modules that trained or configured to identify particular types of artifacts within the image data, and mitigate identified artifacts. In some implementations, this may include using training data that includes annotated images of anatomy captured by the same or similar source endoscope, while viewing the same or similar anatomy and/or performing the same or similar procedure, and may include annotated images that both include and do not include the particular artifact that is being identified. Training data such as the above provides useful inputs for identifying artifacts (e.g., such as many endoscopic images that are affirmatively known to include a particular artifact) but also for mitigating artifacts (e.g., such as many endoscopic images that are affirmatively known to not include a particular artifact, and so would contain pixel groupings or other image data that can be substituted or interpreted into obscured portions of another image).

The de-artifacting function (632) may be performed by one or more different devices or processors in varying implementations. As one example, the de-artifacting function (632) may be performed by the control board (718) of the endoscope (700), and may be performed in real time as image data is captured, such that the output image data of the endoscope (700) has already been pre-processed to mitigate the effect of artifacts prior to being displayed to a surgeon or other practitioner during the endoscopic procedure, and prior to performing any advanced image processing, such as anatomical feature or state recognition, as has been described above.

In addition to performing conventional de-artifacting tasks, the de-artifacting function may be configured to identify (634) lighting artifacts as affected groups of pixels within the image data, and to correct (636) those lighting artifacts by substituting image data that is suggested or provided by, for example, an appropriately configured machine learning, neural network, artificial intelligence, or expert module, or may provide substitute data for the affected pixel groups by using a neighbor-fill approach (e.g., nearest-neighbor) or other pixel filling approach that relies on pixel data from elsewhere in the image. The de-artifacting function may also identify (638) pixel groups that are affected by lens or optical interface artifacts, and may correct (640) those lens artifacts by substitution (e.g., using substitute pixel groups provided by an appropriately trained or configured module, as has been described), neighbor-fill, or other techniques as previously described.

Figure 29A:
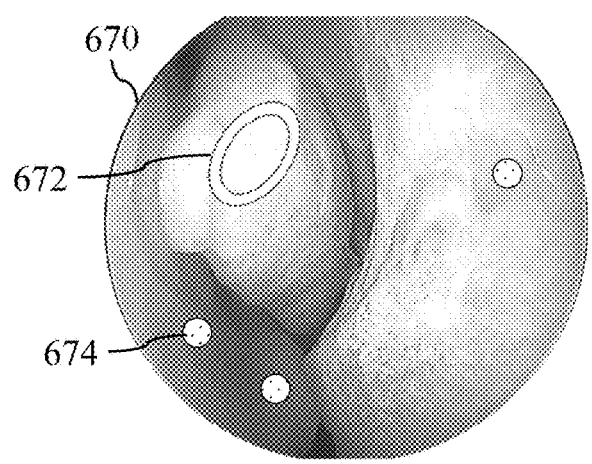
FIGS. 29A and 29B show image data before and after artifact image processing according to steps such as those illustrated in FIG. 28.
Figure 29B:
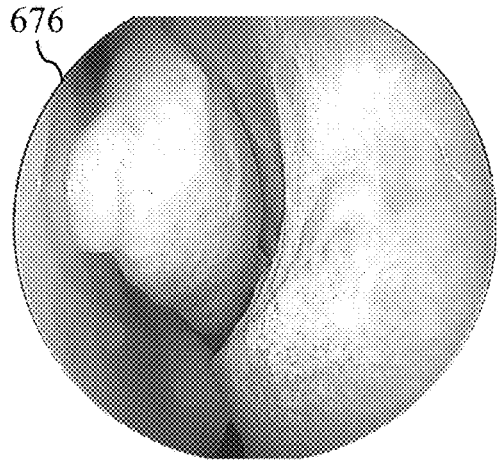

FIG. 29A shows an example of image data (670) that contains a number of artifacts, including a lighting artifact (672) in the form of light of an endoscope illuminator reflected off an anatomical surface, which typically appears as a substantially white or very bright hollow ring that partially or completely obscures the anatomical surface (e.g., tissue color, type, etc.) over which it appears. The image data (670) also includes several lens artifacts (674) caused by liquid droplets or other debris on the endoscope lens (e.g., such as the lens (144) of a sheath, or a lens of the endoscope camera itself). The appearance of lens artifacts (674) will vary, but they may complete obscure a portion of the image data, may blur a portion of the image data, or may catch and diffract reflected light such that they appear as an obstructed or blurred portion that also includes a light halo or other light artifact. FIG. 29B shows an example of image data (670) after de-artifacting to identify and mitigate light and lens artifacts, in which the light artifact (672) is substantially or entirely invisible (e.g., due to pixel substitution or neighbor fill techniques), and the lens artifacts (674) are also substantially or entirely invisible (e.g., due to pixel substitution or neighbor fill techniques).

The depicted example of de-artifacting may be performed by an artificial intelligence module that is trained using a training dataset that includes a plurality of annotated images of anatomy that do not include light artifacts or lens artifacts, and a plurality of annotated images of anatomy that do include light artifacts or lens artifacts. In some implementations, this training dataset may include pairs of annotated images captured from substantially the same perspective, which may include capturing a first image of anatomy from a perspective, and then immediately operating an LED illuminator to increase or otherwise change light output and create a reflection, halo, or other light artifact, or immediately operating a saline spray to apply liquid droplets to an optical interface of the endoscope, and capturing a second image of anatomy from substantially the same perspective. In some implementations, the system may be configured to operate in a training data collection mode in which a single user input (e.g., button click, voice command, or other user control input) causes the endoscope to capture the first image, create the light or lens artifact (e.g., projecting light, emitting saline droplets) and capture the second image, partially or fully annotate each image (e.g., labeling each image as a type such as clean, light artifact, or lens artifact, identifying a pixel group of a light artifact or lens artifact in the second image), and save each image to a corresponding training dataset.

Figure 29C:
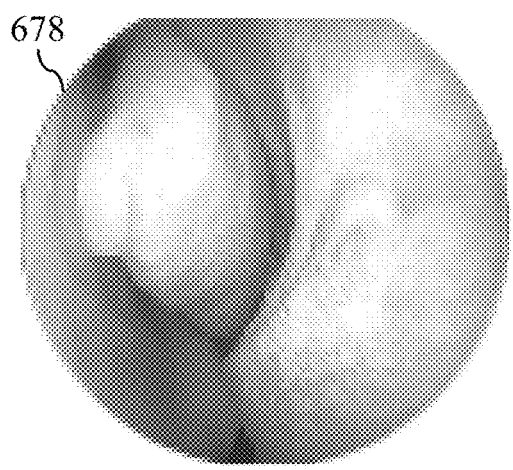
FIGS. 29C and 29D show image data before and after upsampling image processing according to steps such as those illustrated in FIG. 28.
Figure 29D:
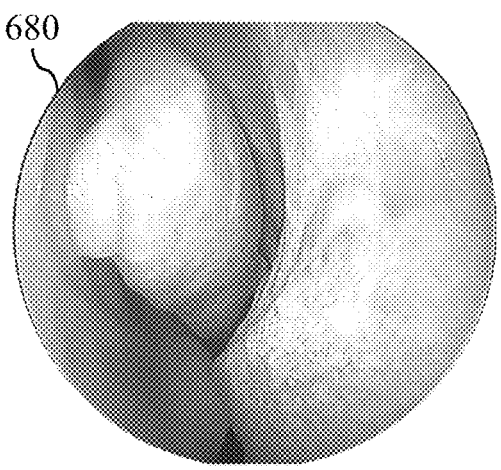
Figure 29E:
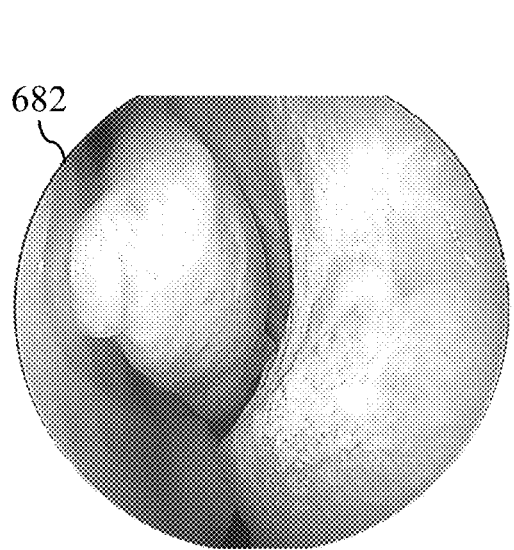
FIGS. 29E and 29F show image data before and after display image processing according to steps such as those illustrated in FIG. 28.
Figure 29F:
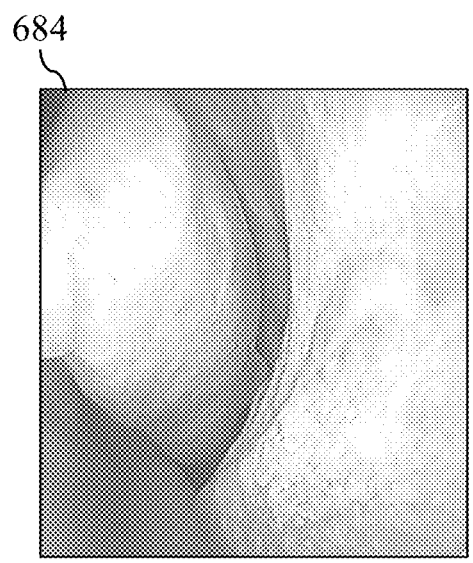
Figure 29G:
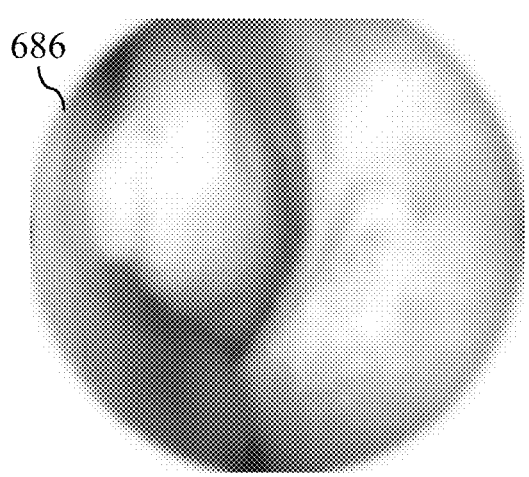
FIGS. 29G and 29H show additional examples of image data before and after artifact image processing according to steps such as those illustrated in FIG. 28.
Figure 29H:
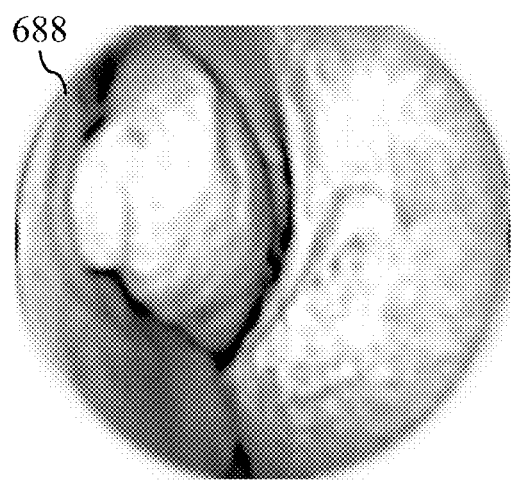

As additional example of de-artifacting, FIG. 29G shows an example of image data (686) that that includes a lens artifact in the form of a misting or fogging of the lens or optical interface, such as may result from humidity, condensation, or moisture in other forms. As opposed to a loss of detail and pixelization due to low resolution, the image data (686) affected by a fogged optical interface shows a loss of detail due to generalized blurriness/softening of detail while still retaining a standard resolution. FIG. 29H shows an example of image data (688) after de-artifacting to identify and mitigate the lens artifacts caused by fogging of the optical interface. The modified image data (688) emphasizes edges and surface textures that are blurred but apparent in the original image data (686). While the modified image data (688) may exhibit some loss or alteration of color, surface texture, and precise edge details (e.g., as compared to an image captured without fogging, such as the image data (682) of FIG. 29E), the sharper depiction of distinct anatomical structures is advantageous for both display to a surgeon during a procedure, and for further image analyses (e.g., object recognition or other machine vision analyses) by an appropriately configured machine learning, neural network, artificial intelligence, or expert module.

The depicted example of de-artifacting may be performed by an artificial intelligence module that is trained using a training dataset that includes a plurality of annotated images of anatomy that do not include fog lens artifacts, and a plurality of annotated images of anatomy that do include fog lens artifacts. In some implementations, this training dataset may include pairs of annotated images captured from substantially the same perspective, which may include capturing a first image of anatomy from a perspective, and then immediately operating a saline mister to fog an interior or exterior surface of the lens or optical interface and capturing a second image of the anatomy from substantially the same perspective. In some implementations, the system may be configured to operate in a training data collection mode in which a single user input (e.g., button click, voice command, or other user control input) causes the endoscope to capture the first image, create the lens artifact and capture the second image, partially or fully annotate each image, and save each image to a corresponding training dataset.

Returning to FIG. 28, the de-artifacted image data may then be provided (642) to a display processing function, which is configured to perform additional image processing so that the image data may be displayed on a particular device, and may also be provided (652) to a match processing function, which is configured to perform additional image processing so that the image data may be provided to an appropriately configured machine learning, neural network, artificial intelligence, or expert module and analyzed as part of image recognition or other machine vision features.

As described above in the context of the de-artifacting function, each of the display processing function and match processing function may themselves include machine learning, neural network, artificial intelligence, or expert modules, and may be configured and performed on one or several devices that will vary by a particular implementation. For example, in some implementations where advanced anatomy recognition features are performed by a remote server (106), the remote server (106) may also be configured to perform the match processing function. As another example, in some implementations where a device such as the image processor (104) is used as a display device and/or to otherwise aid the function of the endoscope (700), the image processor may be configured to perform the display processing function. In this manner and depending upon a particular implementation, each of the de-artifacting, match processing, and display processing functions may be performed on one or several devices that are best suited to perform that function based upon factors such as their processor, memory, or other capabilities, available processor time, and the availability of the image data (e.g., processing the image data incidentally to receiving the image data for another purpose).

When performing the display processing function, the system may crop (644) the image data to make it suitable for the intended display device, such as illustrated in FIGS. 29E and 29F by the pre-processing image data (682) and the post-processing image data (684), which is more suitable for display via a rectangular display. The parameters of the cropping operation (644) may be pre-configured, or may be automatically determined based upon an identification of the intended display, or may be determined based upon a user input (e.g., such as use of an instrument button (706, 708, 710) or other control to zoom or pan the image data until a desired displayed section is reached.

The display processing function may also include upsampling (646) the image data from a resolution, color depth, or other characteristic of the originally captured (630) image data so that it is suited to be displayed on the intended display device. This may include upsampling (646) the image data to increase its resolution (e.g., such as from an original capture resolution of 1920×1080 to a resolution of 2048×1536 that the destination display is capable of rendering). Such upsampling may be performed using an appropriately configured machine learning, neural network, artificial intelligence, or expert module that has been trained or configured based upon annotated anatomical image data of varying resolutions (e.g., a training dataset may include many anatomical images of the 2048×1536 target resolution, and may train a machine learning module to identify similar anatomical perspectives that are usable to upsample the target image data based in part upon the image data of the training dataset). FIG. 29C illustrates an example of image data (678) having a relatively low resolution, such that pixilation of the anatomy is visible. FIG. 29D provides an example of image data (680) after upsampling (646), where the overall image is not necessarily more detailed, but pixelization and jagginess, especially at edges, is less pronounced.

The display processing function may also include adjustments (648) to image data brightness, contrast, or other image characteristics so that it is suited to be displayed on the intended display device. The image data (684) of FIG. 29F illustrates an example of image data that has been cropped and brightened for display on a particular display device, and has been previously described the parameters for automated brightening (648) may be based upon user configurations or inputs, or may be based upon an identification of the intended display device and a parameter selection that utilizes the full range and depth of colors or other visual characteristics of that display device. Once the display processing function is complete, the modified image data may be provided (650) to a display function that is configured to cause the image data to display via the intended display device.

The match processing function may occur in parallel with the display processing function, since each function can be performed on an isolated copy of the image data. This is advantageous where, for example, the display processing function is performed by a first device or processor, and the match processing function is performed by a different second device or processor. The match processing function is configured to prepare the image data so that it may analyzed by an object recognition or other machine vision process while maximizing the efficiency of this analysis and the accuracy of results. As an example, a particular machine learning module configured to identify particular anatomy or anatomy characteristics may be trained using training datasets that include annotated anatomical images having a resolution of 1920×1080, and/or that were captured in a curated or controlled manner (e.g., in consistent or controlled lighting conditions, with a controlled set of patients, etc.).

However, images provided to that machine learning module may have different resolutions, may be captured during different procedures, may be captured from different patients, may be captured in lighting conditions that are brighter or darker, and so on. The match processing function may be configured to process and modify input image data towards a particular normalized standard and structure that is based upon the characteristics of the training data, or the configurations of the expert module, and so on, and may include normalizing for resolution, color, brightness, patient type, procedure type, and other characteristics. The image data may also be restructured into a more complex form as part of this pre-processing (e.g., such as conversion from flat pixel image data to a segmentation map, layered image file, or other class or container structure).

As an example, this may include grouping (654) the image data into sub-groups or tiles whose size is selected to be optimized for processing by the hardware performing the match processing function (e.g., particularly to take advantage of the limited bit size that very high speed processors and very high speed memories are capable of processing or storing, such as an L1 cache or L2 cache), and then operating on those tiles individually instead of the entirety of the image data. The system may convolute and downsample (656) the image data for multiple layers, contracting the image data until all features are mapped to a single output vector. The system may then convolute and upsample (658) the image data for multiple layers in order to create (660) an output segmentation map that is readily usable by the image recognition or other machine vision function. Once created (660), the segmentation map may be provided (662) to the image recognition function. In this manner, the segmentation map or other output of the match processing function may be normalized towards standard characteristics based upon the trained artificial intelligence or other configured module (e.g., referencing FIGS. 29C and 29D, a pixelized and/or low resolution input image such as that shown in FIG. 29C may be compared to training data including images of a quality and resolution such as that shown in FIG. 29D).

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:

1. An endoscope system comprising:
   (a) an endoscope comprising a body, a sheath receiver positioned at a distal end of the body, a shaft extending from the sheath receiver and having a distal tip, and a camera at the distal tip of the shaft, wherein the shaft of the endoscope is rigid;
   (b) a control board positioned within the body and communicatively coupled to the camera, via a cable set that runs within the shaft, to receive image data;
   (c) a receiving port positioned within the body, communicatively coupled to the control board to provide procedure data to an external device via the receiving port;
   (d) a sheath configured to be removably installed on the shaft, the sheath comprising an optical interface at a distal end of the sheath, wherein, when the sheath is installed on the shaft:
      (i) a proximal end of the sheath couples to the sheath receiver such that the shaft is fully enclosed; and
      (ii) the optical interface is positioned proximate to and substantially perpendicular to an optical axis of the camera,
   wherein a processor of the control board is configured to determine that the sheath is installed on the endoscope and usable for a procedure and, in response:
   (i) cause the camera to capture a set of image data during a procedure performed with the endoscope; and
   (ii) cause the set of image data to display on a display of the external device,
   wherein the sheath receiver comprises a first sheath coupling that is communicatively coupled to the control board; and the sheath comprises a sheath memory that is configured to store a feature dataset, and that comprises a second sheath coupling, wherein the sheath memory is positioned such that the first sheath coupling couples with the second sheath coupling when the sheath is installed on the endoscope; wherein the processor is further configured to:
   (i) receive the feature dataset from the sheath memory; and
   (ii) determine that the sheath is installed on the endoscope and usable for a procedure based on the feature dataset;
   (iii) create a set of procedure data during the procedure, wherein the set of procedure data describes results of the procedure, and store the set of procedure data on the sheath memory;
   (iv) create a set of troubleshooting data during the procedure, wherein the set of troubleshooting data describes errors and diagnostic data arising from the procedure; and
   (v) store at least a portion of the set of image data on the sheath memory.

2. The endoscope system of claim 1, wherein the feature dataset is associated with a particular procedure type, and wherein the feature dataset describes one or more image processing features that are applicable to the particular procedure type, and one or more pre-configured settings for the endoscope that are applicable to the particular procedure type, wherein the processor is further configured to:
  (i) configure one or more endoscope settings for the particular procedure type based on the feature dataset, wherein the one or more endoscope settings comprise one or more of camera resolution, camera frame rate, illumination output, and control mapping for a set of buttons of the endoscope; and
  (ii) provide the feature dataset to the external device, wherein the feature dataset is configured to cause the external device to perform the one or more image processing features when displaying the set of image data on the display.

3. The endoscope system of claim 1, wherein:
  (a) the sheath receiver comprises a first sheath coupling that is communicatively coupled to the control board;
  (b) the sheath comprises:
    (i) a second sheath coupling positioned such that the first sheath coupling couples with the second sheath coupling when the sheath is installed on the endoscope; and
    (ii) a light source coupled to an exterior of the sheath at the distal end of the sheath;
  (c) the sheath sidewall comprises a second cable set that connects the second sheath coupling to the light source; and
  (d) the processor is further configured to selectively control output of the light source when the sheath is installed on the endoscope.

4. The endoscope system of claim 1, wherein:
  (a) the sheath receiver comprises a first sheath channel that is in fluid communication with a pump that is operable by the processor to provide a flow of liquid or a flow of gas;
  (b) the sheath comprises:
    (i) a second sheath channel positioned such that the first sheath channel couples with the second sheath channel when the sheath is installed on the endoscope; and
    (ii) a fluid opening on an exterior of the sheath at the distal end of the sheath, wherein the sheath comprises a sidewall channel through which the second sheath channel is in fluid communication with the fluid opening; and
  (c) the processor is further configured to selectively control output or input of the fluid opening by operation of the pump.

5. The endoscope system of claim 1, wherein the processor is further configured to:
  (a) during the procedure, receive a portion of the set of image data as an analog signal from the camera;
  (b) encode the portion into a digital signal;
  (c) perform at least one image processing modification to the portion; and
  (d) provide the modified digitally encoded portion to the external device to cause the set of image data to display on the display of the external device.

6. The endoscope system of claim 5, wherein:
  (a) the endoscope comprises a signal amplifier positioned within the body or proximate to the camera at the distal tip of the shaft, in order to minimize a length of the cable set coupling the camera to the amplifier; and
  (b) the signal amplifier is configured to amplify the analog signal of the portion, and provide the amplified portion to the control board.

7. The endoscope system of claim 6, wherein the body comprises an electrical ground, and wherein:
  (a) the shaft is comprised of a metal that provides passive signal shielding of the cable set positioned therein;
  (b) substantially the entire length of the cable set is contained within the shaft; and
  (c) a ground cable within the body couples the proximal end of the shaft to the electrical ground of the body.

8. The endoscope system of claim 1, wherein the endoscope further comprises a set of light emitting diode ("LED") illuminators positioned at the distal tip of the shaft and configured to provide illumination in a direction substantially parallel to the optical axis of the camera, wherein:
  (a) the set of LED illuminators are communicatively coupled to the control board via the cable set; and
  (b) the processor is configured to selectively control the output of the set of LED illuminators.

9. The endoscope system of claim 8, wherein the camera is positioned at a first point of the longitudinal axis of the distal tip that is the most distal point, and wherein the set of LED illuminators are positioned at a second point of the longitudinal axis of the distal tip that is a less distal point.

10. The endoscope system of claim 9, wherein:
  (a) the distal tip further comprises an optical shield positioned at a third point of the longitudinal axis of the distal tip that is between the first point and the second point;
  (b) the optical shield extends outwards from the distal tip along the lateral axis of the distal tip; and
  (c) when the sheath is installed on the endoscope, the optical shield prevents a portion of illumination from the LED illuminators from directly striking the optical interface.

11. The endoscope system of claim 10, wherein the optical shield prevents illumination from between about 50% and 100% of the of a light emitting surface of the set of LED illuminators from directly striking the optical interface.

12. The endoscope system of claim 9, wherein the camera comprises a hood portion that surrounds the camera, the hood portion comprising a sidewall that extends along the longitudinal axis beyond the first point at which the camera is positioned.

13. The endoscope system of claim 1, further comprising a point-of-care sterilization cabinet configured to be transported to the location of the procedure by hand, wherein the point-of-care sterilization cabinet comprises:
  (a) a drawer configured to store a plurality of endoscopes, including the endoscope; and
  (b) an ultraviolet light emitter positioned to project ultraviolet light towards the plurality of endoscopes stored in the drawer when the drawer is closed.

14. An endoscope system comprising:
  (a) an endoscope comprising a body, a sheath receiver positioned at a distal end of the body, a shaft extending from the sheath receiver and having a distal tip, and a camera at the distal tip of the shaft, wherein the shaft of the endoscope is rigid;
  (b) a control board positioned within the body and communicatively coupled to the camera, via a cable set that runs within the shaft, to receive image data;
  (c) a receiving port positioned within the body, communicatively coupled to the control board to provide procedure data to an external device via the receiving port;

(d) a sheath configured to be removably installed on the shaft, the sheath comprising an optical interface at a distal end of the sheath, wherein, when the sheath is installed on the shaft:
  (i) a proximal end of the sheath couples to the sheath receiver such that the shaft is fully enclosed; and
  (ii) the optical interface is positioned proximate to and substantially perpendicular to an optical axis of the camera;
wherein a processor of the control board is configured to determine that the sheath is installed on the endoscope and usable for a procedure and, in response:
  (i) cause the camera to capture a set of image data during a procedure performed with the endoscope; and
  (ii) cause the set of image data to display on a display of the external device,
wherein the sheath receiver comprises a first sheath channel that is in fluid communication with a pump that is operable by the processor to provide a flow of liquid or a flow of gas,
wherein the sheath comprises:
  (i) a second sheath channel positioned such that the first sheath channel couples with the second sheath channel when the sheath is installed on the endoscope; and
  (ii) a fluid opening on an exterior of the sheath at the distal end of the sheath, wherein the sheath comprises a sidewall channel through which the second sheath channel is in fluid communication with the fluid opening; and
wherein the processor is further configured to selectively control output or input of the fluid opening by operation of the pump.

15. An endoscope system comprising:
(a) an endoscope comprising a body, a sheath receiver positioned at a distal end of the body, a shaft extending from the sheath receiver and having a distal tip, and a camera at the distal tip of the shaft, wherein the shaft of the endoscope is rigid;
(b) a control board positioned within the body and communicatively coupled to the camera, via a cable set that runs within the shaft, to receive image data;
(c) a receiving port positioned within the body, communicatively coupled to the control board to provide procedure data to an external device via the receiving port;
(d) a sheath configured to be removably installed on the shaft, the sheath comprising an optical interface at a distal end of the sheath, wherein, when the sheath is installed on the shaft:
  (i) a proximal end of the sheath couples to the sheath receiver such that the shaft is fully enclosed; and
  (ii) the optical interface is positioned proximate to and substantially perpendicular to an optical axis of the camera,
wherein a processor of the control board is configured to determine that the sheath is installed on the endoscope and usable for a procedure and, in response:
  (i) cause the camera to capture a set of image data during a procedure performed with the endoscope; and
  (ii) cause the set of image data to display on a display of the external device,
wherein the endoscope further comprises a set of light emitting diode ("LED") illuminators positioned at the distal tip of the shaft and configured to provide illumination in a direction substantially parallel to the optical axis of the camera, wherein:
  (a) the set of LED illuminators are communicatively coupled to the control board via the cable set; and
  (b) the processor is configured to selectively control the output of the set of LED illuminators,
wherein the camera is positioned at a first point of the longitudinal axis of the distal tip that is the most distal point, and wherein the set of LED illuminators are positioned at a second point of the longitudinal axis of the distal tip that is a less distal point,
wherein:
  (a) the distal tip further comprises an optical shield positioned at a third point of the longitudinal axis of the distal tip that is between the first point and the second point;
  (b) the optical shield extends outwards from the distal tip along the lateral axis of the distal tip; and
  (c) when the sheath is installed on the endoscope, the optical shield prevents a portion of illumination from the LED illuminators from directly striking the optical interface.

16. The endoscope system of claim 15, wherein the optical shield prevents illumination from between about 50% and 100% of the of a light emitting surface of the set of LED illuminators from directly striking the optical interface.

17. An endoscope system comprising:
(a) an endoscope comprising a body, a sheath receiver positioned at a distal end of the body, a shaft extending from the sheath receiver and having a distal tip, and a camera at the distal tip of the shaft, wherein the shaft of the endoscope is rigid;
(b) a control board positioned within the body and communicatively coupled to the camera, via a cable set that runs within the shaft, to receive image data;
(c) a receiving port positioned within the body, communicatively coupled to the control board to provide procedure data to an external device via the receiving port;
(d) a sheath configured to be removably installed on the shaft, the sheath comprising an optical interface at a distal end of the sheath, wherein, when the sheath is installed on the shaft:
  (i) a proximal end of the sheath couples to the sheath receiver such that the shaft is fully enclosed; and
  (ii) the optical interface is positioned proximate to and substantially perpendicular to an optical axis of the camera,
wherein a processor of the control board is configured to determine that the sheath is installed on the endoscope and usable for a procedure and, in response:
  (i) cause the camera to capture a set of image data during a procedure performed with the endoscope; and
  (ii) cause the set of image data to display on a display of the external device,
wherein the endoscope further comprises a set of light emitting diode ("LED") illuminators positioned at the distal tip of the shaft and configured to provide illumination in a direction substantially parallel to the optical axis of the camera, wherein:
  (a) set of LED illuminators are communicatively coupled to the control board via the cable set; and
  (b) the processor is configured to selectively control the output of the set of LED illuminators, wherein the camera is positioned at a first point of the longitudinal axis of the distal tip that is the most distal point, and wherein the set of LED illuminators are positioned at a second point of the longitudinal axis of the distal tip that is a less distal point, wherein the camera comprises a hood portion that surrounds the camera, the hood portion comprising a sidewall that extends along the longitudinal axis beyond the first point at which the camera is positioned.

* * * * *